United States Patent [19]
Kleinerman

[11] Patent Number: 5,928,222
[45] Date of Patent: Jul. 27, 1999

[54] FIBER OPTIC SENSING TECHNIQUES IN LASER MEDICINE

[76] Inventor: Marcos Y. Kleinerman, 24 Jerome St., Southbridge, Mass. 01550

[21] Appl. No.: 08/699,971

[22] Filed: Dec. 7, 1996

Related U.S. Application Data

[60] Division of application No. 08/613,352, Mar. 11, 1996, Pat. No. 5,696,863, which is a continuation-in-part of application No. 08/305,252, Sep. 13, 1994, Pat. No. 5,499,313, which is a division of application No. 07/815,741, Jan. 2, 1992, Pat. No. 5,363,463, which is a continuation-in-part of application No. 07/491,942, Mar. 12, 1990, Pat. No. 5,096,277, which is a continuation-in-part of application No. 07/293,119, Jan. 3, 1989, abandoned, which is a continuation-in-part of application No. 07/102,835, Sep. 30, 1997, abandoned, which is a continuation-in-part of application No. 06/711,062, Mar. 12, 1985, Pat. No. 5,004,913, which is a continuation-in-part of application No. 06/608,932, May 14, 1984, Pat. No. 4,708,494, which is a continuation of application No. 06/405,732, Aug. 6, 1982, abandoned.

[51] Int. Cl.$^6$ ................................................ A61B 17/36
[52] U.S. Cl. ................................ 606/16; 606/15; 606/12
[58] Field of Search ........................... 606/10, 12, 13–16; 385/12; 250/227.11, 227.14, 227.18, 458.1, 459.1

[56] References Cited

U.S. PATENT DOCUMENTS

| | | | |
|---|---|---|---|
| 4,627,435 | 12/1986 | Hoskin | 606/10 |
| 4,695,697 | 9/1987 | Kosa | 606/13 |
| 4,852,567 | 8/1989 | Sinofsky | 606/16 |
| 4,932,934 | 6/1990 | Dougherty et al. | |
| 5,196,005 | 3/1993 | Doiron et al. | 606/15 |

*Primary Examiner*—Linda C.M. Dvorak
*Assistant Examiner*—Bryan K. Yarnell

[57] ABSTRACT

Methods and devices for medical treatment of biological tissue use fiber optic tips attached to the end of an optical fiber light guide for thermal treatment or photo-irradiation of said tissue, said tip including a photoluminescent material capable of acting as the tip's temperature probe. The photoluminescent material allows the tip to act as a controlled temperature surgical device or as a simple, efficient and easy to fabricate laser light diffuser.

8 Claims, 21 Drawing Sheets

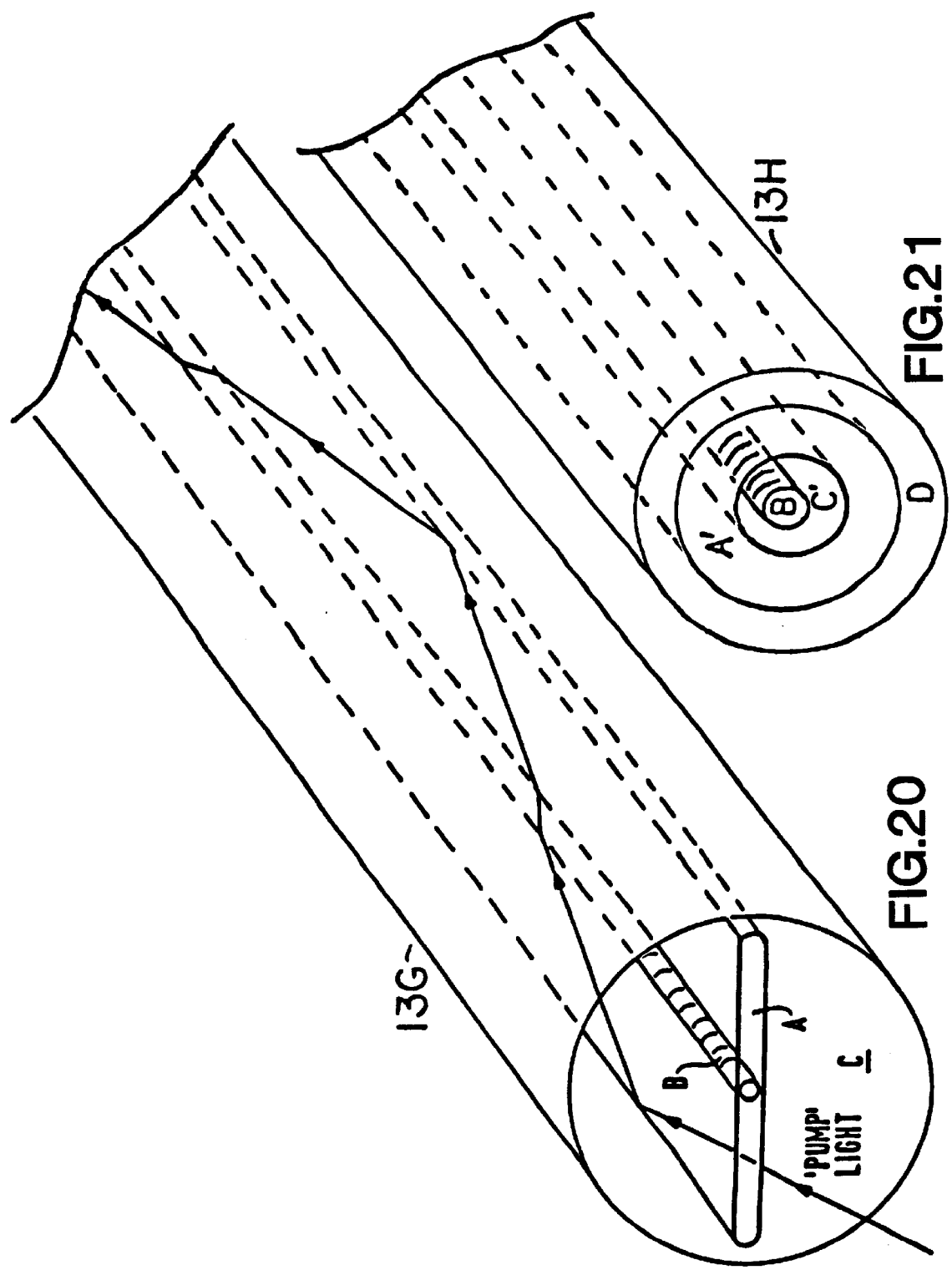

FIBER OPTIC SENSING TECHNIQUES IN LASER MEDICINE

CROSS-REFERENCE TO RELATED APPLICATIONS

This is a division, pursuant to 37 C.F.R. 1.60, of application Ser. No. 08/613,352 filed Mar. 11, 1996, now U.S. Pat. No. 5,696,863, which is a continuation-in-part (CIP) of application Ser. No. 08/305,252 filed Sep. 13, 1994 (now U.S. Pat. No. 5,499,313), which is a division of application Ser. No. 07/815,741 filed Jan. 2, 1992 (now U.S. Pat. No. 5,363,463), which in turn is a continuation-in-part (CIP) of application Ser. No. 491,942 filed Mar. 12, 1990 (now U.S. Pat. No. 5,096,277), which in turn is a CIP of application Ser. No. 293,119 filed Jan. 3, 1989, now abandoned, which in turn is a CIP of application Ser. No. 102,835 filed Sep. 30, 1987, now abandoned, which in turn is a CIP of application Ser. No. 711,062 filed Mar. 12, 1985 (now U.S. Pat. No. 5,004,913), which in turn was a CIP of application Ser. No. 608,932 filed May 14, 1984 (now U.S. Pat. No. 4,708,494), which in turn was a continuation of application Ser. No. 405,732 filed Aug. 6, 1982, now abandoned.

BACKGROUND OF THE INVENTION

This invention relates to new methods and devices for the remote sensing of physical variables with fiber optic systems, and more particularly to fiber optic sensing techniques in laser surgery.

DESCRIPTION OF THE PRIOR ART

Fiber optic sensing systems have been under development in recent years for the remote measurement of physical variables (also referred to as measurands) of interest in industry, medicine, transportation, and other fields of human endeavor. There are two main approaches to fiber optic sensing, as follows:

(a) The use of the optical fiber itself as the transducer, in a system which may be interferometric or non-interferometric, and (b) The use of a point transducer attached or otherwise optically connected to one or more optical fibers, the latter acting merely as light guides.

These and other approaches are discussed in a recent review by G. D. Pitt et al., *IEE Proceedings*, Vol. 132, Pt. J, No. 4, August 1985, pp 214–248.

In addition, optical fibers are used for transmitting information of sensors, whether optical or electrical, to a remote control station.

Interferometric sensing systems use the fibers themselves as transducers, and can achieve high sensitivities. They have, however, some disadvantages. They usually require single mode lasers, single mode fibers, and relatively complex instruments, and are often subject to drift and phase noise due to environmental factors other than the parameter sought to be measured. Further, they are not presently compatible with the industrial requirements for ruggedness. Non-interferometric systems, which usually use multimode fibers and non-coherent light sources, are simpler, more rugged, and are capable of meeting most of the sensitivity requirements of industry. The methods and devices of this invention are based on non-interferometric systems.

Many fiber optic sensing systems are based on light intensity changes produced by the action of the measurand. In order to obtain a reliable measurement of the physical variable with such systems, it is necessary to compare the optical signal generated by the measurand to a reference signal which is not affected by this measurand. This is done in the prior art by one of the following ways:

(a) If the sensor is not spectrally selective, by splitting the light output from the interrogating light source into two separate beams each carried by a separate fiber. One of the beams is made to interact with the measurand, where its intensity is modulated according to the measurand's value. The other beam is used as a reference. The modulated beam and the reference beam are sent through separate optical paths to separate photodetectors, and the resulting electrical signals are compared. The value of the measurand is determined from the relative values of the two electrical signals.

(b) If the sensor is spectrally selective, by interrogating probe with light of an intensity distributed in a known manner between two wavelength regions, the intensities of each of these spectral components modulated in a known, different manner by the probe. There are two ways to accomplish this. One way is to carry both spectral components simultaneously by the same fiber, and then to separate them at the fiber output (after interaction with the sensor) by means of wavelength-selective optical filters, feeding each separate beam to a separate photodetector. The other way is to use a switching device to send both spectral components alternately through the same fiber system to the same photodetector. The latter method was used to measure temperature by monitoring the temperature-dependent light transmission of semiconductor crystals within their absorption band edge (Kyuma et. al., *IEEE J. Quant. Electron.*, QE-18(4), 677 (1982)).

Each of the above methods is subject to error, due to unequal detector draft, varying losses in the separate optical paths and/or unequal fluctuations in the intensities of the spectral components of the interrogating light source(s).

In the prior art sensors described above, so-called intensity sensors, the value of the measurand is determined indirectly from the attenuation of the intensity $P_o$ of the interrogating light incident on the sensor to a transmitted value $P_o(1-\alpha)$. The value of $\alpha$, which is an indicator of the value of the measurand, is estimated indirectly from the measurement of the transmitted light intensity. It is well known that such measurements can not be made with a high degree of accuracy when the optical density is of the order of $10^{-3}$ or lower for a single, discrete sensor. The accuracy of said attenuation measurements is further degraded in the case of series-multiplexed sensors, where the attenuation measurements must be carried out by optical time domain reflectometry (OTDR) techniques, which consist of the measurement of the decrease of the intensity of the Rayleigh-backscattered light caused by each sensor. In this case a measurement with an accuracy of one percent may require the accurate and reproducible measurement of light intensity changes of a few parts per $10^4$. This is difficult to achieve with a relatively simple device, especially considering that Rayleigh-backscattered light signals are reletively weak, with an intensity down about 45 to 50 dB with respect to the intensity of the interrogating light at the same fiber location.

Most non-interferometric fiber optic sensing systems operate by measuring the measurand-dependent variable light transmission of the sensor, and their performance is subject to the inherent limitations discussed in the preceding paragraph. Temperature-sensing systems include, besides the one already mentioned by Kyuma et. al., the systems subject of U.S. Pat. Nos. 4,136,566 (Christensen), 4,302,970 (Snitzer et. al.), 4,278,349 (Sender), 4,307,607 (Saaski et.

al.), and the cryogenic temperature sensor described in NASA Technical Briefs, p.55, Spring, 1981. All of these systems are based on a temperature-dependent light attenuation.

Other sensor systems based on variable light attenuation and designed to measure a variety of measurands include the ones described in U.S. Pat. Nos. 4,356,448 (Brogardh et. al.), 4,433,238 (Adolfsson et. al.), and 4,523,092 (Nelson). There are many others, but they fall within the same category of attenuation sensors covered by these references.

Fiber optic sensing techniques are especially suited for distributed sensing and for the multiplexing of a multiplicity of discrete sensors, and considerable interest has developed in recent years in these applications. A comprehensive review has been published recently (J. P. Dakin, *J. Phys. E: Sci. Instrum* 20, 954 (1987), which discusses many approaches suggested or under development for these purposes. Some of these methods and approaches were first disclosed after the filing of the original application (Ser. No. 405,732) of which this is a Continuation in Part. OTDR techniques seem to be most extensively investigated, mainly coupled to the measurement of Rayleigh-backscattered light, but Raman and fluorescence variants have also been proposed. An anti-Stokes Raman technique has been proposed for measuring temperature (Dakin et. al., Electron. Lett. 21 569 (1985)) based on the temperature-dependent occupancy number of a vibrationally excited level in a glass. The method provides signals which are orders of magnitude weaker than a method, also based on a temperature-dependent occupancy number of a vibrationally excited molecular level, subject of said original application Ser. No. 405,732 and using fluorescence conversion, and can be, regarded as a less sensitive variant of said earlier invention. A recently proposed fluorescence technique proposed by Dakin, mentioned in said review article, is based on temperature-dependent spectral changes in the fluorescence spectral distribution of some fluorescent dyes, in contrast to the methods of this invention, which do not require any temperature-dependent change in any fluorescence property and can, therefore, be implemented with most dyes.

A method for measuring distributed forces has recently been proposed by Farries and Rogers and discussed in another review article (A. J. Rogers, *J.Phys. D: Appl. Phys.* 19 2237 (1986), based on the effect of force-induced changes of the polarization properties of a single mode fiber on the stimulated Raman gain, under intense optical 'pump' pulses, from sensing points along the optical fiber. The method has the disadvantage (among others) that polarization changes at one point along the fiber affect the polarization properties of the fiber along the rest of its length, and the results are thus difficult to interpret.

Macedo et. al. (U.S. Pat. No. 4,342,907 describe an interesting OTDR-based system for the measurement of distributed forces acting at different pre-determined points along a fiber optic cable. These forces divert a fraction of the intensity of the interrogating light propagating along the fiber from the fiber core into the cladding. This diverted light is removed by a coupler mechanically attached to the cable at each sensing point and transferred either to a second fiber optic cable (the return light guide) by means of another coupler, which directs this light to a photodetector in the OTDR device, or reflected back by an external detector into the same fiber optic cable towards the OTDR device. While the system has the advantage that it produces optical signals which are a linear function of the intensity of the light forced out of the core, and are free of the baseline background of the interrogating light intensity, it is mechanically and optically complex, requiring at least one directional coupler per sensing point, and is unsuitable for detecting or measuring forces at points other than pre-determined ones.

It is an object of the present invention to provide methods and devices which eliminate or minimize the sources of error discussed above, said methods and devices producing both a single beam and a reference beam from a single light source, whether this be a broad band or a narrow band or monochromatic source, carrying both beams simultaneously through a single fiber to a single photodetection station, and separating, measuring and ratioing by simple means the electrical signals generated at the photodetection station by both the signal beam and the reference beam.

It is another object of this invention to provide a simple method for measuring directly and accurately small attenuations of an interrogating light beam produced by the action of a measurand, by generating a signal light intensity proportional to said attenuation and free of the intensity of the interrogating light incident on or transmitted by the sensor.

Still another object of the present invention is to provide new methods and devices for the measurement of diverse measurands at a plurality of remote locations simultaneously or quasi-simultaneously, using a single excitation light source and a single photodetector, with the individual probes attached to a single unbroken optical fiber, said measurements being only minimally affected by fluctuations of the intensity of the interrogating light beam, fiber losses or detector drift.

Yet another object of the present invention is to provide a long unbroken optical fiber as a distributed sensor, said fiber being sensitive to both mechanical forces and temperatures acting at different points along the fiber, and associated devices for the accurate measurement of the location and magnitude of said distributed temperatures and mechanic forces.

Other objects of the present invention will in part be apparent from the following discussion and will in part appear hereinafter.

BRIEF SUMMARY OF THE INVENTION

These and other objects are accomplished by using so-called intensity sensors in a new manner whereby, in a preferred embodiment of the invention, interrogating light is launched into the core of an optical fiber probe for a measurand, wherein a fraction $\alpha$ of its initial intensity is removed from the core, the value of $\alpha$ being an indicator of the value of the measurand. Instead of discarding this removed fraction as in the prior art and estimating its value indirectly from the light intensity $P_o(1-\alpha)$ transmitted by the probe, the removed light is captured and processed into an optical signal separable from the transmitted interrogating light and from signals from measurands acting simultaneously at any other point(s) on the fiber, but carried by the same fiber to a photodetection station, so that both the intensities of the transmitted interrogating light light beam and that of said removed fraction $\alpha$, the value of $\alpha$ being an indicator of the value of the physical parameter, can be measured to give a ratiometric (referenced) reading of the value of the measurand, unaffected or only minimally affected by fluctuations of the intensity of the interrogating light, fiber losses or detector drift. The processing of $\alpha$ into a separable, directly measurable signal, can be effected either in the optical spectral domain, by luminescence or Raman conversion into a light of different wavelengths from those of the interrogating light, or in the time domain, using pulsed or AC-modulated interrogating light and processing said fraction α into a signal which arrives at the photodetector either at a different time or with a phase shift relative to the interrogating light. An important feature of the invention is that the sensing materials it uses can be homogeneously incorporated into components of long optical fibers, allowing the measurement of temperatures and/or forces distributed over many locations, simultaneously and with a single fiber probe.

In accordance with the above description, the invention comprises the methods and devices for processing said fraction α into said separable and directly measurable signal, including the novel optical fibers which are necessary and essential for making said methods and devices operable, and the application of said methods and devices for the sensing of distributed physical parameters using a continuous length of one of said novel optical fibers as the sensing probe. The methods and devices for sensing said distributed physical parameters use time division multiplexing (TDM) techniques, including both the back-scattering TDM techniques better known as "optical time domain reflectometry" (OTDR) techniques used in most of the distributed sensing systems of this invention (including the backward-stimulated light amplification and the Raman back-scattering techniques, which do not usually measure reflected light), and the 'forward' TDM force-sensing techniques described in section 3.5. The most common TDM techniques are the OTDR techniques. Accordingly, the claims of this application are drawn to the novel optical fibers which are necessary and essential for making said techniques operable, and to the OTDR and other TDM methods and devices suitably modified according to the teachings of the invention.

In contrast to prior art sensing methods using luminescent materials, the luminescence conversion techniques of this invention do not require any change in the luminescence spectral distribution, quantum efficiency or decay time of the sensor materials.

Definitions and Symbols

Within the context of this application, I am using the following definitions:

Light: optical radiation, whether ultraviolet, visible, or infrared.

Vibronic material: any material whose molecular electronic ground level comprises a plurality of vibrational sublevels with energies higher than that of the lowest occupied level of the material.

Vibronic level: a vibrational sublevel of the electronic ground state of a vibronic material, having an occupancy number which increases with increasing temperature.

Luminescence converter: a material which absorbs light of wavelengths $\lambda_s$ and emits at least a fraction of the energy of the absorbed light as luminescence light including wavelengths $\lambda_f$ different from $\lambda_s$.

Raman converter: a material which, when exposed to light of any photon energy $E_s$, converts a fraction of the intensity of said light into light of a photon energy different from $E_s$ by an amount approximately equal to the energy of a vibrational quantum of said material.

Occupancy number of an energy level (or sublevel): the fraction of the molecules or ions of the material occupying said energy level (or sublevel).

Population inversion: a condition in which the occupancy number of an excited level is greater than that of a lower level to which the molecules or atoms of the excited level decay through a radiative transition.

Measurand, physical variable or physical parameter: any physical property whose magnitude can change. Examples: temperature, force, flow rate, level, position.

Interrogating light: light launched into a sensing system for the purpose of generating an optical signal indicative of the value (magnitude) of the physical parameter being sensed or measured.

Excitation light: interrogating light which generates a luminescence or Raman-shifted light of an intensity determined by the magnitude of the measurand.

Force: any action which, on an optical fiber or other optical probe, affects the transmission of light along it. Examples: stress, pressure, sound waves.

$\lambda_v$: a wavelength or wavelengths of interrogating light at which the absorption coefficient of a sensing probe is temperature-dependent.

$\lambda_f$: a wavelength or wavelengths of light generated at a sensing probe by interrogating light of wavelength $\lambda_s$ and different from $\lambda_s$.

α: the fraction of the intensity of interrogating light attenuated within a sensing probe at a sensing point under the action of a measurand.

$\alpha_s$ and $\alpha_v$: fractions of the intensity of an interrogating light of wavelengths $\lambda_s$ and $\lambda_v$, respectively, attenuated within a sensing probe at a sensing point.

Effective optical path length of a light guide: the product of the actual path length of the light guide times its index of refraction.

Cladding: a light-guiding region surrounding a fiber core, whether or not in physical contact with the core and having a thickness no smaller than that of the shortest wavelength of optical radiation transmitted by pure silica, and regardless of the value of its index of refraction.

Proximal end (first end) and distal end of an optical fiber: the end into which interrogating light is launched (injected) is the proximal end. The other end is the distal end.

BRIEF DESCRIPTION OF THE DRAWINGS

FIGS. 20 and 21 illustrate sensor fibers suitable for concentrating the optical powers of 'pump' light sources into fiber cores of cross-sectional area smaller than the emitting area of the light source.

Figure 1:
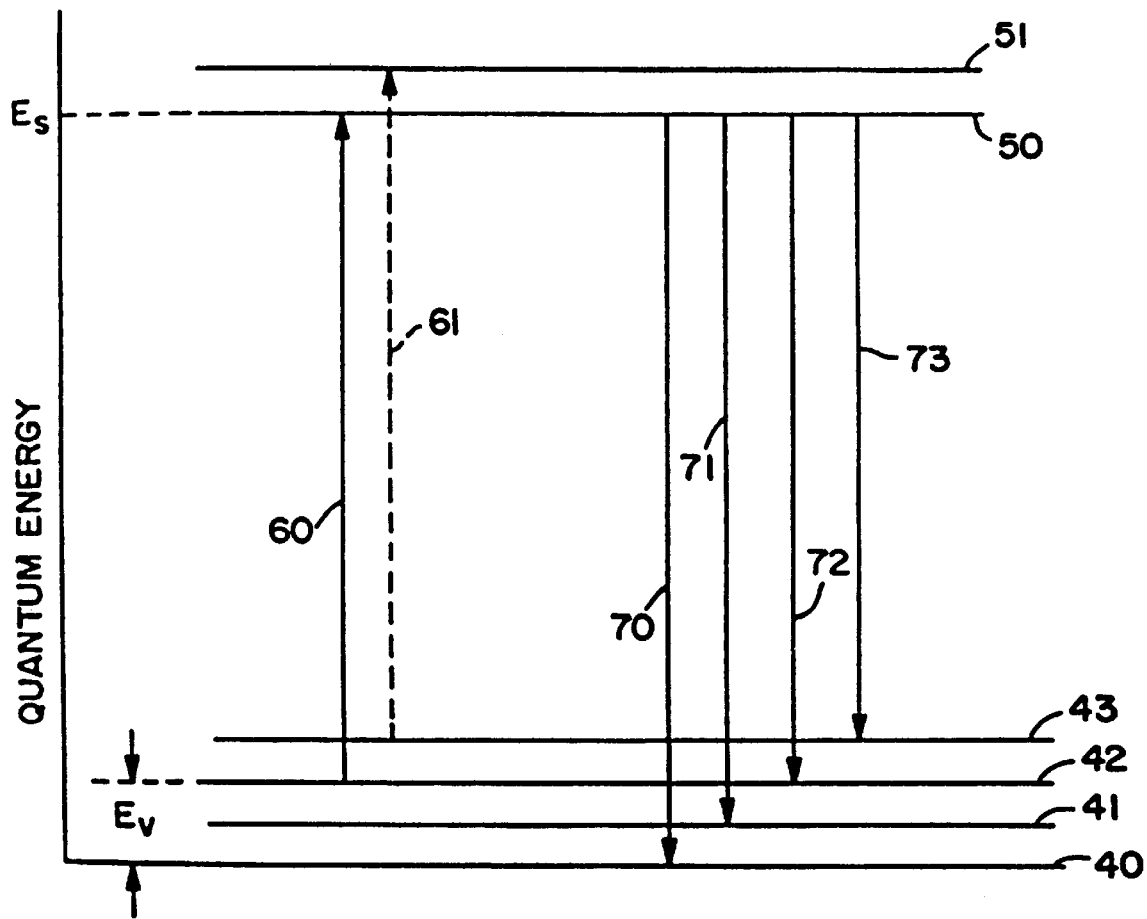
FIG. 1 is an energy flow diagram, at the molecular level, of a class of luminescent materials useful for measuring temperature according to the invention.

DETAILED DESCRIPTION OF THE INVENTION 1.0 The Direct Measurement of Small Optical Attenuations Caused by Physical Variables In fiber optic sensing technology, optical attenuations are conventionally measured by indirect techniques. As the following example shows, such approach is not suitable for the measurements of small attenuations. Suppose that one is measuring temperature with an optical probe characterized by a temperature-dependent optical absorption coefficient at a wavelength $\lambda_v$. The optical density of the probe is low enough that, at a temperature of 300 kelvins (K), the probe absorbs a fraction $\alpha_v$ equal to 0.0100 of the power $P_o$ of the interrogating light at that wavelength. The fraction $\alpha_v$ is not measured directly in the prior art in optical sensors. What is measured is the power P of the light transmitted by the probe. This is, disregarding scattering or other losses, equal to 0.9900 $P_o$. The value of $\alpha_v$ is derived from the difference $(P_o-P)/P_o$. Assume now that at 300 K the temperature coefficient of $\alpha_v$ is equal to 1.67 percent per K, that is, a temperature increase of 1 K increases $\alpha_v$ by 1.67 percent. But one measures P, not $\alpha_v$, and when $\alpha_v$ changes by 1.67 percent P changes by only 0.017 percent, a change of less than 2 parts per 10,000. Such a small change is difficult to measure accurately with ordinary photometric equipment.

Using the principles of this invention, one can measure $\alpha_v$ directly, and obtain an actual, directly measurable light intensity which does vary by 1.67 percent per kelvin. To do this, one uses a probe as described in the preceding paragraph, with the additional characteristic that the absorbed light of wavelength $\lambda_v$ is converted by the probe into luminescence light having wavelengths $\lambda_f$ different from $\lambda_v$. The intensity of this luminescence light, $I_f$, will then be an approximately linear function of $\alpha_v$ according to the relation $$I_f = P_o \alpha_v \phi (\lambda_v/hc) \text{ photons} \cdot \text{sec}^{-1}$$

where

φ is the luminescence quantum efficiency of the probe material;

h is Planck's constant; and c is the velocity of light in a vacuum.

If $P_o$ is kept constant, then $$I_f = B \alpha_v \text{ photons} \cdot \text{sec}^{-1}$$

where B is a constant.

It is important to be able to measure small attenuations accurately, especially with multiplexed or distributed sensors, in which the attenuation of the interrogating light per sensing point must be kept low.

The above method is useful for increasing the accuracy of measurements from any kind of optical attenuation, not just attenuation by absorption. For example, microbending sensors work by forcing a fraction of the intensity of the interrogating light propagating along the core of an optical fiber out of the core and into the fiber cladding. According to the teachings of this invention, one can incorporate a luminescent material or a Raman scattering material into the cladding and convert the light entering into the cladding under the action of the microbending force into either luminescence light or Raman-shifted light, the intensity of which is directly proportional to the fraction α removed from the core. One can then guide the converted radiation back along the same fiber to the photodetection station.

Alternatively, one can carry the fraction α through a fiber cladding, without luminescence conversion but rendered separable from the interrogating light being propagated through the core by the time domain separation technique described in section 3.2 hereinafter. The spectral or temporal separation of the signals from the interrogating light, plus signal intensities which are orders of magnitude stronger than Rayleigh-backscatter signals, permit the multiplexing of a much greater number of sensing points on a single sensing fiber than is possible with the prior art, for the same intensity of the interrogating light and the same photodetector.

2.0 Specific Applications 2.1 Fiber Optic Temperature Sensors

The teachings discussed above can be used as a basis for constructing novel sensors with greatly enhanced performance compared to the prior art. As discussed above in the section "Description of the Prior Art", a number of fiber optic temperature sensors are based on optical transmission measurements of a temperature-dependent light absorption. In this section I describe improved sensors using vibronic materials and wavelength conversion of a temperature-dependent absorbed fraction of the intensity of the interrogating light, and present a theoretical analysis of some physical systems suitable for use in practical embodiments. The analysis is deliberately oversimplified to emphasize the aspects most relevant to the invention. It is not claimed that the quantitative relationships are followed rigorously in all practical cases.

Preferred sensors are luminescent materials operated according to the principles described and illustrated with reference to FIG. 1. The luminescent material has a ground electronic energy level which comprises vibronic levels 40, 41, 42, 43 and other levels which, for the sake of simplicity, are not shown. The lowest excited electronic level comprises vibrational sublevels 50, 51, and other vibrational sublevels not shown. The vertical arrowed line 60 represents an optical electronic transition produced by the absorbed excitation light, from level 42 to vibrational sublevel 50, which have fixed energies $E_v$ and $E_s$, respectively, relative to level 40. The length of line 60 corresponds to the photon energy of the optical transition and, hence, to the specific wavelength $\lambda_v$ of the excitation light. This wavelength obeys the relation $\lambda_v = hc/(E_s - E_v)$, where h is Planck's constant and c is the velocity of light in a vacuum. The wavelength $\lambda_v$ can excite only molecules occupying vibronic level 42 and, to a smaller extent, molecules occupying slightly higher levels, the excitation of which is represented by the dotted vertical line 61. Luminescence emission occurs from sublevel 50 to the vibronic levels of the ground electronic level, said emission represented by lines 70, 71, 72 and 73. As shown in FIG. 1, a considerable spectral portion of the emission occurs at photon energies higher (and wavelengths shorter) than that of the excitation light, and is commonly referred to as anti-Stokes luminescence.

In practice the vibronic material is often used as a solid solution, glassy or crystalline, in a transparent host material, said solid material constituting the temperature probe. The concentration of the vibronic material and the dimension of the probe along the direction of the illuminating light are chosen so that the probe absorbs only a fraction $\lambda_v$ of the nearly monochromatic excitation light within the temperature range of operation, and transmits the rest. The absorbed fraction obeys the following relation:

$$\lambda_v = 1 - 10^{-\epsilon c_o d(N_{42}/N)} \tag{1}$$

where

ε is the molar decadic absorption coefficient of the molecules occupying the vibronic level 42;

$c_o$ is the total molar concentration of the vibronic material;

d is the length of the sensor in the direction of the incident excitation light;

$N_{42}$ is the number of molecules of the vibronic material occupying vibronic level 42; and N is the total number of molecules of the vibronic material.

The ratio $N_{42}/N$ essentially follows the relation $$N_{42}/N = f^{-1} \cdot \exp(-E_v/kT) \tag{2}$$

where f is the so-called partition coefficient of the molecular system, k is the Boltzmann constant, and T is the absolute temperature. The expression $c_o \cdot f^{-1} \exp(-E_v/kT)$ is essentially the effective molar concentration of the molecules of the vibronic material occupying the vibronic level 42, and the quantity $10^{-\epsilon c_o d(N_{42}/N)}$ represents the fraction of the illuminating (interrogating) light which is transmitted by the probe, assuming no scattering and/or reflection losses, and equal to $(1-\alpha_v)$. Since $E_v$ and k are both constant, the ratio $E_v/k$ can be designated by the single constant β, for a given fixed wavelength $\lambda_v$ of the interrogating light.

At optical densities no greater than 0.02, $\alpha_v$ is approximately given by $$\alpha_v \approx 2.3 \epsilon c_o df^{-1} \exp(-E_v/kT) \tag{3}$$

At optical densities greater than 0.02 the relationship between $\alpha_v$ and the Boltzmann factor $\exp(-E_v/kT)$ becomes less linear, but equations (1) and (2) are still valid, and the method can be used at high, low or intermediate optical densities.

The luminescence intensity $I_f$ generated by the light absorbed by the sensor obeys the relation $$I_f = P_o(\lambda_v/hc)\alpha_v \phi \text{ photons} \cdot \text{sec}^{-1} \tag{4}$$

where $P_o$ is the radiant power, in watts, of the incident excitation light, and φ is the luminescence quantum efficiency of the vibronic material.

Probes made from materials having high φ values can produce large signal-to-noise ratios even with optical densities lower than 0.01, provided that the optical system has at least a moderately high collection efficiency for the generated luminescence. Such efficiency is easily obtainable with state-of-the-art fiber optic systems.

The sum of the light intensity absorbed and the light intensity transmitted by a clear medium is constant. It follows, therefore, that as the absorbed fraction $\alpha_v$ increases with an increase in temperature according to equation (3), the intensity of the transmitted fraction must decrease accordingly. Since, according to equation (4), the intensity of the luminescence light is proportional to $\alpha_v$, it follows that the ratio of the intensity of the luminescence light to that of the transmitted light increases with an increase in temperature, and the ratio can be used as a temperature indicator. The ratio eliminates or minimizes any sources of error associated with fluctuations of the intensity of the illuminating light and fiber or connector losses.

The temperature coefficient of the luminescence intensity follows approximately the relation $$(1/I_o)(dI_f/dT) = E_v/kT^2 = \beta/T^2 \tag{5}$$

where $I_o$ is the luminescence intensity at a chosen reference temperature. For example, a material with a value of $E_v$ of 1200 cm$^{-1}$ has a coefficient of about two percent per kelvin at a temperature of 295 K.

Equations (3) to (5) show that the method of the preceding paragraphs requires only a temperature-dependent change in the optical absorption coefficient of the luminescent sensor material at wavelengths corresponding to photon energies lower than the energy $E_s$ of the excited emissive level. This property is shared by virtually all solid and liquid luminescent materials. The method does not require any temperature-dependent changes in the luminescence quantum efficiency, spectral distribution or decay time. Therefore, and in contrast to all other prior art methods, it can be implemented with most luminescent materials.

Experimental tests of equations (3) to (5) have been carried out with liquid solutions of three different dyes dissolved in dimethyl sulfoxide (DMSO). Two of the dyes, dye I and dye II are represented by the chemical structures

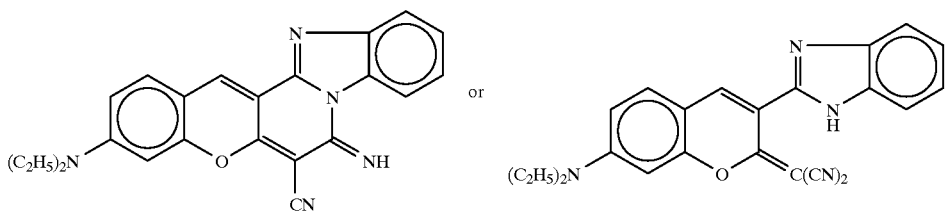

Figure 2:
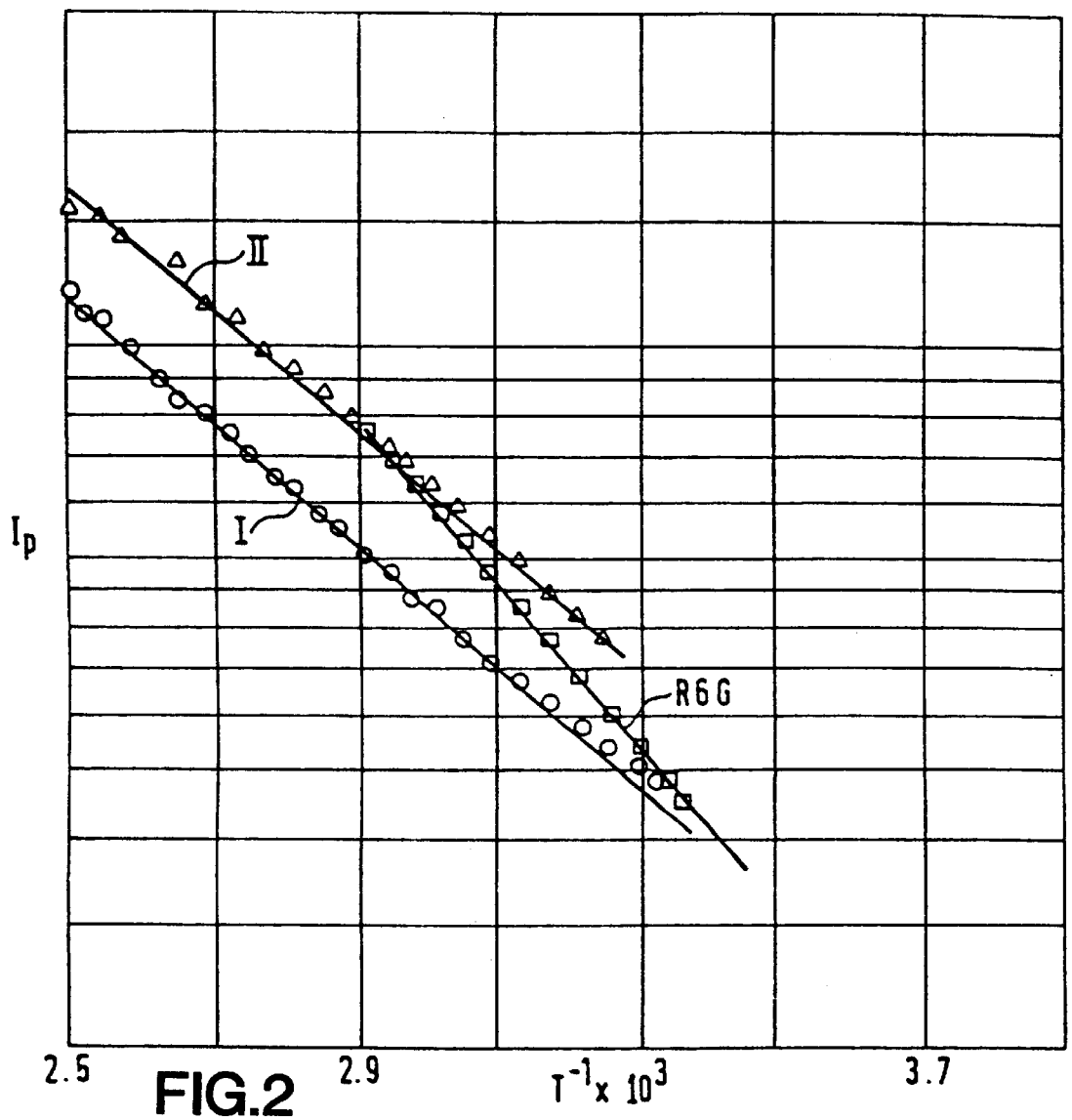
FIG. 2 shows the temperature dependence of the normalized fluorescence intensities of three organic dyes useful for measuring temperature according to this invention.

Dye I is the sulfonated derivative of Hostasol red GG (American Hoechst Corp.). Dye II has been described in U.S. Pat. No. 4,005,111 by Mach et. al. The third dye was the well known Rhodamine 6G (R6G). The dyes were dissolved in DMSO at concentrations of the order of $10^{-4}$ Molar and excited with light from a He—Ne laser ($\lambda$=633 nm) in a square cuvette. The fluorescence intensity was monitored at the wavelength of 612 nm, shorter than the wavelength of the excitation light. The experimentally measured fluorescence intensities $I_f$ were measured as a function of the absolute temperature T. Plots of $I_f v \cdot T^{-1}$ are shown in FIG. 2 for the three dyes. The behavior predicted by equations (3) and (5) was confirmed. The slopes of the lines drawn through the experimental points give $E_v$ values of 1380, 1355 and 1890 cm$^{-1}$ for dyes I, II and R6G, respectively. When these values are added to the excitation photon energy of 15803 cm$^{-1}$, one obtains $E_s$ values of $1.72 \times 10^4$ cm$^{-1}$ for dyes I and II, and $1.77 \times 10^4$ cm$^{-1}$ for R6G. These values are in good agreement with the $E_s$ values determined from the fluorescence spectra of these dyes.

The validity of equations (3) and (5) is independent of whether the sensor is a liquid or a solid. Although the laboratory reduction to practice was done with liquid solutions of these dyes, solid plastic solutions are preferred for practical measurements. Examples of suitable plastics are polystyrene, polymethyl methacrylate, polyurethanes and silicones.

An important advantage of this method for measuring temperature is that the value of $E_v$, which determines the optimum temperature range of operation, can be chosen and varied at will over a continuum of values simply by choosing, for any given vibronic material, the photon energy of the excitation light relative to the energy $E_s$ of the excited emissive level (sublevel 50 in FIG. 1). Thus, a single sensor can be used for measuring temperature over a wide range, from cryogenic temperatures up to the highest temperatures which the sensor can withstand without deterioration or severe thermal quenching of its luminescence. An additional advantage derives from the fact that there are many luminescent vibronic materials having absorption and luminescence spectra over a wide spectral region from the ultraviolet to the near infrared. One can choose, therefore, the wavelength region most suitable to one's needs. For instance, if it is required to transmit the optical signal over long distances via an optical fiber, one could choose a material with absorption and luminescence bands at wavelengths longer than 600 nanometers (nm).

Examples of vibronic materials suitable for measuring temperature according to this invention are plastic-soluble fluorescent dyes, like dyes II and R6G used for obtaining the data of FIG. 2. Other preferred dyes are those with excitation and fluorescence bands within the spectral region in the red and near infrared for which efficient and inexpensive light-emitting diodes (LED's) and laser diodes (LD's) are commercially available. These include dyes of the violanthrone family, including but not limited to the dye having the Color Index designation of Vat Green 1, having the chemical structure

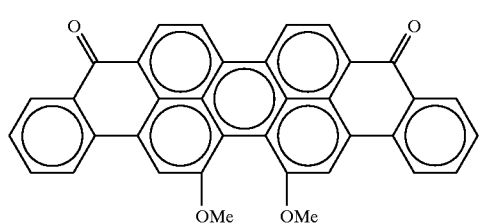

The solubility of these dyes in plastics can be increased by attaching to them solubilizing substituent groups like long chain or branched chain alkyl radicals. In dye Vat Green 1, for instance, the methyl (Me) radicals shown can be replaced by tert-butyl or longer chain radicals by techniques well-known to chemists.

Other vibronic materials suitable for meauring temperature according to the teachings of this invention include inorganic crystals doped with chromium(III) or other transition metal ions like nickel(II), cobalt(II) or vanadium(II).

Figure 3:
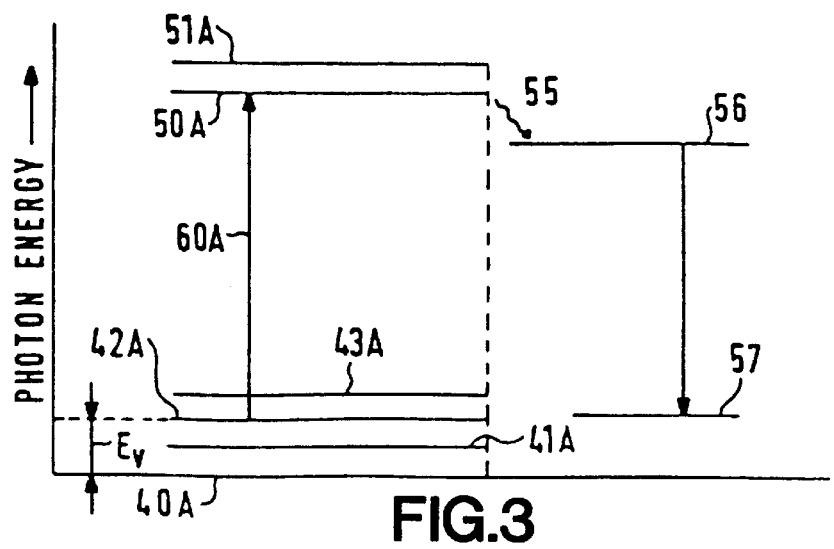
FIG. 3 is an energy flow diagram, at the molecular level, of another class of luminescent materials useful for measuring temperature according to this invention.

Another class of vibronic materials, also suitable for use as temperature sensors according to this invention, are described with reference to FIG. 3, which shows a simplified molecular energy level diagram somewhat similar to that of FIG. 1. What is different is that the emissive energy level is different from the level which is directly excited by the excitation light. Referring to FIG. 3, excitation of molecules occupying a vibronic level proceeds in the same manner as shown in FIG. 1 for the materials described hereinbefore. levels 40A, 41A, 42A, 43A, 50A and 51A are similar to levels 40, 41, 42, 43, 50 and 51, respectively. The same digits in both figures indicate the similarity of the excitation processes, and the A's were added to the levels of FIG. 3 to indicate that these levels belong to a different class of vibronic materials. The difference is that in this case the optically excited level 50A transfers at least a major part of its excitation energy, via a radiationless decay represented by the wavy line 55, to the lower level 56, of the same or of a difference molecular species. Luminescence occurs from level 56 to a lower level 57 or to any other lower-lying levels which may or may not include any of the levels 40A, 41A, 42A or 43A. Examples of this class of vibronic materials include virtually all Triplet→Singlet phosphorescent dyes, luminescent chelates of terbium(III) and europium(III), and some solid solutions of inorganic vibronic materials co-doped with other luminescent centers. Examples of the latter are crystalline or glassy materials co-doped with chromium(III) and neodymium(III), in which chromium(III) ions absorb the excitation light and transfer their excitation energy to the neodymium(III) ions, causing them to luminesce.

Some sensor materials can behave either according to the model of FIG. 1 or the model of FIG. 3, depending on the temperature range in which they operate. For example emerald, a chromium(III)-doped beryl, behaves according to the model of FIG. 1 at temperatures higher than ambient, and according to the model of FIG. 3 at cryogenic temperatures.

Two other classes of materials suitable for the practice of this invention are: (a) luminescent lanthanide ions dissolved at relatively high concentrations in crystalline or glassy hosts, and having at least one electronic energy level which can be thermally populated to a measurable extent at the temperatures being measured, and (b) luminescent semiconductors with a temperature-dependent absorption edge wavelength. Both casses of materials are characterized by an absorption coefficient which, within a relatively narrow spectral region, increases approximately exponentially with increasing temperature in essentially the same manner as with the vibronic materials described hereinbefore. Therefore, they are used in essentially the same manner and with the same methods as discussed above.

In the above-described embodiments the luminescent centers had a temperature-dependent absorption coefficient to light of photon energy lower than that of the electronic level being excited. These centers are designated herein as A centers. One preferred procedure for referencing the signals from these centers is to incorporate in the same medium other luminescent centers, designated herein as B centers, the absorption coefficient and luminescence efficiency of which are approximately independent of temperature within the temperature range being measured, when excited with light of the same wavelength $\lambda_v$ as the A centers, and the luminescence of which is emitted in a spectral region different from that of the A centers. If one divides the luminescence intensity emitted by the A centers by the luminescence intensity emitted by the B centers, the ratio so obtained is a unique function of temperature. This referencing technique is discussed further hereinafter in connection with continuous, distributed temperature sensors using a single long, unbroken temperature-sensing optical fiber.

When using a non-crystalline sensor material, it is convenient to make it the core of an optical fiber segment, with an appropriate cladding around the core, for easy connection to an optical fiber waveguide.

If the A centers and the B centers have difference luminescence decay times, then one can determine the relative intensities of the luminescence emitted from the two kinds of centers by measuring the total luminescence decay time. For example, an yttrium aluminum garnet (YAG) crystal co-doped with $Nd^{3+}$ and $Yb^{3+}$ ions can be excited with light of wavelengths near 946 nm or any other wavelength at which the absorption by $Nd^{3+}$ is strongly temperature-dependent but the absorption by $Yb^{3+}$ is only minimally affected by temperature. The luminescence from $Nd^{3+}$ peaks at about 1064 nm, and that from $Yb^{3+}$ peaks at about 975 nm. The relative intensities of both luminescences can be measured by using spectrally selective optical filters and measuring separately the luminescence intensities at 975 and 1064 nm. A simpler way, which does not require optical filters, is to pulse the interrogating light and measure the decay time of the total luminescence from both $Nd^{3+}$ and $Yb^{3+}$. The luminescence decay time of $Yb^{3+}$ is several times longer than that of $Nd^{3+}$. Thus, as the temperature increases, the luminescence intensity from $Nd^{3+}$ increases relative to that from $Yb^{3+}$, and the decay time of the total luminescence decreases as a function of said relative intensities. Instead of a crystalline matrix, the $Nd^{3+}$ and $Yb^{3+}$ ions may be dissolved in a glass matrix. Except for the use of a glassy medium, the probe is operated in the same manner as described in the preceding paragraph.

An optical fiber temperature probe based on the measurement of a temperature-dependent light absorption measurement has an advantage over other optical probes in that it measures the average temperature over the length of the fiber probe. Thus, if one wishes to measure the average temperature over, for example, a pipe having different temperatures along its length, a long fiber temperature probe disposed over the whole length of the pipe will measure its average temperature. A preferred embodiment uses a luminescent probe with a temperature-dependent light absorption, the luminescence intensity of which follows approximately equation (4).

Fiber Optic Temperature Sensor Usable from the Cryogenic Region up to Over 850° C.

The teachings of section 2.1 can be used for constructing a fiber optic cryogenic thermometer usable from the liquid helium region up to over 850° C., using a single probe. One preferred embodiment uses as a probe a single crystal fiber of the well-known material Nd:YAG. The upper limit operation of the probe is determined by the temperature beyond which substantial quenching of the luminescence occurs, and this is higher than 850° C. for Nd:YAG. The principles of operation of the probe can be understood with reference to the physical model of FIG. 1, and equations (3)–(5). As follows from the discussion in section 2.1, the magnitude of the energy gap $E_v$, and hence of the Boltzmann factor $\exp(-E_v/kT)$ for any temperature range, can be chosen simply by controlling the wavelength $\lambda_v$ of the excitation light. Each temperature range of operation has an optimum range of $E_v$ magnitudes. The requirements are usually a moderate absorption coefficient to the excitation light, typically corresponding to a value of $\alpha$ between 0.02 and 0.20, combined with a temperature coefficient of a preferably greater than 0.01 per kelvin. The optimum magnitudes of $E_v$ thus increase with increasing temperature. Suppose that one desires a temperature coefficient of about 0.015 or greater per kelvin at ambient or lower temperatures. According to equation (5) the coefficient is equal to $(E_v/kT^2)$. From this one obtains magnitudes for $E_v$ of about 910 cm$^{-1}$ at the ambient temperature of 295 K (22° C.) and 130 cm$^{-1}$ at 112 K, the boiling point of liquefied natural gas (LNG).

At temperatures higher than 600 K, practical temperature coefficients of α are lower. For example, at 723 K (450° C.) a temperature coefficient of 0.015 would require an $E_v$ of 7,841 cm$^{-1}$, corresponding to a Boltzmann factor of about 1.7×10$^{-7}$ and, hence, to a negligible value of α. Temperature coefficients of a few tenths of 1 percent are practical, though, which are compatible with temperature accuracies of about 1 percent.

The Measurement of Cryogenic Temperatures

Conditions are more favorable at cryogenic temperatures. For example, a comfortable Boltzmann factor of 0.05 at 10 K, corresponding to a magnitude of $E_v$ of about 20.8 cm, gives a temperature coefficient of α of about 30 percent per Kelvin, which should make it possible to measure temperature changes smaller than 0.01 K.

One important need in cryogenic thermometry, especially near 4.2 K, is the measurement of temperatures in the presence of high magnetic fields generated by superconducting magnets. Electrical thermometers are usually unsuitable for this purpose, as their performance is affected by the magnetic field. Very high magnetic fields, of the order of 1 tesla or greater, can also affect optical probes like Nd:YAG, by changing the position of either the $E_s$ or that of the $E_v$ level. But the effect of these changes, if any, can be cancelled out by carrying out the measurements at two slightly different wavelengths $\lambda_{v1}$ and $\lambda_{v2}$ of the interrogating light corresponding to $E_v$ values of $E_{v1}$ and $E_{v2}$ respectively, for instance by tuning the laser wavelength of an inexpensive AlGaAs diode laser. Any specific wavelength difference $\Delta\lambda_v$ corresponds to a specific difference $\Delta E_v$ independent of the effect of the magnetic field on the individual magnitudes of $E_{v1}$ and/or $E_{v2}$. The temperature T will then be determined from the relation $$T = \Delta E_v / k \cdot \ln(I_2/I_1) \qquad 0$$

where $I_1$ and $I_2$ are the luminescence intensities generated by the interrogating light wavelengths $\lambda_1$ and $\lambda_2$, respectively.

2.2 A Distributed Temperature Sensing System

The advantages of the temperature sensing of this invention, discussed in the preceding section, can best be appreciated by its adaptability to measure temperatures in a multiplicity of locations simultaneously, with the probes at each location being part of a series array of sensors along a fiber-guided light path. Such an application requires accurate measurements of small changes in the intensity of the light propagating along the array, as the multiplexing of many light-absorbing probes along a single light path requires that each probe absorb only a relatively small fraction of the intensity of the interrogating light. One suitable embodiment uses individual probes, conveniently in the form of optical fibers, spliced at different locations into a long optical fiber guide. A logical extension of this concept is to dope the whole continuous length of a long fiber with the light-absorbing luminescence converter. Such an embodiment is a preferred one when the number of sites to be monitored is large, or when checking for hot spots along a continuous path, for example along the windings of a large electrical transformer. As described above, one can measure small optical absorptions directly by converting the fraction of the intensity of the light which is absorbed into luminescence or Raman emission.

A general optical time-domain reflectometry method and apparatus for sensing magnitudes (values) of a physical parameter at different sensing points along an optical fiber pathway using wavelength conversion techniques was described by applicant in the parent application Ser. No. 711,062 (now U.S. Pat. No. 5,004,913), in the sections entitled "1. A long Continuous Optical Fiber Sensitive to Perturbations Along its Whole Length" and "J. The Use of Luminescence in Time Division Multiplexed Systems" (U.S. Pat. No. 5,004,913, col. 26 line 62 to col. 29 line 48), the teachings of which are incorporated herein. The "Time Division Multiplexed Systems", illustrated in FIGS. 21 and 22 of said patent are generally known to those of ordinary skill as optical time-domain reflectometry (OTDR) devices. Their application to the measurement of distributed temperatures is described here.

If one uses as a light-absorbing material a fluorescent dye with a fluorescence decay time of the order of nanoseconds (characteristic of most fluorescent dyes), then one can use OTDR techniques for converting any light absorbed at any point along the fiber length into a fluorescence light intensity free of the baseline background of the interrogating light. If, for example, a resolvable fiber segment length absorbs one percent of the interrogating light intensity at 300 K, and the temperature coefficient of the absorption is 1.2 percent per kelvin, the fluorescence intensity will change by 1.2% per kelvin, while the intensity of the transmitted light, as measured by Rayleigh backscattering, will change by only about one part per 10,000.

In a practical embodiment one must be able to measure both the temperature and the location of any hot or cold spot. Location information can be obtained by standard OTDR techniques, from the time of arrival of the fluorescence light pulses at the electro-optic unit, relative to the time of launching of the interrogating light pulse into the fiber. The following relation holds:

$$d = 0.5 \, tc/n$$

where
 d is the fiber distance from the electrooptical unit (where the interrogating light pulses were launched);
 t is the time of arrival of the fluorescence light pulses;
 c is the velocity of light in a vacuum; and
 n is the index of refraction of the glass of the fiber core.

The temperature of the fiber at any distance d from the electrooptic unit is determined from the intensity of the fluorescence pulse.

The spatial resolution of the measuring system is determined by the risetime and duration of the interrogating light pulses, and by the fluorescence decay time of the fluorescent material. With fluorescence pulses with a duration of 10 nanoseconds one can obtain spatial resolutions of about 1 meter or better.

Two alternate embodiments are described below:

In the first embodiment, applicable when the fiber length does not exceed about 100 meters, the fiber consists of a plastic core having the fluorescent dye dissolved therein, and a plastic cladding with an index of refraction lower than that of the core, but with a temperature coefficient of said index of refraction similar to that of the core. Only minute concentrations of the dye are needed, so there is a large number of efficient fluorescent dyes available, including dyes II and R6 G subject of FIG. 2. Since virtually all plastic-soluble fluorescent dyes can be used for the practice of the invention, it is convenient to use those which can be interrogated with light from inexpensive LED's or laser diodes, and which have good stability. Dyes of the violanthrone (dibenzanthrone) family, including Vat Green 1, have these characteristics.

For accurate measurements it is necessary to provide a reference signal. The intensity of the Rayleigh-backscattered light can be used for this purpose. The ratio of the intensity of the dye fluorescence to that of the Rayleigh-backscattered light provide a reliable indication of the temperature at each resolvable fiber length.

If longer lengths of the temperature-sensing fiber are needed, the second embodiment is preferable. In this case one uses an optical fiber having a core made of low-attenuation glass, for instance pure silica, and the fluorescent dye is dissolved in a transparent plastic cladding. The index of refection of the plastic cladding is lower than that of the core, and excitation of the dye fluorescence is accomplished by evanescent wave coupling. Since the light paths of both the interrogating light and the fluorescence light are through low-attenuation glass, light signals can be collected over much longer distances than possible from an all-plastic fiber. Signal referencing can be obtained by co-dissolving in the plastic cladding a second fluorescent dye the absorption coefficient and fluorescence efficiency of which are essentially invariant over the temperature range to be measured. The relative fluorescence intensities from the two dyes uniquely define the temperature of the fiber at the measured location. The second fluorescent dye (the reference dye) can be chosen from any fluorescent dye soluble in the plastic cladding and having a fluorescent level with an energy no higher than the photon energy of the interrogating light.

Figure 4:
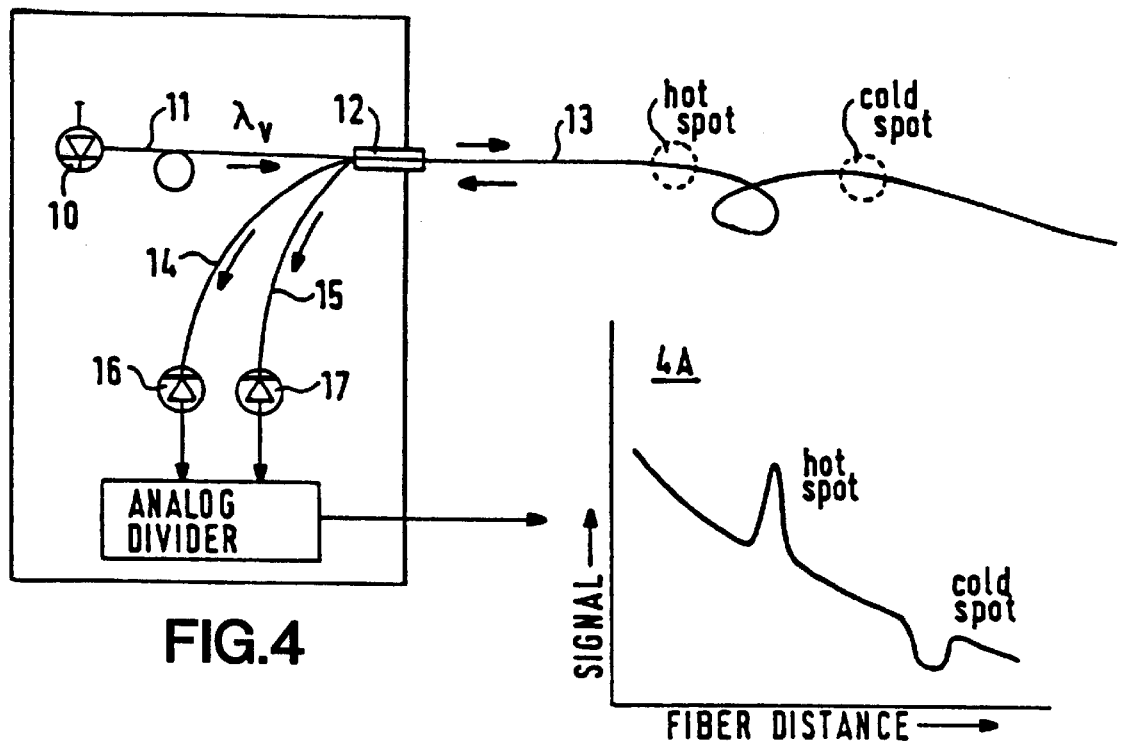
FIG. 4 illustrates a distributed optical thermometer according to this invention.

A suitable embodiment of a device (essentially an optical time-domain reflectometer with an added fluorescence channel) for performing distributed temperature measurements with either of the above fiber embodiments is shown schematically in FIG. 4. The light source 10 is driven to produce interrogating light pulses with a duration of about 10 to 30 nanoseconds and a wavelength $\lambda_v$. These light pulses are injected into the fiber segment 11 and, through the optical fiber coupler 12, into the temperature-sensing fiber 13. At any point along the fiber, each interrogating light pulse produces a fluorescence light pulse with an intensity determined by the temperature at that point, and a reference pulse at a different wavelength from that temperature-dependent pulse. In the case of the plastic fiber the reference pulse is the intensity of the Rayleigh-backscattered light. In the case of the fiber with the glass core and fluorescent plastic cladding, the reference pulse is the fluorescence light pulse produced by the co-dissolved second fluorescent dye, this dye having a temperature-independent optical absorption coefficient at the wavelength of the interrogating light. Both the temperature-dependent light pulses and the reference pulses are transmitted by the optical fiber to the electro-optical unit and, through optical coupler 12 and fiber segments 14 and 15, to photodetectors 16 and 17. The photodetectors are made spectrally selective, one to the temperature-dependant optical pulses, and the other to the reference pulses, by means of narrow band-pass optical filters applied to their windows. The time of arrival at the photodetectors of the optical pulses generated at any point along the fiber, relative to the time of generation of the interrogating light pulse at the light source, defines the location along the fiber where the optical pulses are generated. The ratio of the photoelectric signal from the fluorescence generated by the temperature-dependent absorption to the reference signal is an indicator of the temperature at that point along the fiber. When such ratio is recorded as a function of the fiber distance from the fiber tip into which the interrogating light pulses are launched the above-background temperatures appear as peaks, and the below-background temperatures appear as depressions in graph 4A.

Figure 5:
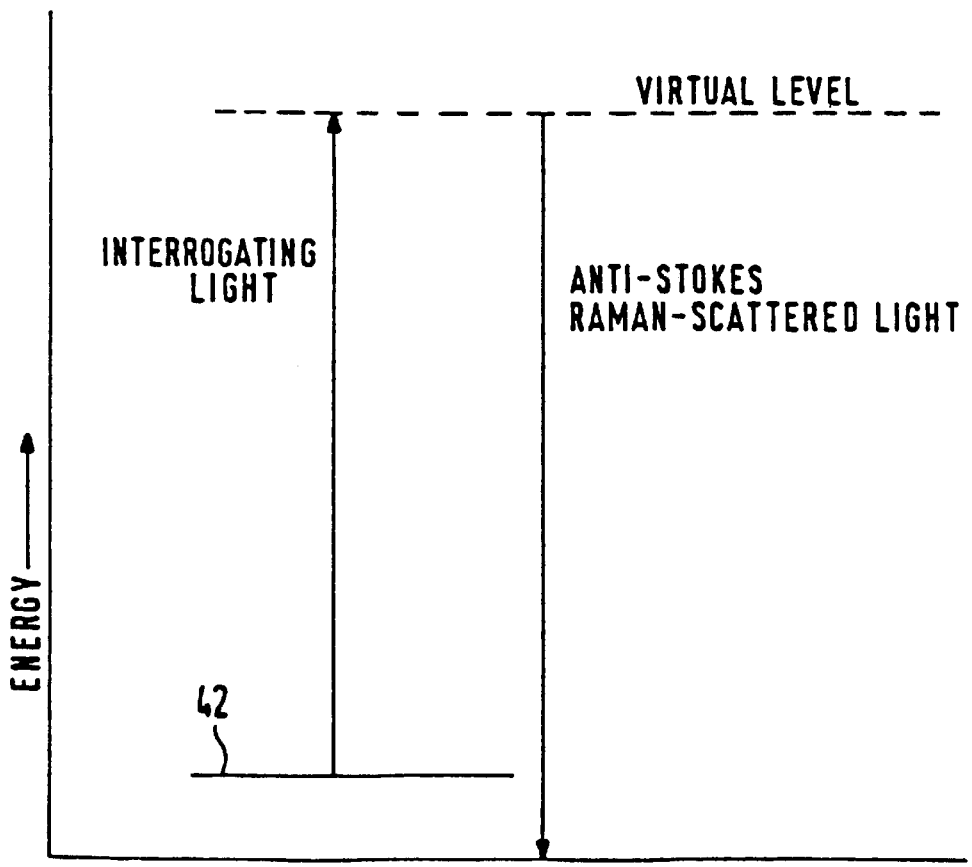
FIG. 5 illustrates the principles of anti-stokes Raman thermometry.

2.3 The Measurement of Temperature Distributions by Anti-Stokes Raman Scattering The preceding sections described how one can use a material for measuring temperature, by causing it to convert a temperature-dependent fraction $\alpha_v$ of the intensity of illuminating light of pre-selected wavelength $\lambda_v$ into light emitted at a wavelength different from $\lambda_v$. The above cited anti-Stokes Raman technique by Dakin et. al., *Electron. Lett.* 21, 569 (1985), can be regarded as a special case of this general technique. It also uses a temperature-dependent excitation of molecules occupying thermally populated vibronic levels, except that the optical excitation is to a virtual energy level rather than to an actual one. The process is illustrated by FIG. 5. As in the case of luminescent vibronic materials, the occupancy number $N_{42}$ is determined by the Boltzmann factor $\exp(-E_v/kT)$. The above equations (2) and (5) are also approximately obeyed. But the fraction $\alpha_v$ of the interrogating light which can be emitted as Raman-scattered light is usually orders or magnitude lower 3.0 Distributed Sensing of Physical Variables by Light Redistribution Between Two Light-Guiding Regions of an Optical Fiber Probe If an optical fiber has two light-guiding regions, and a physical variable can cause measurable, variable redistribution of interrogating light between these regions, then one can use such a fiber as a sensing probe for the physical variable. If, additionally, such light redistribution at any sensing point along the fiber does not affect significantly the relative light distribution at other sensing points, then the fiber probe can be used as a distributed sensor. It is shown below how one can measure distributed temperatures and other physical variables using this principle.

Figure 6:
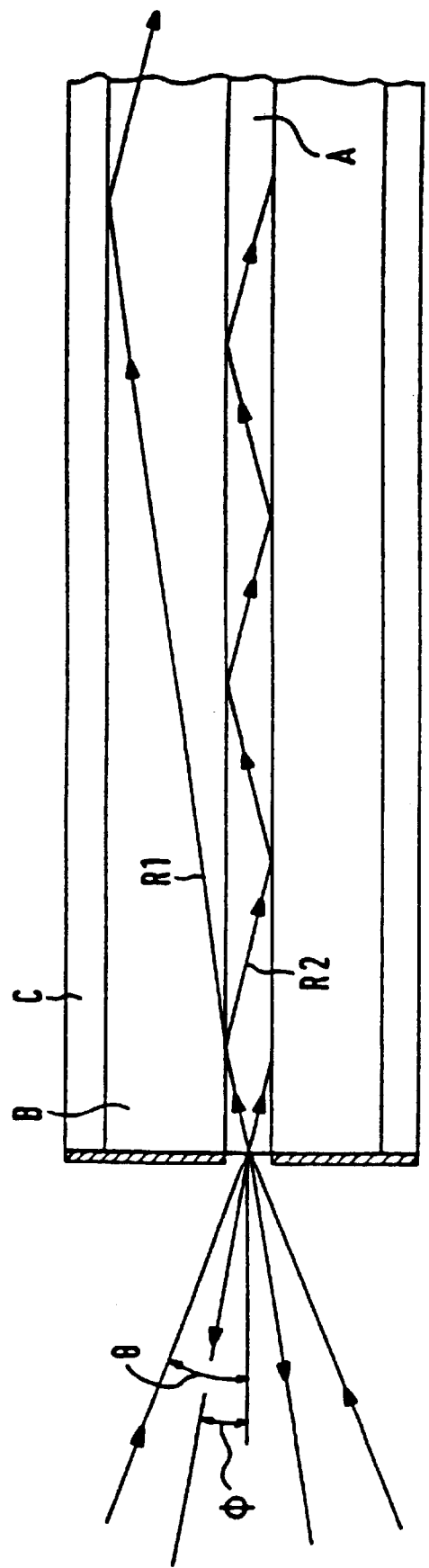
FIG. 6 illustrates another optical fiber probe for the measurement of distributed temperatures, having a central core with a temperature-dependent numerical aperture.

3.1. An Alternate Method for Measuring Distributed Temperatures with a Single Unbroken Optical Fiber Probe Another method for measuring distributed temperatures according to this invention uses a temperature-dependent light distribution between two light-guiding regions of an optical fiber. One of the preferred embodiments uses a fiber shown schematically in FIG. 6. It comprises a glass core A (the first light-guiding region) with an index of refraction $n_1$, a first cladding B (the second light-guiding region), having a temperature-dependent index of refraction $n_2$ lower than $n_1$, and a second cladding C around the first cladding, having an index of refraction $n_3$ lower than $n_2$. The launch end of the fiber is aluminized on the face of the two claddings, so that the interrogating light can be launched only through core A. The interrogating light is launched as a recurrent train of short pulses with a duration of the order of a few nanoseconds (ns) or shorter, depending on the spatial resolution desired (approximately 10 ns per meter), over an acceptance angle $\theta$ for meridional rays necessary to fill the numerical aperture $(NA)_2$ defined as $$(NA)_2 = (n_2^2 - n_3^2)^{1/2}$$

In other words, the interrogating light fills both light-guiding regions A and B. The value of $n_2$ decreases in a known manner with an increase in temperature, at a much greater rate than the decrease in the value of $n_1$, and the intensity distribution of the interrogating light pulses between regions A and B will be determined by the relative values of the squares of $(NA)_2$ and the numerical aperture $(NA)_1$ of core A, defined as $$(NA)_1 = (n_1^2 - n_2^2)^{1/2}$$

The value of $(NA)_2$ can be kept approximately constant over the working temperature range by making cladding C out of a material such that its index of refraction $n_3$ has essentially the same temperature coefficient as the index of refraction $n_2$ of cladding B.

Now, the intensity of the light Rayleigh-backscattered from the core A at any resolvable segment of the fiber, corrected for the intrinsic light attenuation of the fiber per unit length, will be a known function of the temperature of the segment. In contrast to prior art methods of temperature measurement using a temperature-dependent index of refraction, cross-talk between different sensing points is minimized by virtue of the fact that light rays deflected out of core A through a temperature change are not 'thrown away' as in the prior art, but captured and returned to the region comprising core A and first cladding B, thus restoring a temperature-dependent light distribution at every segment of the fiber.

Since the cladding faces of the fiber are aluminized (or otherwise made opaque), and the diameter of cladding B can be made much larger than that of core A, the intensity of the Rayleigh-backscattered light collected at the core launch end from any resolvable segment of the fiber will be proportional to the intensity of the interrogating light propagating within the core at that segment, determined by the value of $(NA)_1$ and, hence, by the temperature-dependent value of $n_2$. Any contribution from cladding B to the collected Rayleigh-backscattered light can be further minimized by using a small collection angle $\phi$ consistent with the needed signal intensity.

The sensitivity and performance of the proposed distributed sensor may be anticipated from the following assumed conditions:

The sensing fiber comprises a core A made of silica glass with an index of refraction $n_1$ of 1.45800, an elastomeric silicone cladding B with an index of refraction $n_2$ of 1.45030 at the temperature of 300 K, and a second silicone cladding C with an index of refraction $n_3$ at 300 K of 1.41900. Both $n_2$ and $n_3$ have a temperature coefficient of $2\times10^{-4}$ per kelvin. Then a change of 1 kelvin from 300 K to 301 K will increase the value of $(NA)_1^2$, and hence of the intensity of the Rayleigh-backscattered light, by 2.6 percent, a rather large change compared to prior art fiberoptic temperature-sensing systems.

The spatial resolution of the system depends on the risetime and/or duration of the interrogating light pulses. Using an optical time domain reflectometer (OTDR) and light pulses with a duration of 100 picoseconds (ps), for example, one could obtain a spatial resolution of the order of 10 cm, limited by time dispersion effects in the fiber.

Another embodiment of these sensors uses fibers wherein both claddings, as well as the core, are made of glass, with the first cladding having an index of refraction with a temperature coefficient different from that of the core. While glass has lower temperature coefficients for its index of refraction than plastics, the change may be sufficient for a number of applications, especially at high temperatures at which a plastic cladding would degrade.

In another embodiment, one uses an optical fiber as described above and having the additional property that the light scattering coefficient of the central core is knowingly and substantially different from that of the first plastic cladding. In that case the intensity of the backscattered light pulses generated and captured within the region comprising both the core and the first cladding, and back-directed to the fiber launch end, is measured by ordinary OTDR techniques. The intensity of the backscatter pulses generated at each sensing point, relative to the intensity of the forward interrogating light pulses, is then an indicator of the fiber temperature at that point.

For example, assume a fiber wherein the plastic claddings have a temperature coefficient of $n_2$ of $3\times10^{-4} \cdot deg^{-1}$, and a light scattering coefficient 5 times greater than that of the glass core. Assume that at a temperature $T_0=300$ K, the index of refraction $n_1$ of the glass core is equal to 1.4600, while that of the first cladding, $n_2$, is equal to 1.4400. Then, $(NA)_{12}=0.2408$. Now, if the temperature is increased by 50° C., $n_2$ will decrease to 1.4250, the magnitude of $(NA)_{12}$ will increase to 0.3178, and the intensity of the interrogating light propagating within the first cladding will decrease to 57.4% of its original value, while the light propagating along the central core will increase by about 74 percent. If at 300 K the intensity of the interrogating light was distributed equally between the glass core and the first plastic cladding, then the total backscatter intensity at 350 K will be decreased to about 77% of its intensity at 300 K.

In yet another embodiment, suitable for measuring temperatures lower than ambient, the fiber probe has a glass core and two concentric plastic claddings as described above, except that the second cladding C has dissolved therein a relatively low concentration of a fluorescent dye. The interrogating light is launched into the glass core only, so as to fill its numerical aperture $(NA)_1$. A temperature decrease at any point along the fiber will increase the index of refraction $n_2$ of the first cladding B. This will decrease the value of $(NA)_1$, causing a fraction of the intensity of the interrogating light to be deflected from the core to the first cladding B and the boundary between the first and second cladding, where it generates a fluorescent signal the intensity of which relative to that of the interrogating light is a unique function of temperature. The dye concentration in cladding C is pre-selected so that a small fraction only of the intensity of the interrogating light deflected out of the core is absorbed by the fluorescent cladding. Thus, as the interrogating light pulses continue their propagation along the fiber beyond the cold spot, most of the intensity of the deflected light will re-enter the fiber core and will be available for interrogating the rest of the fiber.

A temperature sensing fiber probe as described in the preceding paragraph is particularly useful for detecting leaks of cryogenic fluids, for example liquefied hydrocarbons in petrochemical installations, or rocket fluids during rocket launchings.

3.2. The Measurement of Distributed Forces with a Single Unbroken Fiber Probe

Mechanical forces acting on an optical fiber, especially microbending forces, usually cause an attenuation of light being transmitted through the fiber core, by deflecting a fraction of the intensity of this light out of the core and into the fiber cladding. If such forces are acting on a plurality of points on a long fiber, or at a single but unknown location on it, they can usually be measured by Optical Time Domain Reflectometry (the abbreviation OTDR is used herein both for the method and for the device used for implementing it). The method consists of launching interrogating light pulses with a duration typically of the order of nanoseconds (ns) into the fiber core, and measuring the intensity of the Rayleigh-backscattered light pulses as a function of fiber distance from the fiber tip at which the interrogating light pulses were launched. Any force on the fiber which causes an attenuation of the intensity of the interrogating light pulses (for instance a microbending force) is revealed as a discontinuity in the backscatter intensity versus distance decay curve. The time of arrival of the Rayleigh-backscattered pulses, relative to the time of launching of the interrogating light pulses, defines the location along the fiber where the force is acting, and the intensity of the backscattered pulses indicates the magnitude of the force.

A serious shortcoming of this method is that it 'throws away' the deflected light to be measured, and instead estimates its magnitude indirectly from a difference between two usually much larger, but still weak and noisy backscatter signals. Rayleigh scattering is an inefficient process, producing intensities at the photo-detector which are typically 50 or more dB down from the forward interrogating light intensity at any 1 meter length of fiber. These indirect measurements are, then, plagued by a relatively large amount of baseline noise.

The teachings of this invention provide a method and associated devices for the measurement of force distributions on optical fibers, as well as temperature distributions. The method and devices of this invention are capable of producing, in the measurement of forces, signals stronger by orders of magnitude than those obtainable from Rayleigh-backscatter measurements, for the same extent of optical attenuation and with the same intensity of the interrogating light. The method consists of converting the fraction of the intensity of the interrogating light which has been deflected into the fiber cladding into a signal separable from the interrogating light transmitted through the fiber core. This separation can be achieved either in the optical wavelength domain, by luminescence or Raman conversion, or in the time domain, as illustrated in the following embodiments.

1st Embodiment

Figure 7:
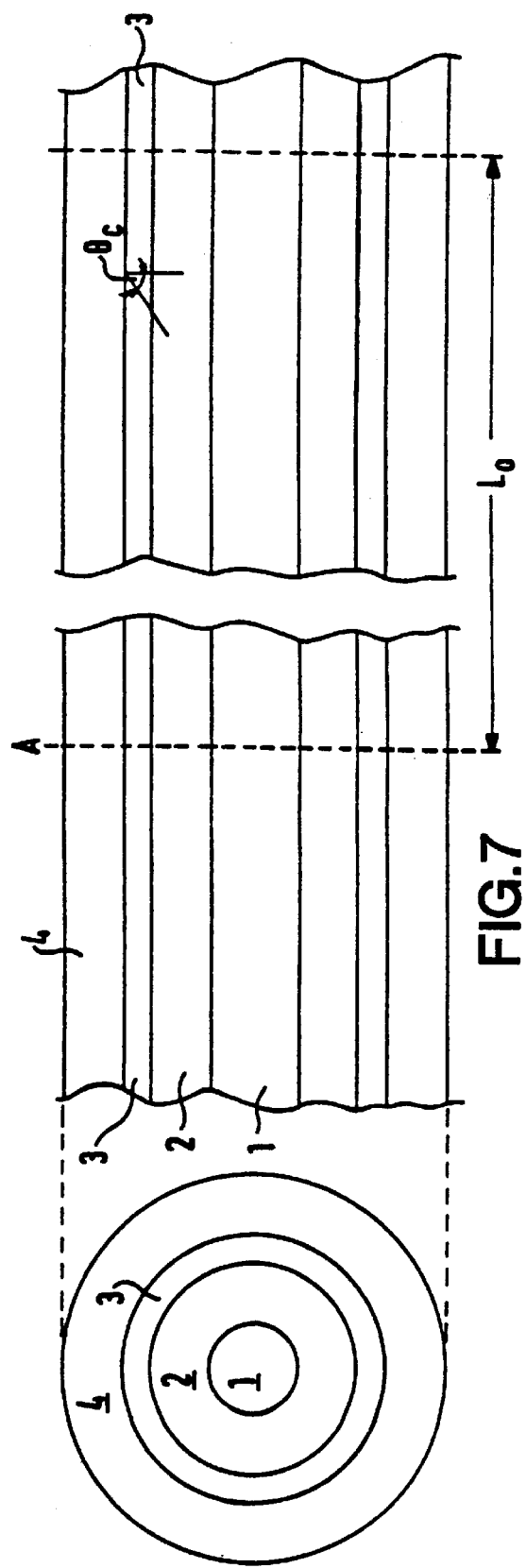
FIGS. 7 and 8 describe two optical fibers useful for practicing this invention, having a luminescent cladding.

This embodiment uses a fiber shown schematically in FIG. 7, consisting of a glass core 1 with an index of refraction $n_1$ and a cladding 2 with an index of refraction $n_2$ lower than $n_1$. Around cladding 2 there is a second cladding, concentric layer 3, containing fluorescent centers absent in either the core or incladding 2 and having a luminescence decay time of the order of nanoseconds, this cladding having an index of refraction $n_3$ not lower than $n_2$ and a thickness of a few micrometers. Around cladding 3 there is a third cladding 4 with an index of refraction $n_4$ substantially lower than $n_3$. Interrogating light pulses with a duration of the order of nanoseconds, having wavelengths within the absorption band of the fluorescent centers, are launched into the core 1 of the fiber, where they propagate along the fiber axis with a small attenuation caused by residual optical absorption with a coefficient $\epsilon$ and, usually to a larger extent, by Rayleigh light scattering with a coefficient $\beta$. At a point A along the fiber, the launched interrogating light pulses have an intensity $P_o$. After this point, and for a length L corresponding to the time resolution of the OTDR, the light intensity is attenuated by a fraction $a_t$. The power $P_s$ of the Rayleigh-backscattered light pulses generated within the fiber segment of length L within the fiber numerical aperture $(NA)_s$ and sent to the photodetection station is given approximately by $$(P_s/P_o) \approx \tfrac{1}{2} a_t [\beta/(\beta+\Theta)]\cdot[(NA)^2_s/4n^2_1] f_t \text{ watts} \qquad (6)$$

where the terms within the second square brackets define the fraction of the power of the scattered light captured within the solid acceptance angle of the fiber core, and $f_t$ is the fraction of the power of this captured light which is transmitted by the fiber along the optical path to the photodetector. The numerical aperture $(NA)_s$ is given by $$(NA)_s = (n^2_1 - n^2_2)^{1/2} \qquad (7)$$

An external force operating on this fiber segment and capable of producing a localized strain or any other microbending force will deflect a fraction $\alpha_s$ of the power $P_o$ of the interrogating light propagating along the fiber core at that point into cladding 2, due either to fiber microbending or to the increase of the index of refraction $n_2$ of the glass cladding relative to that of the core, the value of $\alpha_2$ being determined by the magnitude of the force. Then $P_s$ will be decreased by this fraction, and the change $\Delta P_s$ (the signal) will be given by the relation $$\Delta P_s = d_s P_s \text{ watts}$$

It should be noted that the optical processes described above involve only core 1 and cladding 2 and are, therefore, unaffected by layer 3 or cladding 4.

Let us now look at what happens to the light forced out of the glass core 1 and into cladding 2. For this purpose, we must treat the fiber at having a second numerical aperture $(NA)_f$, for the generated fluorescence, defined as $$(NA)_f = (n^2_2 - n^2_4)^{1/2} \qquad (8)$$

Light entering cladding 2 at angles within $(NA)_f$ will be trapped and propagated along the fiber axis by total internal reflection from cladding 4 but, after a number of reflections determined by the absorption coefficient and concentration of the fluorescent centers in layer 3, will be absorbed by these centers and converted into fluorescence with a quantum efficiency $\phi$. The fluorescence will usually be emitted at longer wavelengths than those of the absorbed interrogating light. The fraction $P_f$ of the power of this fluorescence light which reaches the photodetector is given approximately by $$P_f \approx \tfrac{1}{2} \alpha_s P_o \phi [(NA)^2_f / 4n^2_2] f'_t (\lambda_s/\lambda_f) \text{ watts} \qquad (9)$$

where
$f'_t$ is the fraction of the fluorescence power generated within $(NA)_f$ which is transmitted by the fiber along the optical path to the photodetector;
$\lambda_s$ is the wavelength of the interrogating light; and
$\lambda_f$ is the mean wavelength of the fluorescence light.

Let us now assume some typical values for some of the parameters in equations (6) and (9), for a fiber segment one meter long:

$$a_t = 2.3 \times 10^{-3} \qquad (NA)_f = 0.40$$
$$[\beta/(\beta+\epsilon)] = 0.80 \qquad n_1 = 1.500$$
$$\phi = 0.70 \qquad n_2 = 1.487$$
$$f'_t/f_t = 0.70 \qquad (\lambda_s/\lambda_f) = 0.90$$
$$(NA)_s = 0.20$$

Stress or microbending forces which attenuate the intensity of the interrogating light by not more than a few percent will deflect into cladding 2 only optical rays within the numerical aperture $(NA)_f$ of the fiber, especially in view of the high value of $(NA)_f$ relative to $(NA)_s$. Thus, equation (9) applies, and one can determine from the above values of the relevant parameters that $$P_f/\Delta P_s \approx 975$$

Fluorescence conversion of light forced out of the core of an optical fiber by stress or other forces can, thus, produce signals orders of magnitude stronger than those obtained from the decrease of the Rayleigh-backscattered light produced by the same forces. As a consequence of this, distributed sensing systems can be designed so that each sensing point attenuates a small fraction only of the intensity of the interrogating light propagating along the fiber at that point, thus allowing a given intensity of the interrogating light launched into the sensing fiber to interrogate, and produce strong signals from, a much greater number of sensing points than would be practical with a system based on Rayleigh-backscattered signals.

The above-described fluorescent claddings can be applied to maximize diagnostic information from various types of fibers', including multimode step index, graded index and single mode fibers. In the latter case, of course, only the interrogating light beam is single mode. Cladding 3 can be, for example, a clear plastic doped with an organic fluorescent dye.

Second Embodiment

In the second embodiment the light formed out of the fiber core by a stress or microbending force is converted into Raman-scattered light at a wavelength different from $\lambda_s$. This requires a different fiber from that used in the first embodiment. The fiber consists of the same or similar glass core 1 as in FIG. 6. Around this core is a glass cladding having a relatively high Raman-scattering coefficient, for example a silica glass doped with a high concentration of phosphorous pentoxide, $P_2O_5$, as Raman-active material. It is important that the fiber core co not contain the Raman-active material present in the cladding. Also, the cladding volume per unit length should preferably be greater than the core volume. Light forced out of the core and into the cladding is converted into Raman-scattered light. Generally, the Raman conversion process is less efficient than fluorescence conversion, so that the signal strengths are smaller than possible with fluorescence conversion, at least for fiber lengths of the order of a few meters.

Third Embodiment

The third embodiment is advantageous when the fluorescent material is an organic dye, and the dye can be dissolved in a transparent plastic cladding having an index of refraction substantially lower then $n_2$, the index of the glass cladding of FIG. 7. This will become apparent from the following discussion.

Even the clearest plastics attenuate light by at least an order of magnitude more than the best fiber-grade glass. It is because of this fact that that the fluorescent layer 3 was specified to be only a few micrometers thick. If the diameter of cladding 2 is, for instance, 125 micrometers (a common value), then only a small fraction of the optical path of the fluorescence light is through a high loss material. But there is a better and simpler way to achieve this objective, as described below.

Fluorescence Conversion by Evanescent Wave Coupling

Figure 8:
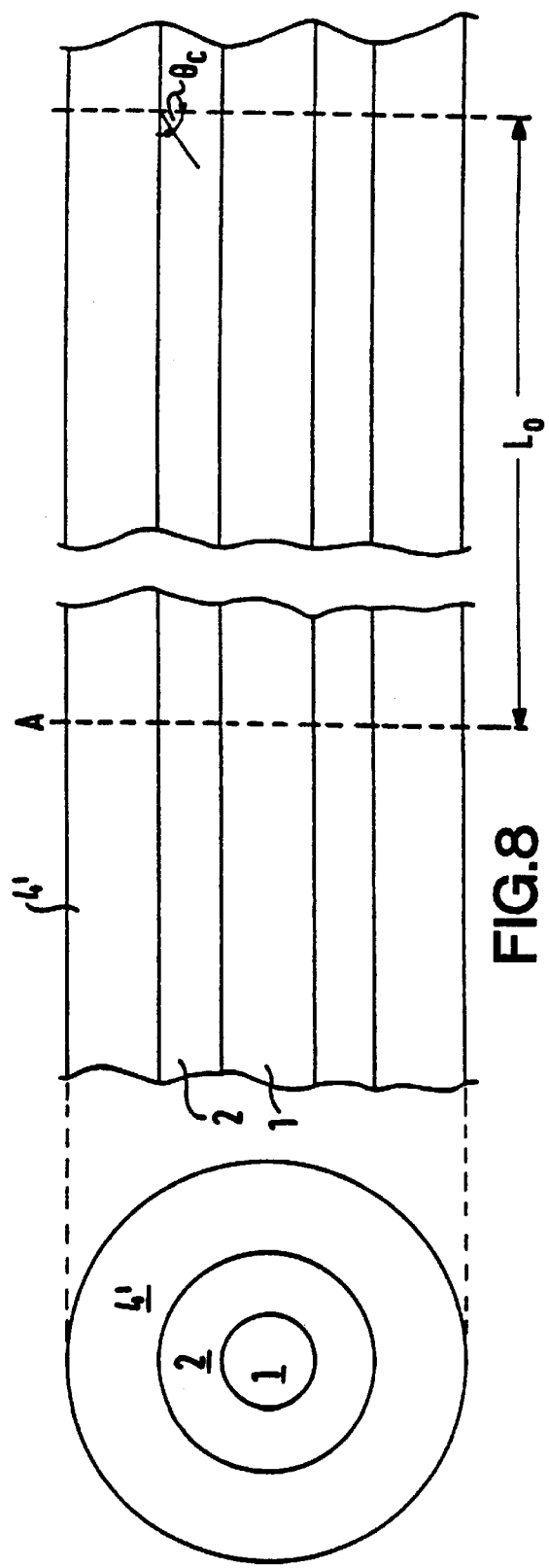

The force-sensing fiber of this embodiment is illustrated in FIG. 8. It comprises the same core and the same cladding 2 of FIG. 7. Around cladding 2 there is a second cladding, coating 4', made of a transparent plastic and having dissolved therein a fluorescent dye characterized by a high quantum efficiency, an absorption band in a spectral region comprising the wavelength of the interrogating light, $\lambda_s$, and a fluorescence decay time of the order of $10^{-8}$ seconds or shorter. The plastic has an index of refraction $n_p$ low enough to produce a numerical aperture $(NA)_{fp}$ higher than 0.3, and preferably higher than 0.4, $(NA)_{fp}$ being defined by the relation $$(NA)_{fp}=(n^2_2-n^2_p)^{1/2} \quad (10)$$

Light entering cladding 2 from core 1 at angles greater than the critical angle $\theta_c$ for total internal reflection from coating 4' will enter this cladding at least to a depth $d_p$ known as the thickness of the evanescent layer, and defined as the depth over which the electrical field amplitude of the light waves decays to the value 1/e of its value at the interface between cladding 2 and coating 4'. The value of $d_p$ is given by the relation $$d_p=(\lambda_e/n_7)/2\pi[\sin^2\theta-(n_p/n_2)^2]^{1/2}\text{cm} \quad (11)$$

where $\theta$ is the angle of incidence of the light rays on the interface between cladding 2 and layer 4' (this layer can legitimately be regarded as a second cladding). Only a small fraction of the intensity of the incident light will be absorbed per reflection but, by a proper choice of the concentration of the fluorescent dye, virtually the entire intensity of the light leaving the core at angles greater than $\theta_c$ can be absorbed over the length L of the resolvable fiber segment. The generated fluorescence can be collected by the optical fiber with high efficiency, because the angular distribution of the fluorescence will favor the modes within the acceptance angle of the fiber (Lee et. al., *Appl. Opt.* 18, 862 (1979)).

3.3 A Practical Device for Measuring Distributed Forces

Distributed forces can be measured with the same electro-optical arrangement as that described with reference to FIG. 4, with the sensing fiber 13' being either one of the fibers illustrated in FIGS. 7 or 8. The light source 10 is driven to produce interrogating light pulses of submicrosecond duration and wavelength $\lambda_s$ within an optical absorption band of the fluorescent centers (fluorescent molecules or ions) in the applicable cladding. These light pulses are launched into the core of the sensing fiber, where they propagate along the fiber length. At any point along the fiber on which a mechanical force is acting, a fraction $\alpha$ of the intensity of the interrogating light pulses is deflected out of the core and into cladding 2, and is immediately converted into fluorescence light pulse by the fluorescent centers in the applicable cladding (cladding 3 if the fiber of FIG. 7 is used, or the evanescent layer of cladding 4' in the fiber of FIG. 8). Both the fluorescence light pulses and the Rayleigh-backscattered light pulses (from the fiber core) travel back to the electro-optical unit and, through the fiber optic coupler 12 and fiber segments 14 and 15, to photodetectors 16 and 17, which are made spectrally selective to the force-dependent fluorescence pulses and the Rayleigh-backscattered pulses, respectively. The ratio of the photo-electric signals from the two photodetectors is an indicator of the value of $\alpha$ and, hence, of the magnitude of the force. The time of arrival of the optical pulses at the photodectors, relative to the time of launching of the interrogating light pulses, identifies the location of the force. The fluorescence light pulses are easily separable from the Rayleigh-backscattered pulses because of their different, generally longer, wavelengths.

Suitable Dyes and Cladding Materials for the Practice of This Invention

In principle, any fluorescent dye dissolved in a clear cladding can be used in a force- or temperature-sensing fiber according to the teachings of this invention. In practice, the choice of dye to be incorporated in the cladding would be determined by factors including the fiber length, dye properties including fluorescence efficiency, photo-chemical and thermal stability, and solubility in the cladding material. It should be clear to those of ordinary skill that the dye concentration should be not lower than that needed to generate an easily measurable signal over the length of the spatially resolvable fiber segment, of the order of 1 meter for interrogating light pulses with a duration of $10^{-8}$ seconds, and shorter for shorter light pulses. For fibers of length of several hundred meters or longer it is preferred to use dyes with absorption and fluorescence bands in the orange, red or near infrared regions, to avoid the high scattering losses which occur at shorter wavelengths. Dyes of the violanthrone family have been mentioned above (section 2.1) and have also been mentioned in the parent application Ser. No. 711,062 filed Mar. 12, 1985, now U.S. Pat. No. 5,004,913 as suitable for use in force-sensing fibers with a fluorescent cladding. Depending, inter alia, on the length of the fiber probe, preferred dye concentrations range from about $10^{14}$ to about $10^{18}$ molecules/cm$^3$.

Regarding cladding materials in which to dissolve the fluorescent dye, any material from which plastic optical fibers are presently made are suitable. Examples include but are not limited to polyurethanes, polyacrylates (including methacrylates) and styrenic polymers. One can also dissolve fluorescent dyes in inorganic glasses without having to use temperatures high enough to degrade the dyes, by using the well-known 'sol gel' process, and the resulting dye-doped glasses can be used as fluorescent claddings.

3.4 Force Sensing Fiber Probes and Techniques Not Requiring Wavelength Conversion One such fiber probe includes a central core A having an index of refraction $n_1$, a first cladding B having an index of refraction $n_2$ lower than $n_1$ and a light scattering coefficient much higher than that of the core, and a second cladding C around and in contact with cladding B and having an index of refraction $n_3$ lower than $n_2$. The thickness of cladding B is not much greater than about 15 μm, with a cross-sectional area comparable to that of the core. In operation, interrogating light pulses of submicrosecond duration are launched into the core. Under the action of a force at any point along the fiber, a fraction of the intensity of each interrogating light pulse is deflected into cladding B, wherein it generates pulses of backscattered light. Because cladding B has a much higher light scattering coefficient than the core, forces acting on the fiber at any point along its length will increase the intensity of the total intensity of the light backscattered from that point. This increase can be measured by ordinary OTDR techniques. Because of the relatively small thickness of cladding B, at least a large fraction of the intensity of the light deflected into this cladding will re-enter the core as core-guided modes, especially with interrogating light wavelengths longer than 1.0 μm.

3.5. The Measurement of Forces with Optical Fiber Probes Having Two Light-guiding Regions of Different Effective Optical Path Length In the embodiments of force-sensing systems discussed above, I have described how light deflected out of the core of an optical fiber under the action of a force can be processed into an optical signal separable from the light transmitted by the fiber core. In the above embodiments, signal separation is effected by converting the deflected light into spectrally separable light of different wavelengths from those of the interrogating light. Separation can also be effected in the time domain, by processing the pulsed or AC-modulated light deflected out of the core into a light having different temporal characteristics from those of the interrogating light carried by the fiber core, without the need for wavelength conversion. A preferred embodiment of such a technique is described in the following paragraphs, with reference to FIGS. 9 and 9A.

Figure 9:
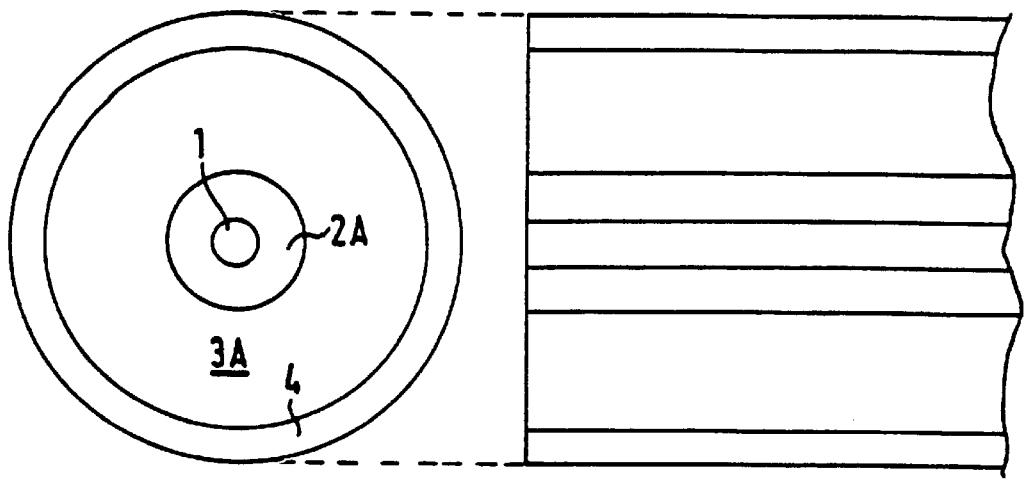
FIGS. 9, 9A and 9B illustrate an arrangement for the measurement of distributed forces using optical fibers having two light-guiding regions of different effective optical path length.

The optical fiber 13A shown schematically in FIG. 9 comprises a single mode core 1 with an index of refraction $n_1$, a first cladding 2A around the core having an index of refraction $n_2$ such that the value of $(n^2_1 - n^2_2)^{1/2}$ does not exceed 0.15, a light-guiding region 3A around cladding 2A, having a graded parabolic or near parabolic index of refraction the peak value of which, $n_3$, is several percent higher than $n_1$, and an outer cladding 4A with an index of refraction $n_4$ lower than $n_2$. The fiber is used as a distributed force-sensing probe with a device represented schematically in FIG. 9A.

Figure 9A:
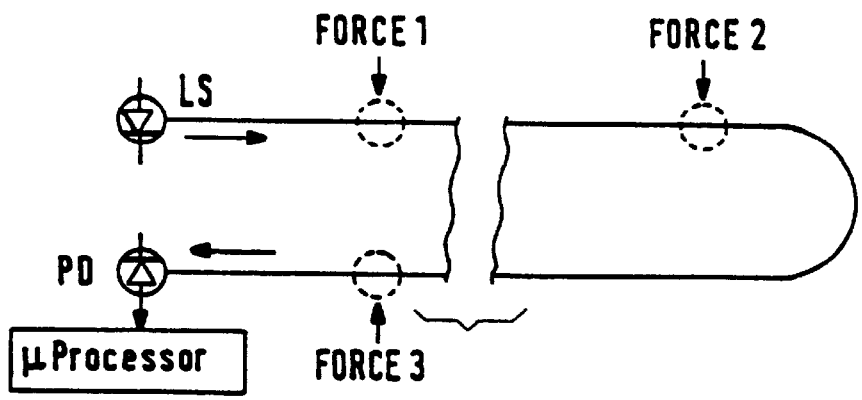

Referring to FIG. 9A, light source LS launches into the fiber core a train of interrogating light pulses with a duration of the order of $10^{-9}$ seconds or shorter, depending on the spatial resolution desired. At any point where a material force is acting on the fiber, a small fraction of the intensity of each interrogating light pulse is deflected out of the fiber core into light-guiding region 3A, where it is trapped by the graded refractive index distribution of this region and by the outer cladding 4A. Because $n_3$ is substantially higher than $n_1$, the effective optical path length of region 3A, (that is, its actual length multiplied by its index of refraction) is substantially longer than that of the core 1, so that the light deflected out of the core into region 3A arrives at the photodetector 16A at the distal fiber end after a resolvable interval t following the arrival of the interrogating light pulses carried by the fiber core. This interval identifies the location at which the deflection occurred, according to the relation $$t = (z/c)(n_3 - n_1) \text{ seconds} \quad (12)$$

where z is the fiber distance to the photodetector of the point where the the force was acting; and c is the velocity of light in a vacuum.

For example, if $n_3$ is equal to 1.553 and $n_1$ is equal to 1.46, then two sensing points one meter apart along the fiber will produce signals arriving at the photodetector about $3.1 \times 10^{-10}$ seconds apart, assuming that the duration of the interrogating light pulse is not longer, and that region 3A does not introduce a serious pulse broadening. Since the light-guiding region 3A has a parabolic or near parabolic index profile, the broadening can be shown to be relatively low for some practical fiber lengths. The rms pulse broadening Δt is given approximately by the relation $$\Delta t \approx [(n_3 - n_1)/n_3]^2 [n_3 z / 20 . c . 3^{1/2}] \text{ seconds} \quad (13)$$

For a z distance of 100 meters and the above assumed values for $n_3$ and $n_1$, Δt is approximately equal to $5.4 \times 10^{-11}$ seconds. The actual dispersion may be somewhat greater because of some dispersion in the first cladding 2A, but spatial resolutions of the order of 1 meter should be obtainable in fiber lengths of about 100 meters. If numerous forces are acting at different locations along the fiber, their signals will arrive at the photodetector at different resolvable times. The intensities of the time-resolved signals will be indicators of the magnitude of the forces.

Figure 9B:
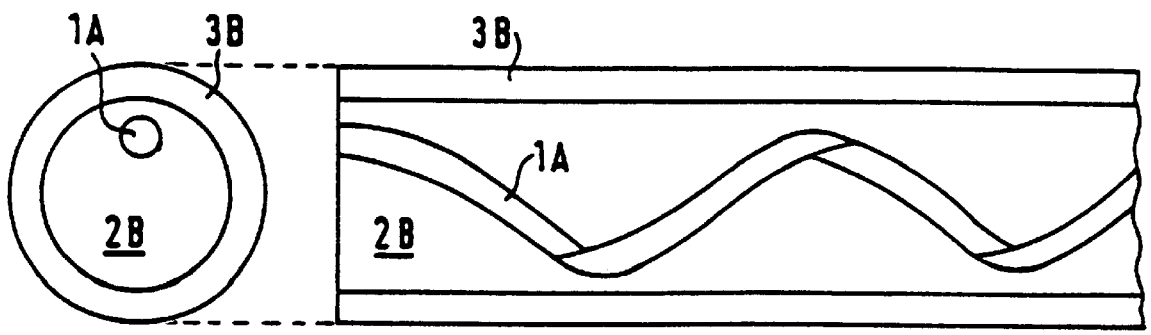

Another embodiment of a fiber with two light-guiding regions of different optical path length consist of a fiber wherein one of the two light-guiding regions has an actual path length different, for the same unit length of the fiber, from that of the other light-guiding regions. As example of such embodiment is a fiber as shown schematically in FIG. 9B, having a helical core 1A with an index of refraction $n_1$, a first cladding 2B around said core, having an index of refraction $n_2$ lower than $n_1$, and a second cladding 3B around the first cladding, with an index of refraction $n_3$ lower than $n_2$. When light pulses with a duration of $10^{-9}$ seconds or shorter are launched into the core of this fiber, and a lateral force deflects a fraction of the intensity of this light into cladding 2B, the cladding light pulses arrive at the photodetector before the light pulses propagated by the core. The interval t' between the core pulses and the cladding pulses follows the relation $$t'=(z/c)(n_1C-n_2) \text{ seconds} \tag{14}$$

where C is the ratio of the actual optical path length of the helical core to that of cladding 2B. Another embodiment uses a straight core and a helical cladding around the core.

Optical fibers having a helical light-guiding region tend to lose light at points other than those at which the forces to be measured are acting, so they are suitable for use in lengths not exceeding about 100 meters. For short fiber lengths, fibers with a helical light-guiding region have the advantage of better spatial resolution than fibers with both light-guiding regions straight, for the same duration of the interrogating light pulses.

Figure 10:
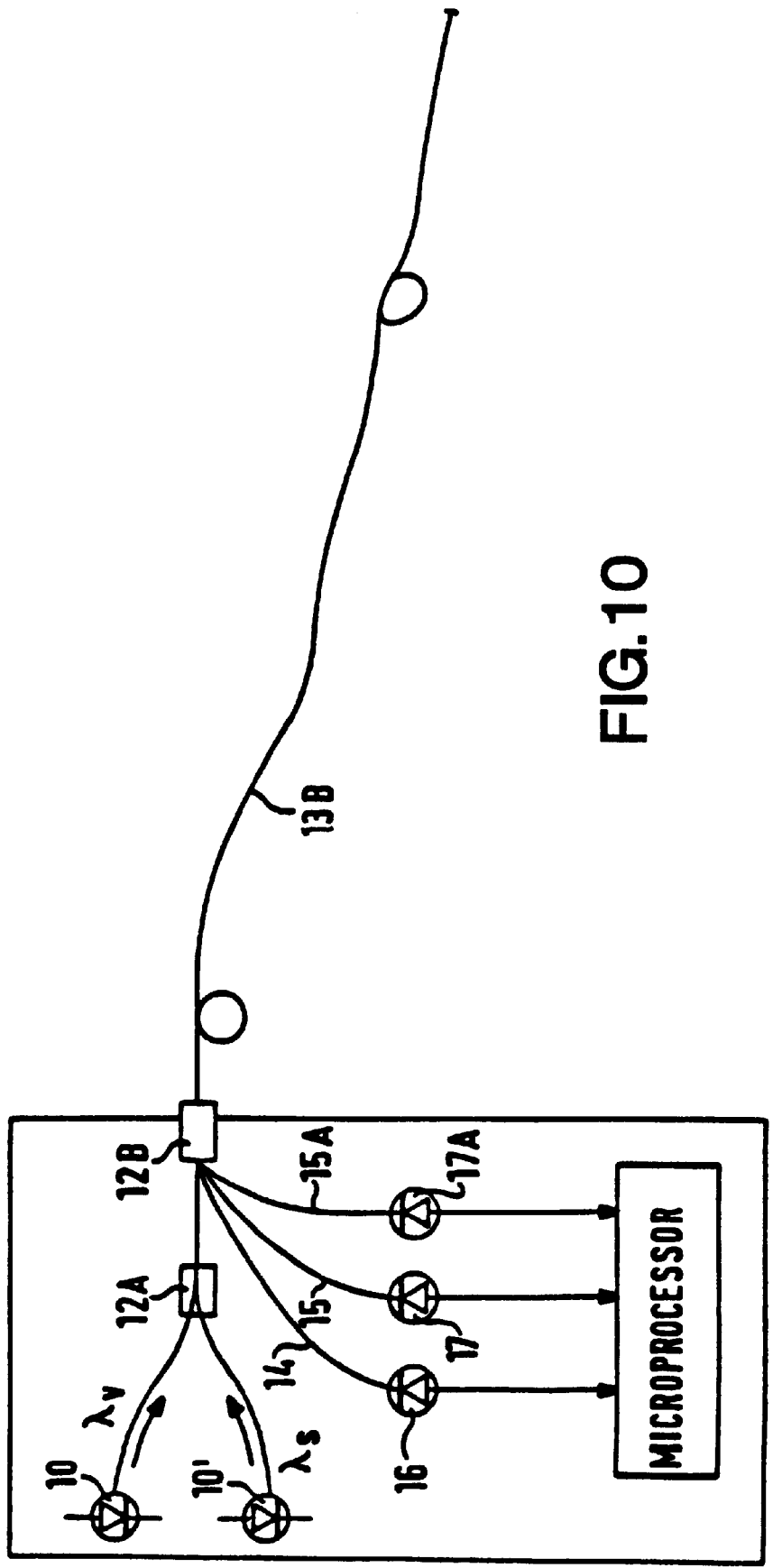
FIG. 10 represents a device for measuring distributed forces and temperatures according to this invention, using a single continuous optical fiber probe.

4.0. The Measurement of Distributed Forces and Temperatures on a Single Unbroken Optical Fiber The fibers illustrated in FIGS. 7 and 8 can be used for measuring both forces and temperatures independently of each other, not only on the same fiber, but also on the same location on the fiber. A preferred embodiment of an OTDR device for carrying out such measurements is illustrated in FIG. 10. The sensing fiber 13B is the fiber of FIG. 8, except that cladding 4' has two dyes dissolved in it, A and B, only one of which, dye A, has a temperature-dependent absorption coefficient when interrogated with light of wavelength $\lambda_v$. Dye B is used as reference as taught in section 2.1.1. Temperature distributions are probed by launching short interrogating light pulses of pre-selected wavelength $\lambda_v$ from light source 10A, through fiber optic couplers 12A and 12B, into both the core 1 and the first cladding 2 of the sensing fiber, and the temperature distributions are determined as already described (with reference to FIG. 4). Force distributions are probed by injecting, into the core 1 only of the sensing fiber, similarly short interrogating light pulses (with a duration of, for example, 10 to 30 nanoseconds, depending on the fiber length resolution desired) of pre-selected wavelength $\lambda_s$ corresponding to a photon energy not lower than the energy $E_s$ of the lowest vibrational sublevel of the emissive length of dye A, at which light absorption is much stronger than at the wavelength $\lambda_v$ and is essentially independent of temperature over the temperature range of operation. Any cladding modes of the $\lambda_s$ light injected at the launch end of the sensing fiber will be essentially 'stripped' by dye A in cladding 4', because of its much higher absorption coefficient for for light of this wavelength than for $\lambda_v$ light. The intensity of the fluorescence pulses generated at any point along the fiber by the force-probing pulses will then indicate the magnitude of the force on the fiber at that point, essentially independent of temperature. Photodetector 16 receives the fluorescence signals from dye A generated, alternately, by the $\lambda_s$ force-probing pulses and the $\lambda_v$ temperature-probing pulses. Photodetectors 17 and 17A receive and measure, respectively, the Rayleigh-backscattered pulses for normalizing the force readings, and the dye B fluorescence pulses for normalizing the temperature readings.

Figure 11:
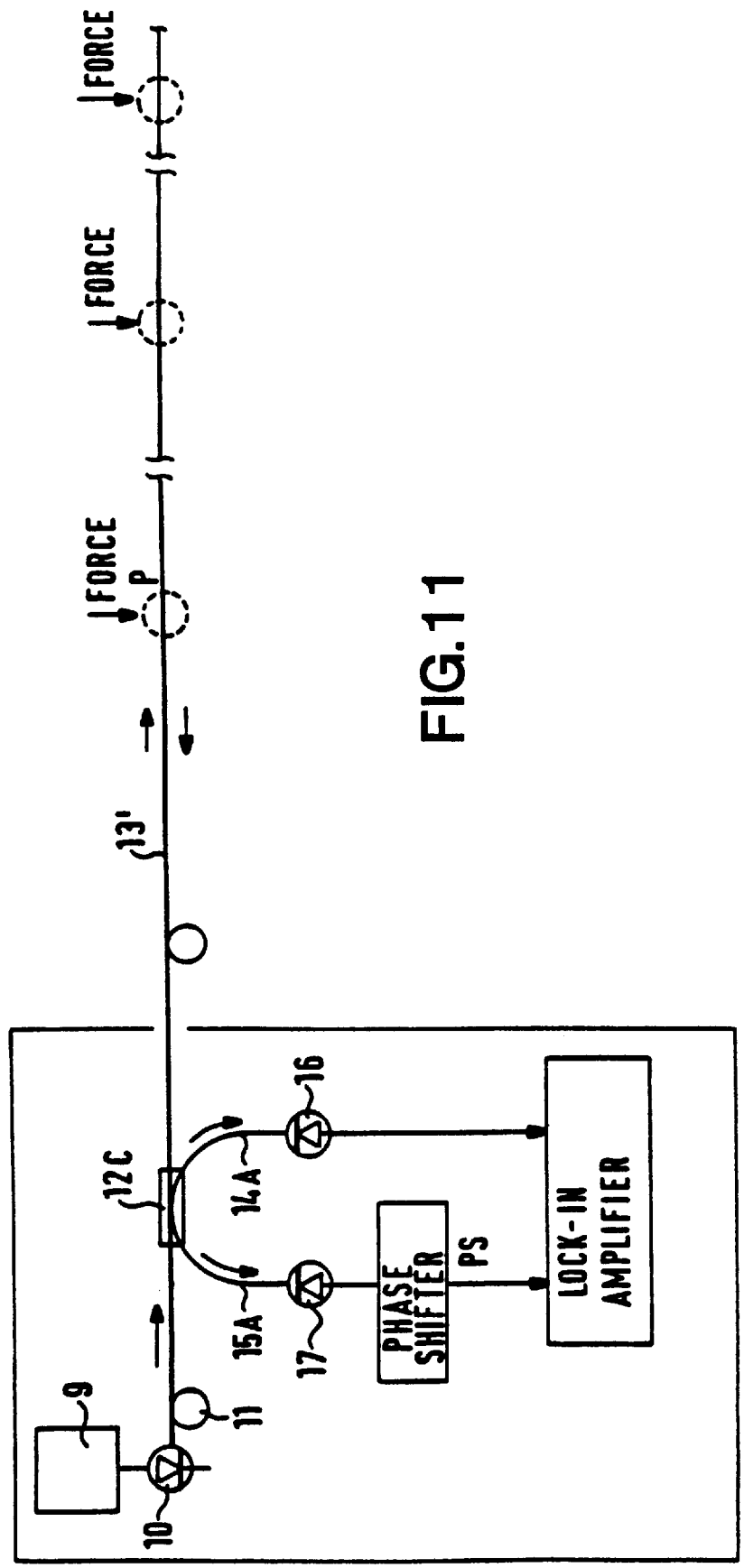
FIG. 11 shows a system for measuring distributed parameters on a single optical fiber using an AC-modulated C.W. light source, by phase angle division multiplexing.

5.0. The Measurement of Distributed Forces with an Optical Fiber Using an AC-Modulated C.W. Light Source The ability of the optical fibers of this invention to produce relatively large positive signals from forces and/or temperatures affords a simple alternative to conventional Optical Time Domain Reflectometry (OTDR), which does not require the use of very short light pulses for measuring the location and magnitude of these parameters. The alternative method is illustrated by FIG. 11. The light source 10, which could be an inexpensive light-emitting diode (LED), is driven by a crystal-controlled oscillator 9 at a frequency preferably not lower than 100 kHz, to generate a sinusoidally-modulated interrogating light which is launched through the fiber coupler 12C into the optical fiber 13'. This fiber can be either one of the optical fibers illustrated in FIGS. 7 and 8. A small fraction of the intensity of the interrogating light is diverted by coupler 12A and optical fiber segment 14A into photodetector 16. When the interrogating light beam reaches a point P along the fiber where a force is acting, a relatively small fraction α of the intensity of the interrogating light propagating along the fiber core is forced into the glass cladding, and is then converted into fluorescence light by the dye dissolved in the plastic coating. A fraction of the intensity of this fluorescence light travels back along the fiber to the fiber segment 15A and photodetector 17. The fluorescence light arriving at this photodetector has the same time-domain frequency f as that of the interrogating light, but has a phase shift relative to it, the magnitude of which depends on the fiber distance from point P to the electro-optical unit. Photodetector 17 receives, simultaneously, fluorescence light from other points along the fiber, with a phase shift different for each location. The phase angle Δθ (relative to the interrogating light) of the fluorescence light generated at any distance L' from the electro-optical unit is given approximately by the relation $$\Delta\theta=360 \, (2L'.f.n.c^{-1}) \text{ degrees} \tag{15}$$

where
n is the index of refraction of the glass, and
c is the velocity of light in a vacuum.

Now, one can apply a phase shift, by means of phase shifter PS, to the photo-electric signals produced by the group of fluorescence signals originating throughout the whole fiber length, so that the fluorescence originating at one location, (and only one location) produces a component of the photo-electric signal which is exactly in phase with the signal generated at photodetector 16. Now, if one varies the phase shift, for instance in the manner of a saw tooth ramp, one is effectively varying the location along the fiber where the generated fluorescence produces a photoelectric signal in phase with with the signal from photodetector 16. This component can be separated from the rest of the group of photoelectric signals by means of a lock-in amplifier controlled by the photoelectric signal from photodetector 16. By recording the output of the lock-in amplifier as a function of the applied phase shift one can, therefore, measure the magnitude of the forces acting on the fiber as a function of the fiber distance from the electro-optical unit.

Readers familiar with RADAR-ranging techniques may recognize the above method as an adaption of said techniques to the optical fiber systems of this invention.

The method is not restricted to fluorescent systems. Any system which produces distributed positive signals can be operated according to this phase shift method, including for example the force-sensing fiber shown schematically in FIG. 9, wherein the force signals carried by the region 3A are separated from the core light in the time domain.

6.0. Distributed Sensing Using Stimulated Light Amplification in Optical Fibers The distributed sensors described hereinbefore using plastic-soluble fluorescent dyes should be adequate for most applications where the sensor is not subjected for extended periods to temperatures in excess of 150 degrees Celsius. If higher thermal stabilities are required, then an all-inorganic sensing fiber would be desirable. One perceived drawback of inorganic glasses is that none are known which combine a high luminescence quantum efficiency with the submicrosecond luminescence decay times conventionally required with OTDR systems. One object of this invention is to provide a method and its associated devices for performing distributed sensing with glass fibers doped with rare earth ions, with fiber length resolutions of a few meters or less despite decay times of their spontaneous luminescence longer than $10^{-4}$ seconds. The method is illustrated in this section with trivalent neodymium [Nd(III)] as an example, but other glass dopants capable of stimulated emission should also be useful according to the teachings of this section.

Figure 12:
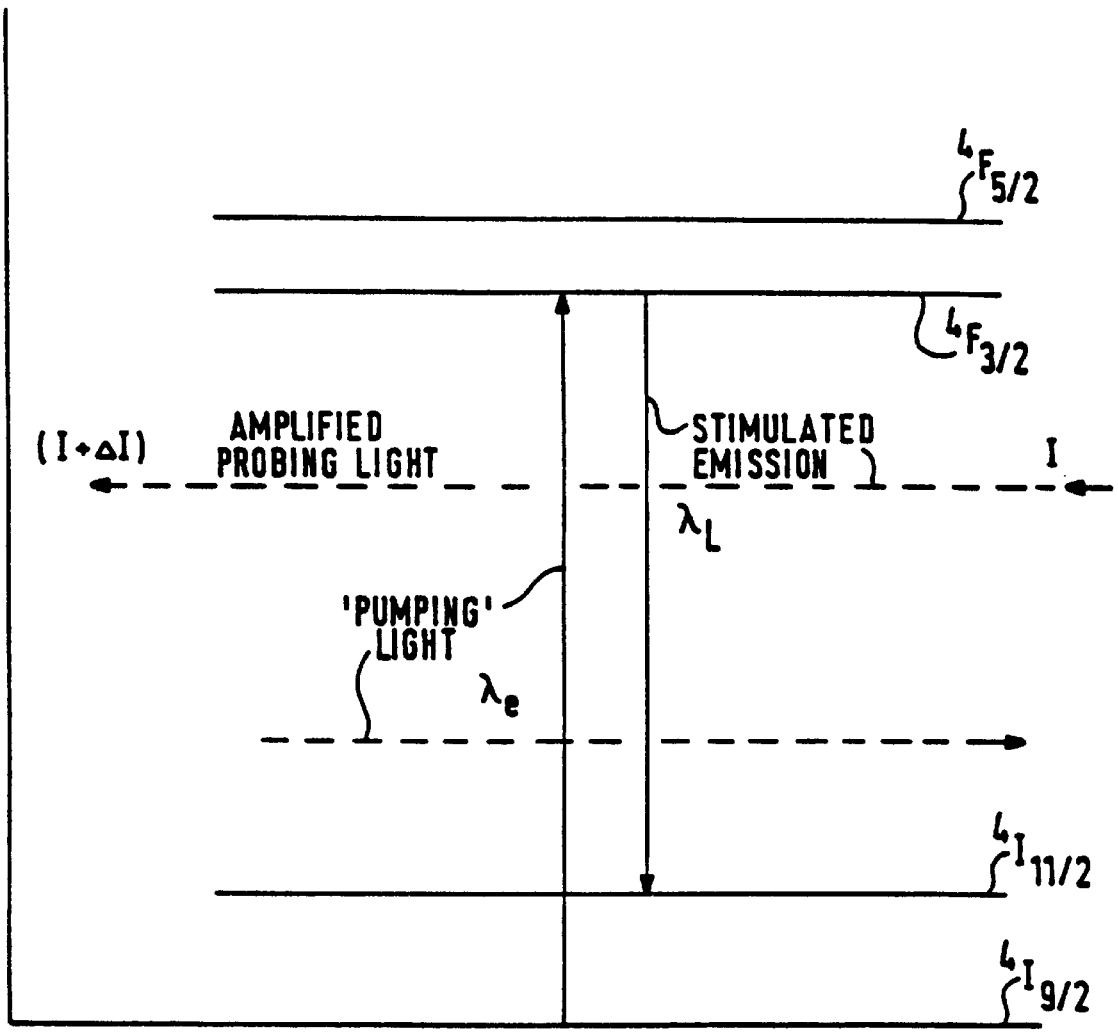
FIG. 12 illustrates the principles of distributed sensing with single long fibers using optical 'pumping' and amplification of counterpropagating light.

Nd(III)-doped glass has a high luminescence quantum efficiency, optical absorption bands in the 800–900 nanometer (nm) region (for which powerful laser diodes and LEDs are readily available), and luminescence bands from about 900 to 1330 nm. Additionally, it has an important property which compensates for its long luminescence decay time, namely the ability to generate stimulated emission from its excited $^4F_{3/2}$ level. If the optical excitation of Nd(III) is so intense that the occupancy number of this excited level exceeds the occupancy number of the lower level $^4I_{11/2}$ by a number $\Delta N$ (a condition known as population inversion), then light propagating through the system with a wavelength $\lambda_f$ equal to a laser wavelength $\lambda_L$ of Nd(III) and an intensity $I_o$ will be amplified to an intensity ($I_o+\Delta I$), the magnitude of ($\Delta I/I_o$) being determined at least in part by $\Delta N$. If the population inversion is achieved in a time of $10^{-7}$ seconds or shorter, then $\Delta I$ will reach a peak in a comparable period, regardless of the decay time of the spontaneous luminescence of Nd(III). The short response time permits the use of such a system for distance determination with an OTDR. The amplification process is illustrated by the model of FIG. 12. A 'pump' pulse of wavelength $\lambda_s$ within an optical absorption band of Nd(III) generates the population inversion, which amplifies light of wavelength $\lambda_L$ by stimulated emission. In this invention, the absorbed intensity of the pump pulse is determined by the value of the measurand (force or temperature). The use of fibers with cores of very small diameter (less than 10 micrometers) permits the production of the high excitation densities needed for population inversion with relatively low power laser sources, even when the laser power has to be shared by numerous multiplexed sensing points. Examples follow.

6.1. A Distributed Temperature Sensor Using a Nd(III)-doped Glass fiber

Figure 13:
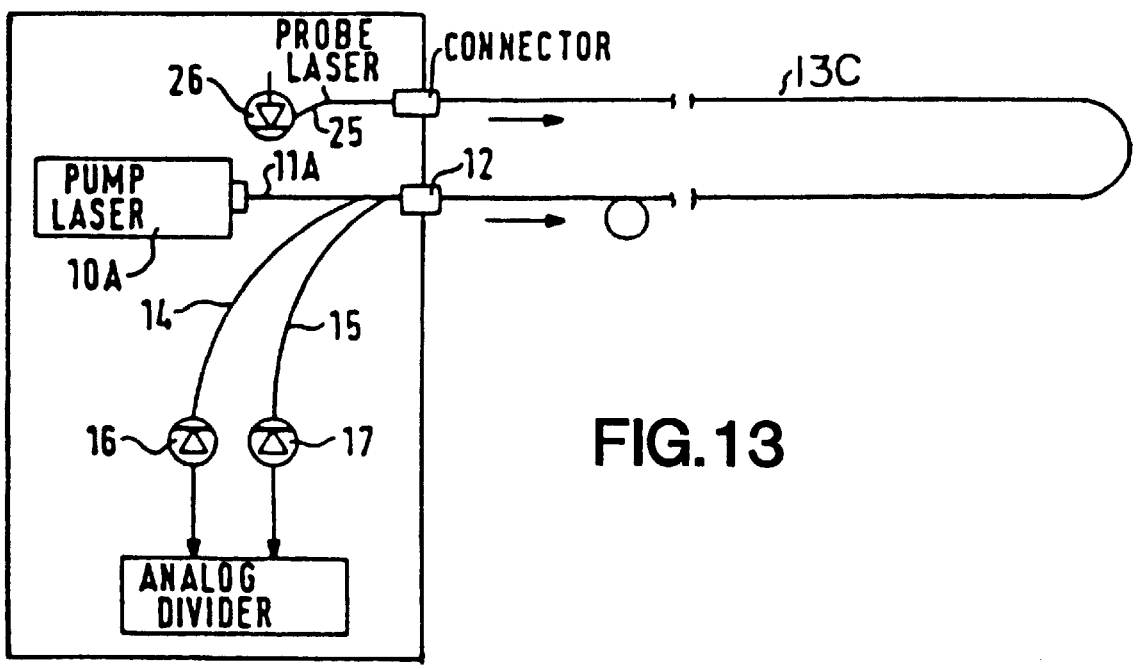
FIG. 13 shows a distributed thermometer using a Nd(III)-doped glass optical fiber.

A preferred embodiment is illustrated in FIG. 13. The 'pump' light source 10A is a pulsed laser emitting a beam of wavelength $\lambda_v$ outside the range of wavelengths which can be amplified by an inverted population of Nd(III) ions, and which is selectively absorbed by Nd(III) ions occupying a thermally excited level with an energy $E_v$ above the ground Nd(III) level. For measuring temperatures above about $-100°$ C. $\lambda_v$ can be selected between about 920 and 980 nm, corresponding to $E_v$ values between about 430 and 1030 cm$^{-1}$, depending on the composition of the base glass in which the Nd(III) ions are dissolved. The long sensing fiber 13C has a core made of Nd(III)-doped glass, with a diameter preferably not greater than 10 micrometers and a dopant concentration such that the optical density of the fiber at ordinary temperatures, over its whole length and at the wavelength of the interrogating (pump) light pulses, is between 0.1 and 0.3 (corresponding to attenuations between 1.0 and 3.0 dB), the fiber length chosen according to the particular application. The pump pulses, with a duration preselected according to the spatial resolution desired, and an energy preselected to generate population inversions along the fiber at temperatures within the range of interest, are launched into the fiber core, wherein a fraction $\alpha_v$ of their intensity is selectively absorbed by Nd(III) ions occupying the thermally excited level of energy $E_v$. The value of $\alpha_v$ is a function of temperature approximately according to equation (3) in section 2.1 above. The higher the value of $\alpha_v$, the greater the population inversion at the Nd(III) level $^4F_{3/2}$ relative to level $^4I_{11/2}$, and the greater the amplification of the intensity of the counterpropagating light of the laser wavelength $\lambda_L$ (FIG. 12).

For measuring temperature distributions one injects into the same fiber core, but at the distal end, a continuous, moderate power ($\gtrsim 25$ mW) laser beam from a Nd(III)-doped glass fiber laser 25 pumped by a laser diode 26. Fiber laser 25 has the same base glass composition as the long sensing fiber (except for a higher dopant concentration), so that its laser wavelength (near 1.08 micrometers) is essentially the same as that of the sensing fiber 13C. The latter is 'pumped' with a power high enough to produce stimulated emission. Now, as the temperature of any segment along the sensing fiber increases from an initial value of $T_1$ to $T_2$, the number of Nd(III) ions excited to the $^4F_{3/2}$ level increases from $N_1$ to $N_2$ approximately according to the relation $$N_2/N_1 = \exp[E_v(T_2-T_1)/kT_1T_2)]$$

when excited with pump pulses from laser 10A. When the number of Nd(III) ions in the excited $^4F_{3/2}$ level exceeds the number in the lower level $^4I_{11/2}$ (FIG. 12) the counterpropagating light from the fiber laser 25 is amplified. The intensity gained, $\Delta I$, will produce a pulsed signal arriving at the photodetector 16 in a time, relative to the time of launching of the excitation (pump) laser pulse, which is a known function of the location along the fiber from which the amplified pulse originated, and an intensity which defines the temperature of that fiber segment. In order to correct the signal for any fluctuations of the intensity of the interrogating light pulses, one can monitor the intensity of the Rayleigh-backscattered light from the same fiber segment with photodetector 17. Both photodetectors 16 and 17 are made spectrally selective to the amplified laser light and the Rayleigh-backscattered light, respectively, by means of narrow bandpass optical filters.

At temperatures lower than about $-100°$ C. one has to reduce the value of $E_v$. This is done simply by decreasing the wavelength of the interrogating (pump) light. It is preferably to use wavelengths which excite the $^4F_{5/2}$ level rather than the $^4F_{3/2}$ level, as this will avoid the use of excitation wavelengths which could be amplified in the same direction as that of the interrogating light pulses (which would effectively compete with the amplification of the counterpropagating light of wavelength $\lambda_L$). Depending on the temperature range being measured, one may select an interrogating light wavelength between about 810 and 840 nm. Instead of short excitation pulses, one may use AC-modulated AlGaAs laser light, and measure temperature as a function of fiber distance to the electro-optical unit by the phase angle division multiplexing method disclosed in section 5.0, with the added feature of the counterpropagating C.W. laser beam from the light source 25 in FIG. 13.

An important advantage of the use of light amplification in the submicrosecond time domain is that thermal quenching should not operate to a major extent even at temperatures of about 250° C. (and maybe even higher), provided that the quenching is due mainly to the shortening of the spontaneous luminescence decay time.

Figure 14:
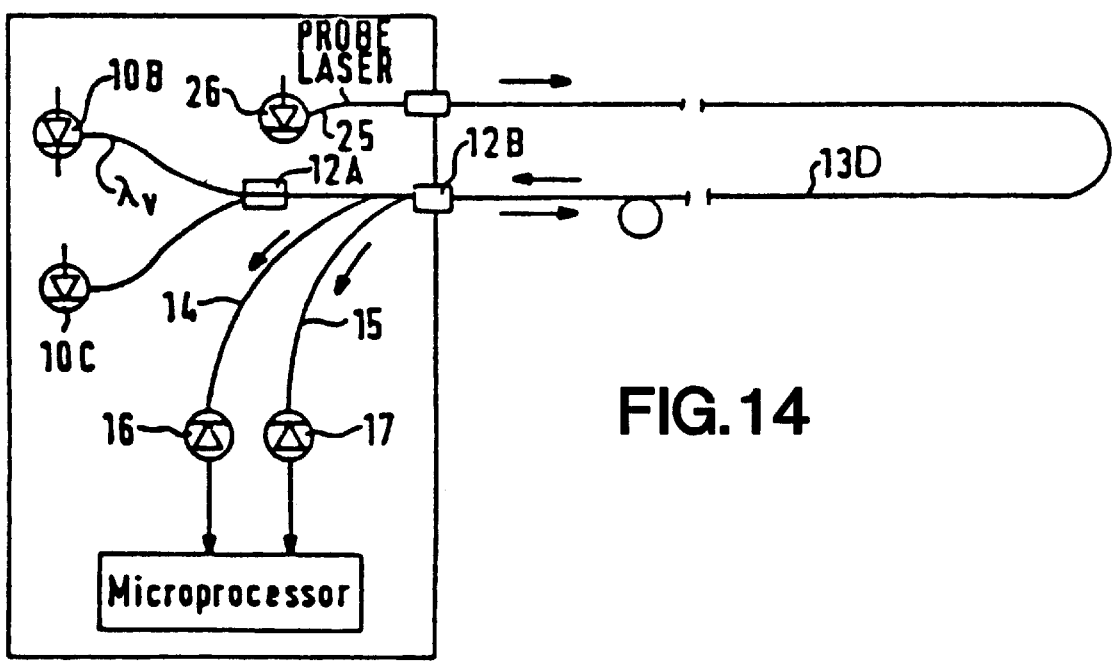
FIG. 14 illustrates a device for measuring distributed forces and temperatures with a single long optical fiber probe, using stimulated light amplification processes.

6.2. The Measurement of Both Force and Temperature Distributions on a Single Optical Fiber Probe An optical fiber having two light-guiding regions of different optical path length and a luminescent dopant in one of these regions can be used as a probe for measuring both distributed forces and distributed temperatures according to the teachings of this invention. An example of a preferred embodiment of a device for measuring these distributed parameters is shown schematically in FIG. 14. The fiber 13D differs from the fiber shown in FIG. 9A only in that the glass core is doped with $Nd^{3+}$ ions in a concentration sufficient to sustain a population inversion sufficiently high to produce amplification of a probing light beam of wavelength near 1.06 micrometers. Temperature measurement with this fiber is based on the principles set forth in sections 2.1 and 6.1 above. The light source 10A launches into one end of fiber 13D interrogating light pulses of pre-selected wavelength $\lambda_v$ between about 920 and 1000 nm, depending on the temperature range being measured, and with an energy sufficient to generate a temperature-dependent population inversion of the $^4F_{3/2}$ level of $Nd^{3+}$. At the other fiber end, a CW neodymium glass fiber laser 26 launches a CW probing laser beam of wavelength $\lambda_f$ of about 1.06 micrometers. As this probing light beam traverses a fiber segment containing a temperature-dependent population inversion, it will be pulse-amplified at that point. The time of arrival of the amplified light pulses at photodetector 16 identifies the location along the fiber where the pulse amplification took place, and the magnitude of the gain will be an indicator of the temperature of the segment.

Force distribution are measured according to the method described in section 3.2 above. The light source 10 launches into the core of optical fiber 130 at the end opposite to the one on which the interrogating light pulses of wavelength $\lambda_v$ were launched, a train of interrogating light pulses of a wavelength $\lambda$ at which the $Nd^{3+}$ ions are transparent. At any point along the fiber where a force is acting, a fraction $\alpha$ of the intensity of each pulse is deflected into the fiber cladding, which has an optical path length substantially longer than that of the core. The pulses of deflected light arrive at photodetector 16A after an interval $\Delta t$ following the arrival of the undeflected interrogating light pulses, the value of $\Delta t$ being determined approximately by equation (12) above, which defines the position along the fiber where the force was acting. The intensity of the deflected pulses is an indicator of the magnitude of the force. Ratiometric operation is achieved by dividing the electrical signals generated at photodetector 16A by those of photodetector 17 generated by the Rayleigh-backscattered light from the same point where the force was acting.

6.3. Other Arrangements for the Sensing of Distributed Forces and Temperatures Using Laser-Active Optical Fibers The sensing principles described above can be used for sensing forces and temperatures distributed over a multiplicity of locations, using a single laser-active optical fiber probe and one of the arrangements shown in FIGS. 13 and 14. The following are examples of suitable embodiments of optical fiber probes:

Embodiment 1

Figure 15:
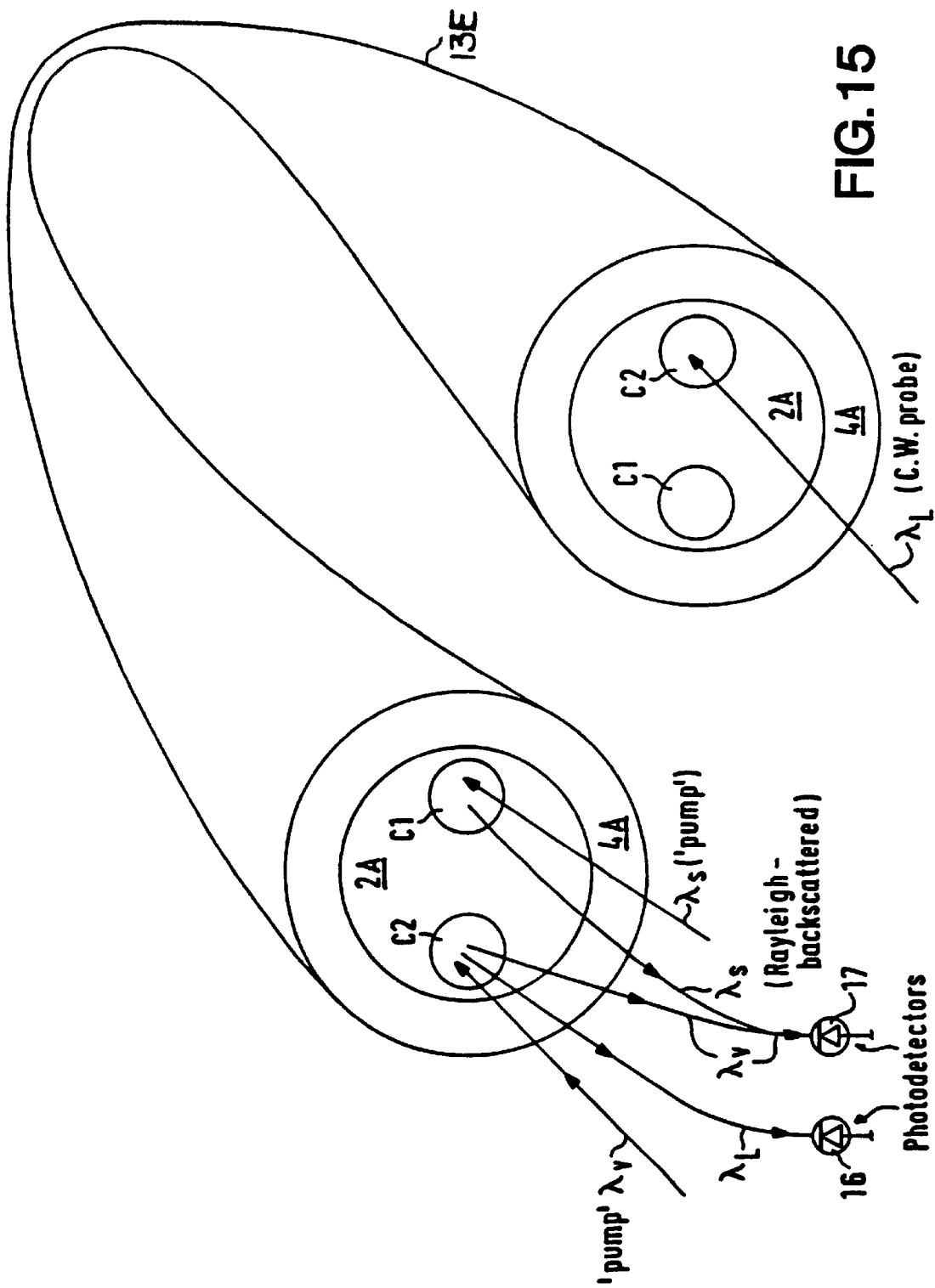
FIG. 15 illustrates a twin-core fiber suitable for sensing distributed forces and temperatures according to the invention.

FIG. 15 illustrates an embodiment based on a two-core fiber. The fiber 13E includes a clear glass core C1, a second core C2 made of glass doped with Nd(III), a first cladding 2A common to and around said two cores, and a second cladding 4A around the first cladding. Core C2 has preferably an index of refraction higher than that of core C1. Cladding 2A has an index of refraction slightly lower than that of core C1, and cladding 4A has an index of refraction substantially lower than that of 2A. The diameters of the two cores are preferably smaller than 10 micrometers. Force distributions are probed by launching interrogating (pump) light pulses having a narrow range of wavelengths $\lambda_s$ into core C1. A fraction $\alpha'$ of the intensity of this light is ejected from core C1 under the action of a force at any point, and is absorbed in core C2, where it generates a population inversion as described hereinbefore, and pulse amplification of counterpropagating light of wavelengths $\lambda_E$ of about 1.08 micrometers, the magnitude of which increases with the magnitude of the population inversion and, hence, of the magnitude of the force. The time of arrival of the amplified pulses to the measuring photodetector indicates the location along the fiber where the force was acting. The wavelengths $\lambda_s$ can be, for example, near 800 nm. Temperature distributions are probed by launching into core C2 interrogating light pulses of wavelengths $\lambda_v$, for example centered at 946 nm, and proceeding as described above in section 6.1.

Although FIG. 15 shows a circular cross section for the cladding surrounding the two cores, other cross sections may also be used, for example an elliptical one. It is not necessary for the two cores to be of similar diameter.

Since core B has an index of refraction higher than that of core A, distributed force sensing can be effected by means other than the generation of a population inversion in core B. If the fiber is interrogated with light pulses injected into core A having wavelengths outside the absorption bands of any dopant in core B, a lateral force acting on the fiber can couple a fraction of the intensity of each interrogating light pulse to core B, wherein it will propagate to the fiber distal end with a lower velocity than that of the interrogating light pulse within core A. The light thus coupled at any point along the fiber will then arrive at the fiber distal end after a resolvable interval t following the arrival of the pulse propagating along core A. This interval identifies the location along the fiber under the action of the force, according to the same relation (12) introduced in section 3.2 above. Good spatial resolution can be achieved if both cores A and B are single mode. From elementary fiber optics theory, core B can be single mode and still have a substantially higher index of refraction than core A if its diameter is smaller than that of core A.

Embodiment 2

Figure 16:
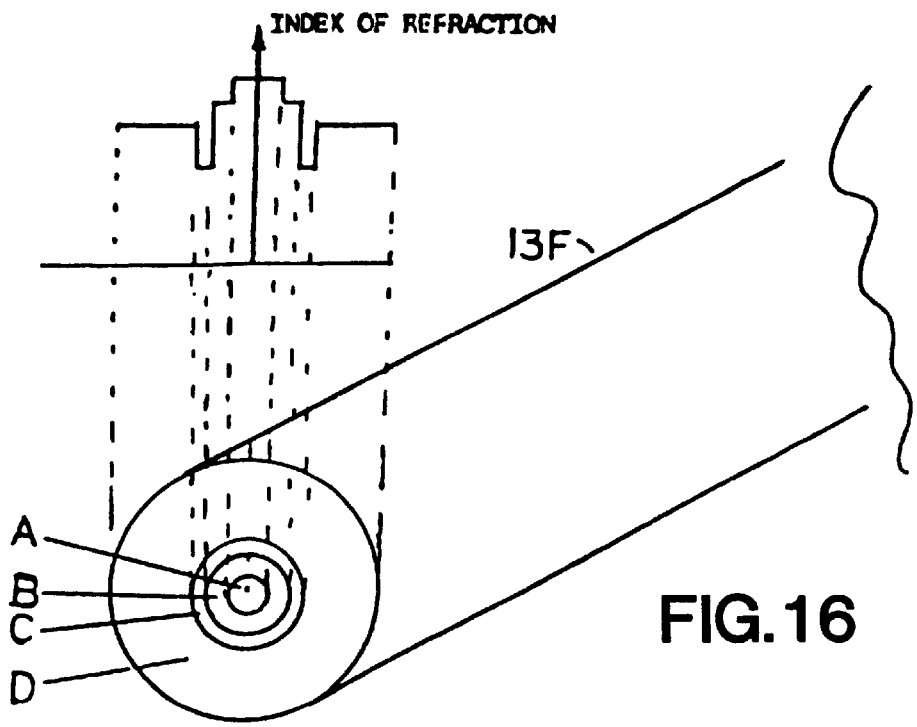
FIG. 16 illustrates an optical fiber probe for sensing distributed physical parameters by backward-stimulated Raman scattering processes.

An alternate arrangement to two cores within a common cladding is a 'composite core', namely a core comprised of two regions of different chemical composition and index of refraction, but so characterized that a light beam launched into either region at a fiber end propagates at all points along both regions, the optical power distribution between these regions at any point along the fiber being a function of the physical environment acting on the fiber at that point. An example of such a fiber is illustrated in FIG. 16. The probe is a long optical fiber 13F having a segmented light guide having a central core A with a diameter of about 5.0 micrometers ($\mu$m), an index of refraction $n_1$, and made of glass comprised of material laser-active at wavelengths $\lambda_{f1}$. Around this central region there is a second region B having a diameter of about 8.0 micrometers, an index of refraction $n_2$ only slightly lower than $n_1$ and no laser-active material, or a material laser-active at wavelengths $\lambda_{f2}$ different from $\lambda_{f1}$. Around region B there is a thin cladding C with an index of refraction $n_3$ substantially lower than $n_2$. Around cladding C there is an outer cladding D with an index of refraction $n_4$ higher than $n_3$ and only slightly lower than $n_2$. Regarding its index profile, the fiber is essentially a single mode "W" fiber with a segmented core, where region A is the central part of the core and region B is the other segment.

Figure 17:
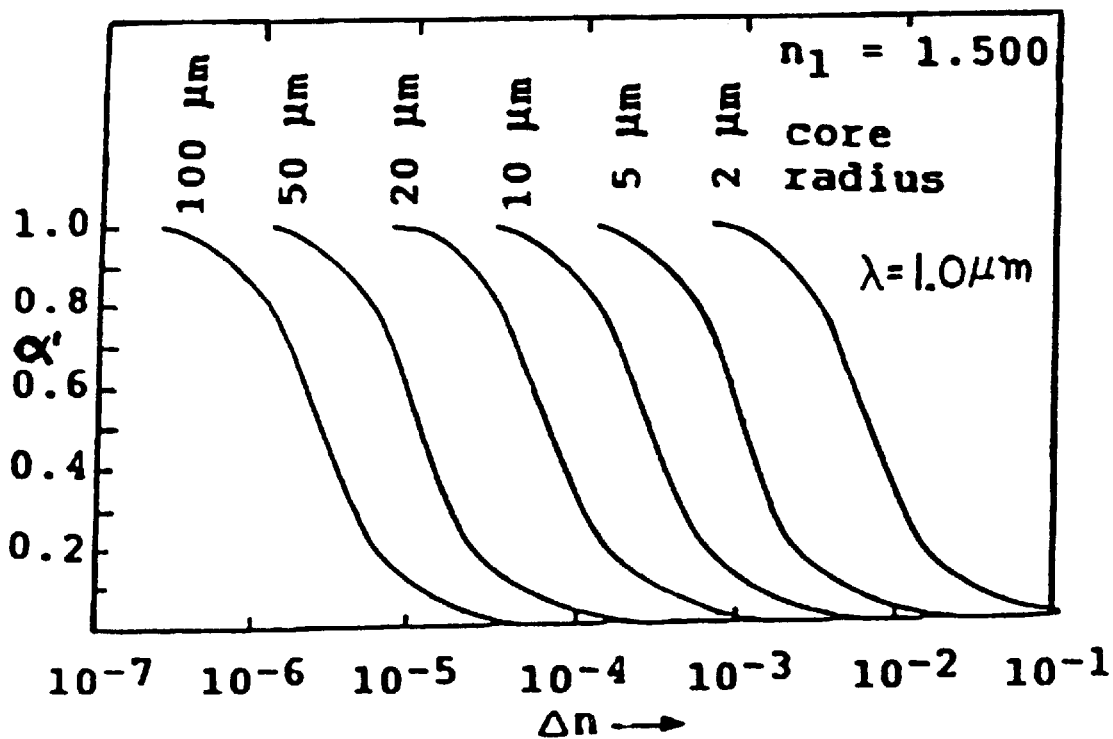
FIG. 17 illustrates the power distribution of the lowest order modes between the core and the cladding of an optical fiber, relative to the difference Δn of their indices of refraction.

If the value of $[n_1-n_2]$ (henceforth referred to as $\Delta n$) is lower than 0.01, then an appreciable fraction $\alpha$ of the intensity of the interrogating light launched into core A (or into the light guide comprising both regions A and B) will propagate along cladding B even in the absence of any external force on the fiber, due to the penetration into cladding B of the evanescent field of the guided light beam. The calculated optical power distribution between regions A and B for the lowest order modes of the core A has been determined previously as a function of $\Delta n$, for several values of the radius of the core A [U.S. Pat. No. 4,151,747], and is shown in FIG. 17. These lowest order modes are the only modes in the fiber of the instant example, at sufficiently low $\Delta n$ values. It is apparent that small changes of $\Delta n$ produce a relatively large change in the value of $\alpha'$. Relatively weak lateral forces produce the same effect, due to the low value of $(NA)_1$. Since the fiber is essentially a "W" fiber, strains or other forces which may cause a large extent of optical power redistribution between regions A and B will not cause excessive light losses from the segmented core comprising these two regions.

If the indices of refraction $n_1$ and $n_2$ have different temperature coefficients, then the intensity distribution of the interrogating light between regions A and B will be temperature-dependent, and the fiber may be used as a sensitive distributed temperature probe. From the data of FIG. 17 it can be verified that a difference in temperature coefficients of $n_1$ and $n_2$ of the order of $10^{-5}$ per kelvin (encountered in practice in some commercial glasses) can lead to temperature coefficients of the measured signal of the order of one percent per kelvin, adequate for most industrial purposes.

Because of the very low values of $(NA)_1$ that can be implemented in the fiber without excessive light losses, the optical power distribution between regions A and B can be made a very sensitive function of strain, and the fiber may be used as a sensitive distributed force sensor.

The chemical compositions of regions A and B should be chosen according to whether the fiber is to be used as a temperature probe or a force (strain) probe. If a force probe, the value of $(NA)_1$ should preferably be temperature-independent. This should be easy to ensure, as both regions A and B could be made of glasses with similar temperature coefficients for $n_1$ and $n_2$. If a temperature probe is desired, the compositions of the two glasses are preferably chosen so as to maximize the change in $\Delta n$ for a given temperature change.

6.4. The Sensing of Distributed Physical Variables Based on Stimulated Light Amplification in Optical Fibers Having at Least Two Light-guiding Regions, Using Backward-Stimulated Raman Scattering (BSRS) Processes Raman scattering is just one form of light scattering, and it differs from other forms of light scattering in that, when generated by monochromatic light or light of narrow spectral bandwidth of wavelengths $\lambda_s$, Raman-scattered light has wavelengths $\lambda_f$ substantially different from $\lambda_s$, the difference in photon energy corresponding usually to the energy of a vibrational quantum. Brillouin-scattered light also involves a spectral shift, but a much smaller one.

The above-captioned technology was disclosed in co-pending application Ser. No. 102,835, where it was briefly discussed (page 30, paragraph beginning on line 4) as an alternative to the use of a luminescent glass as amplifying medium. It was further discussed in preceding paragraphs of this application, and is discussed in more detail in this and the following paragraphs. A preferred embodiment of a distributed fiber probe based on BSRS is illustrated in FIG. 16, as described above, where one of the two light-guiding regions A or B is comprised of material capable of stimulated Raman scattering.

The fiber probe can be used in essentially the same device configuration as shown in FIG. 13, described with reference to a rare earth-doped laser-active fiber. The main difference is that stimulated light amplification in the BSRS probe occurs by stimulated Raman scattering instead of stimulated luminescence as in the rare earth-doped fiber probe. In the BSRS probe the wavelength $\lambda_f$ of the counterpropagating light beam generated by the light source 26, instead of being independent of the pump wavelengths, should follow approximately the relation $$\lambda_f^{-1} = \lambda_s^{-1} - \Delta v$$

where $\lambda_s$ is the wavelength of the interrogating light pulses and $\Delta v$ is the quantum energy of the Raman Stokes shift. The word "Backward" before "Stimulated Raman Scattering" indicates that the stimulated Raman signals received by the photodetection station originate from the light injected into the fiber at the end opposite to that where the interrogating 'pump' pulses are injected. In one example of a BSRS fiber probe having a cross-sectional structure as shown in FIG. 16, the core A is comprised of glass with a high concentrated of $P_2O_5$, and is surrounded by a region C which does not contain a significant concentration of $P_2O_5$. The magnitude of the Stokes shift is about 1,200 cm−1. In a preferred embodiment, the pump laser 10A launches into the light guide comprising regions A and B interrogating light pulses of an intensity sufficient to generate stimulated Raman scattering at all points along the fiber, and a duration $\tau$ of approximately $[(n_1+n_2)L/c]$ seconds, where L is the spatial resolution desired (also the interaction length of the pump pulses with the counterpropagating light of wavelength $\lambda_f$) and c is the velocity of light in free space. As the probe wave traverses the interaction length L of the fiber, its intensity $I_a$ within region A is pulse-amplified to the intensity $I_s$ according to the relation $$(I_s/I_a) = \exp[g P_o (1-\alpha') L] \tag{16}$$

where
g is the stimulated Raman gain coefficient of the doped glass; and
$P_o$ is the power density of the pump pulse over the interaction length L.

If the value of the exponent in equation (16) is not much greater than about 0.10, then $\Delta I$, the increase in the magnitude of $I_a$, is given approximately by $$\Delta I/I_o \approx g \cdot P_o (1-\alpha')^2 L \tag{17}$$

where $I_o$ is the intensity of the probe wave propagating along both regions of the segmented core over the interaction length L. Note that the fractional quantity $(1-\alpha')$ is squared. This arises from the fact that a force which redistributes the pump power between regions A and B also redistributes the power of the counterpropagating probe wave in approximately the same ratio.

To give an idea of the magnitude of ΔI one can obtain from this technique, let us assume some typical values for the parameters of equation (17, as follows:

$I_o$=10 milliwatts (mW)
$P_o$=5×10$^7$ W/cm$^2$ (about 10 W per cross-section of region A)
g=1×10$^{-10}$ cm/W (about the value of g for GeO$_2$ at 1.06 μm)
L=100 cm.
α'=0.5
  Diameter of region A=5 μm Then the magnitude of ΔI is about 1.25 mW, more than adequate for accurate measurements. By increasing the pump pulse intensity and decreasing its duration, one could obtain spatial resolutions of the order of centimeters.

While the fiber in the above example uses $P_2O_5$ as the Raman-scattering material, other materials, including many known to have higher Raman scattering coefficients, are also suitable for the purposes of this invention. Especially useful are glasses containing heavy metal oxides (see, for example, the publication by Miller et al., *Journal of Non-Crystalline Solids* 99, 289–307 [1988]).

Figure 18:
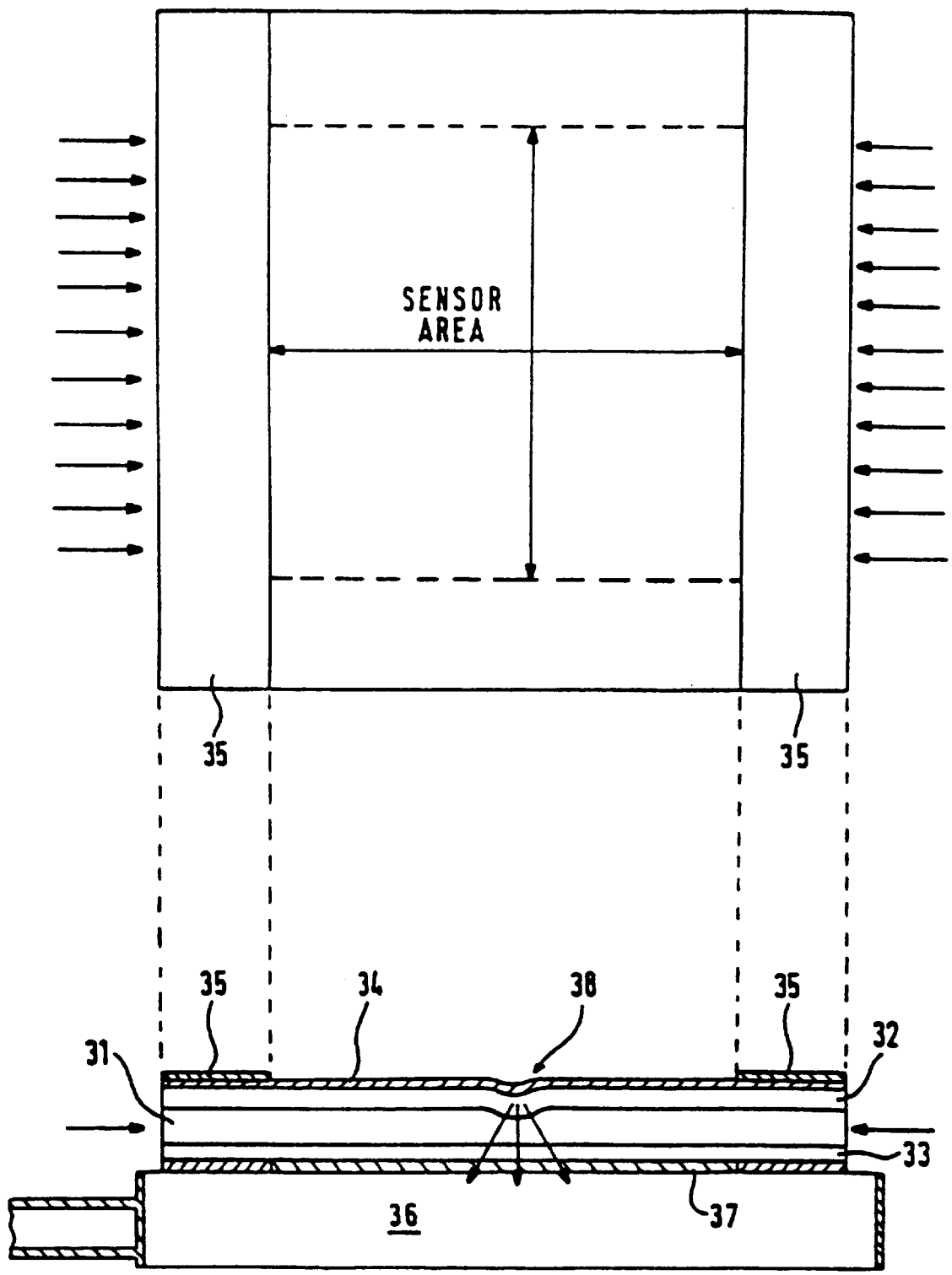
FIG. 18 illustrates a two-dimensional tactile sensor according to this invention.

7.0. Miscellaneous Applications of the Invention
7.1. Optical Tactile Sensors for Robots The teachings of this invention lend themselves to the construction of new useful devices. The same principles described above for the measurement of both forces and temperatures with a single sensor can be used to construct a two-dimensional tactile sensor for robots, also sensitive to both forces and temperature. The sensor can be understood with reference to FIG. 18. It consists of a clear elastomeric "sandwich" pad comprising three layers 31, 32, and 33. The inner layer 31 has an index of refraction $n_1$, and is bounded by the upper layer 32 and the lower layer 33, having indices of refraction $n_2$ and $n_3$, respectively, such that $n_1 > n_2 > n_3$. In one embodiment layer 31 has a thickness of about 200 micrometers, while each of the layers 32 and 33 have a thickness of about 100 micrometers. Layer 32 has dissolved therein a fluorescent dye characterized by a high fluorescence quantum efficiency and an optical absorption coefficient which is a sensitive function of temperature when illuminated with light of wavelength $\lambda_v$. When illuminated with light of a wavelength $\lambda_s$ shorter than $\lambda_v$, the absorption coefficient of the dye is independent of temperature within the temperature range of operation of the device.

The fluorescent layer has an electrically conductive film 34 applied to it, having a resisitivity such that a relatively low current passed through it will heat layer 32 to a temperature of about 40° C., or to any other chosen temperature.

The outer faces of layers 32 and 33 are coated with strips 35 of black paint as shown in the top view of FIG. 13, with a width at least two times greater than the thickness of layer 31.

The whole pad is in contact, through layer 33, with a two-dimensional silicon imaging array 36, having a light-sensitive surface covered with a dielectric optical filter 37, which is selectively transparent to the fluorescence wavelengths of the dissolved dye, and blocks the wavelength $\lambda_s$ of the illuminating light source.

The sensor pad works as follows:

Light of wavelength $\lambda_s$ is injected into layer 32, uniformly from one or, preferably, two or more square sides. The injected light has an angular distribution such as to overfill the numerical aperture (NA) of layer 31 defined by the relation $$(NA) = (n_1^2 - n_2^2)^{1/2}$$

The light rays having angles smaller than the critical angle $\theta_c$ for total internal reflection enter layer 32 and are 'stripped' by the black paint strips. The light reaching the clear inner square of the pad is propagated inside layer 31 by total internal reflection at the boundaries between layer 31 and layers 32 and 33. Any pressure at any localized point 38 on the pad causes a deformation which forces a fraction of the intensity of the light propagating thorough layer 31 into layer 32, thus causing a fluorescence emission from the dissolved dye, which is detected by the detector(s) in the imaging array located just below the point 38. The intensity of the generated fluorescence is determined by the magnitude of the deformation and, hence, by the magnitude of the pressure at that point. If pressure is applied at a plurality of points within the clear area of the pad (that is, within the area bordered by the black strips) the silicon sensor array will generate a two-dimensional map of the forces acting on the pad.

After a video frame is obtained, the process is repeated, except that the light injected into layer 31 now has the wavelength $\lambda_v$. This wavelength will produce a fluorescence intensity from the dye which is determined by the temperature of layer 32 as well as by the pressure applied at point 38. The ratio of the fluorescence intensities produced by the two illuminating wavelengths defines the temperature at point 38 while the fluorescence intensity produced by the illumination wavelength $\lambda_s$ defines the magnitude of the pressure or force.

7.2 Fiberoptic Keyboards

The British journal Sensor Review (April 1984, pp 70–72) discusses the need for electrically passive fiberoptic keyboards in some environments where electronic keyboards may be unsuitable, for example in underwater applications, in flammable atmospheres, or in electrically noisy environments, and describes a complicated experimental fiberoptic keyboard. The teachings of this invention for the trapping and modification of light deflected out of the core of an optical fiber under an acting force can be used to construct improved, simpler keyboards. In contrast to the device described in said issue of Sensor Review, which require $2.N^{1/2}$ sequentially pulsed light sources for a number N of keys, the fiberoptic keyboards of this invention require not more than one light source. Furthermore, this single light source can be shared by numerous fiberoptic keyboards operated simultaneously.

An example of a fiberoptic keyboard using the principles of this invention uses two identical optical fibers, each comprising, a) a clear core having an index of refraction $n_1$; b) a clear cladding around said core, having an index of refraction $n_2$ lower than $n_1$ and a thickness of a few micrometers; c) a second cladding having an index of refraction n, now lower than $n_2$ and a diameter preferably greater than twice the core diameter and having also a wavelength-selective light absorber dissolved therein; and d) an outer cladding with an index of refraction $n_4$ lower than $n_2$.

Figure 19:
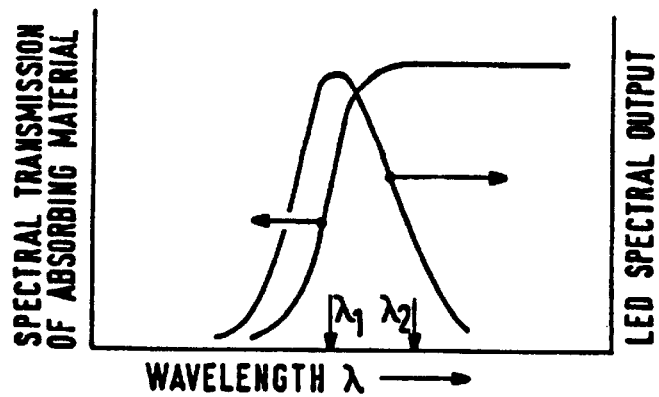
FIGS. 19, 19A and 19B illustrate fiberoptic keyboards according to this invention.

A general representation of the optical transmission spectrum of a suitable light absorber is shown in FIG. 19, which also includes a typical output spectrum of a C.W. light-emitting diode (LED) used for operating the keyboard, including at least two easily separable wavelengths $\lambda_1$ and $\lambda_2$. In the keyboard system, a length L, of each fiber is used such that the total optical density to light of wavelength λ1 propagating along the light-guiding region including the light-absorbing second cladding is about 1.3, corresponding to a transmitted light intensity P of about 5 percent of the incident light intensity $P_o$, according to the relation $$\log(P/P_o) = -\alpha L$$

where α is the absorption coefficient of the light-absorbing second cladding per unit length, the product αL being the full-length optical density of the fiber.

Figure 19A:
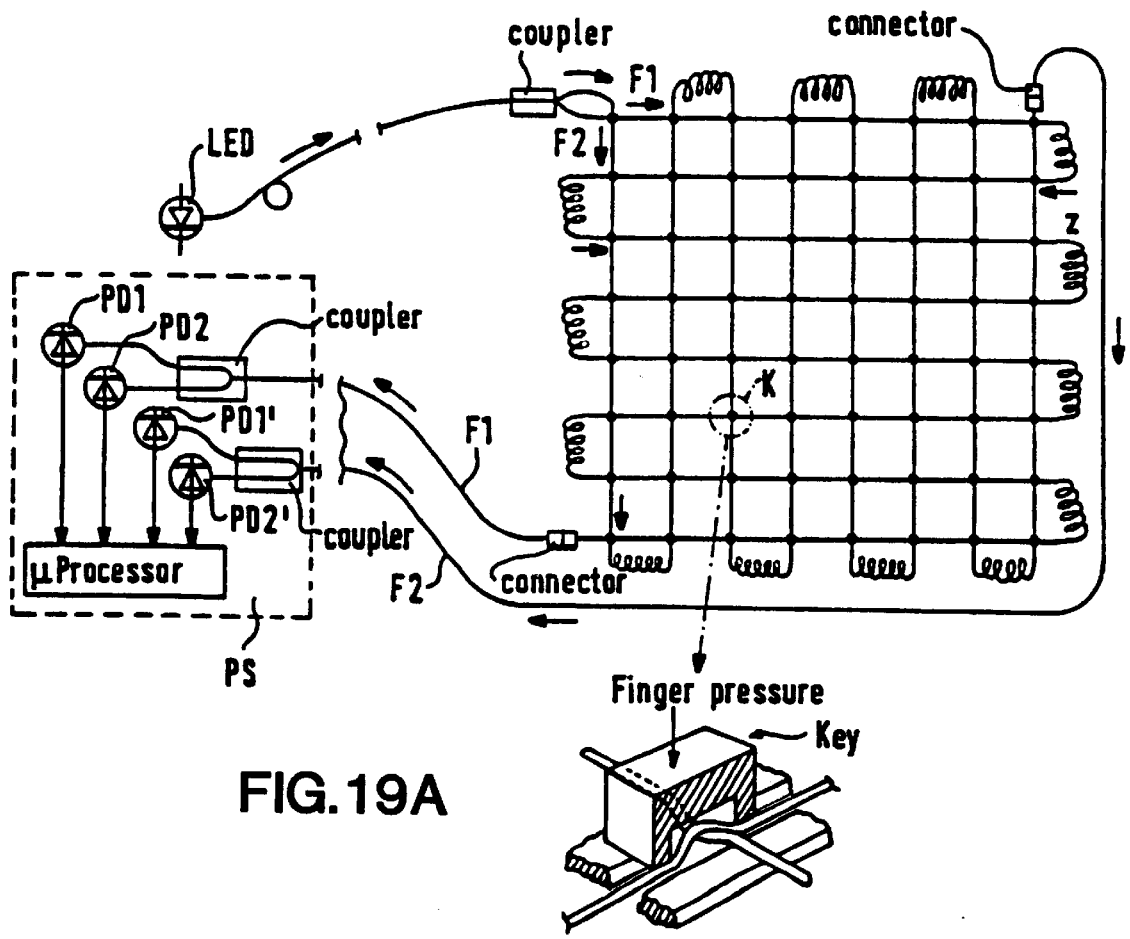

FIG. 19A is a schematic representation of the operating keyboard. Two fibers, F1 and F2, are laid out as shown under an 8×8 matrix of keys, F1 passing under all rows of keys and F2 passing under all columns of keys, the two fibers intersecting under each key as shown in the area of detail under the matrix. Between each contiguous rows and columns of keys there is a fiber segment S of length z, at least 10 times longer than the fiber segment under each row or column of keys. When a key is depressed, at least an appreciable fraction of the intensity of the interrogating light launched into the core of each fiber by the LED is deflected into the light-absorbing second cladding. The deflected light propagates within the light-guiding region including said second cladding along the fiber length to the photodetection station PS, and the spectral component of wavelength λ1 is partially absorbed. The transmitted light intensity $P_t$ of wavelength λ1 is given by the relation $$\log(P_t/P_o) = \alpha L(1 - N'z' - x)$$

where z' is equal to z plus the length of fiber under a row or column of keys,

N' is the number of rows or columns (depending on whether the fiber is F1 or F2, respectively) preceding the row or column of the depressed key; and x is the length of fiber under the preceding keys of the same row or column of the depressed key.

Since z' is more than 10 times greater than x, the value of x, determined by the number of preceding keys in the same row or column, won't affect appreciably the measured value of $P_o$. Additionally, light of wavelength λ2 is not absorbed appreciably by the light-absorbing material. Therefore, the ratio of the light intensities of wavelengths λ1 and λ2 transmitted by each fiber will be a unique function of the location of the depressed key. The light outputs from each fiber are fed to two photodetector pairs, PD1-PD2 and PD1'-PD2', the digits 1 and 2 representing that the photodetectors are selectively sensitive to wavelengths λ1 and λ2, respectively.

For a full-length optical density of 1.30, the light intensities of wavelength λ1 transmitted by each fiber for keys depressed at two contiguous rows or columns varies by about 30 percent for an 8×8 matrix of keys from one row or column to the next, and the percentage of variation increases as the full-length optical density increases. Therefore, the set of readings from the two sets of photodetectors, for each depressed key, will unambiguously identify the key.

The reading can be made independent of any variation of the fraction of the interrogating light intensity deflected into the absorbing cladding, by directing only the deflected light to the photodectors. This can be achieved simply by covering the output tip of the fiber core by a black absorber, or by other means which would be apparent to workers with at least average competence in the art to which this invention pertains.

In a variant of the above method, the light-absorbing material in the second cladding is luminescent, and light of the shorter wavelengths within the luminescence spectral output is partially reabsorbed, the extent of the reabsorption varying as a function of the distance from the point under the depressed key to the distal end of the fiber, the luminescence emitted at longer wavelengths being only minimally absorbed. In this case one identifies the depressed key by the ratio of the intensities of the lights emitted at the two wavelength regions. One specific example of such a luminescent system is Nd(III)-doped glass, the luminescence spectrum of which comprises a band at about 890 nm, and another strong band at about 1060 nm (in addition to at least another band at longer wavelengths). The luminescence light within the 890 nm band is partially reabsorbed, while the band at about 1060 nm is only minimally attenuated, and can be used as a reference.

Figure 19B:
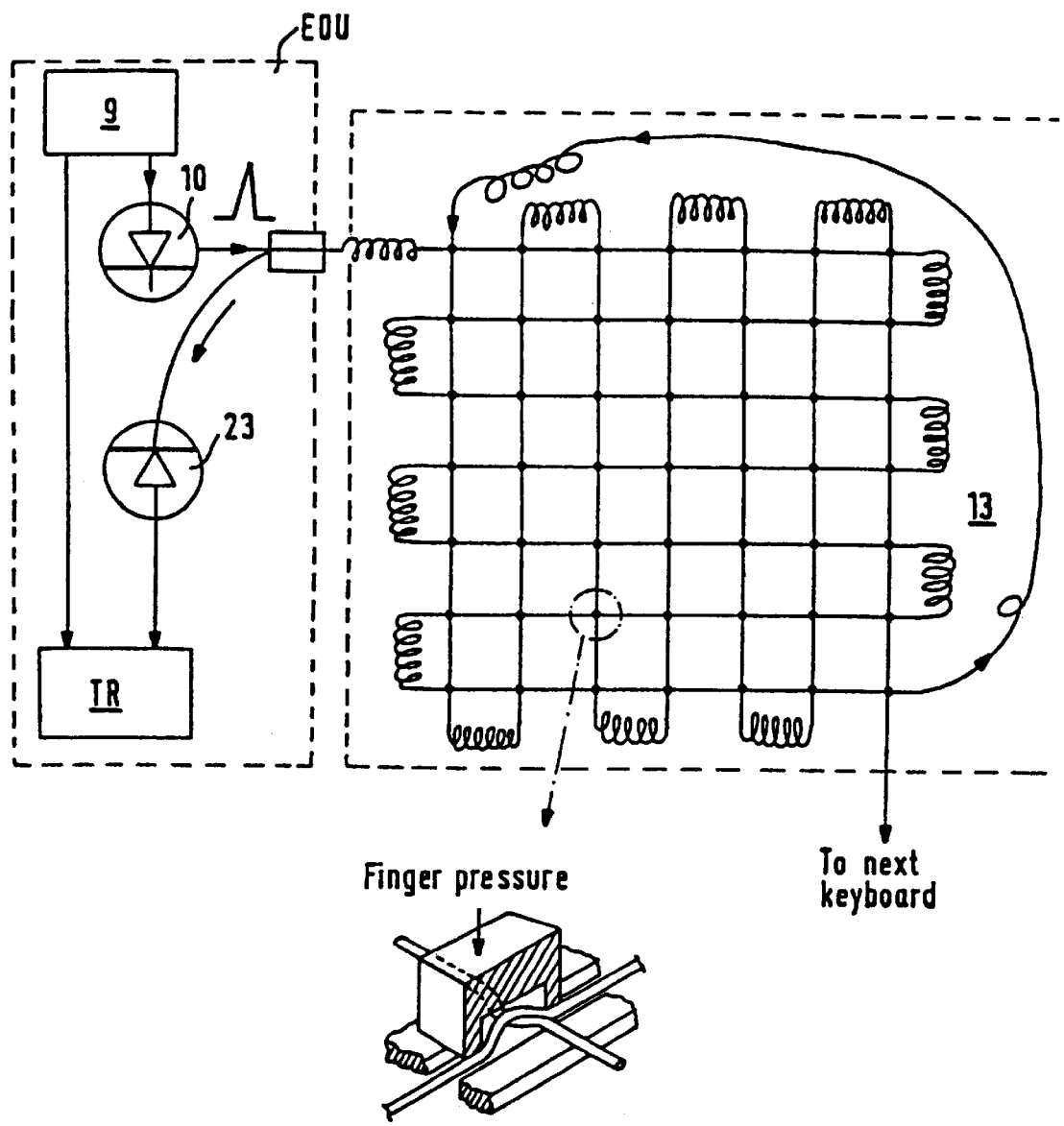

Another kind of keyboard, suitable for multiplexing, is illustrated in FIG. 19B. A light source 10, preferably an LED or a laser diode, is driven from power supply 9 to produce a recurrent train of light pulses with a duration preferably not greater than about 20 nanoseconds, and a repetition rate of $10^4$ pulses per second. At the keyboard the optical fiber 13B is laid out as shown, with intersecting horizontal and vertical segments, and with a depressable key at each or columns of keys traversed by fiber 13B there is a fiber segment of length L of about 2.0 meters, designed to delay the time of arrival of the interrogating light pulses at any row or column by about 10 nanoseconds after the preceding row or column. At any key position, the set of fiber distances from the point of intersection to the electrooptical unit EOU is unique for that key. As the key is depressed, a small (but easily measurable) fraction of the intensity of the interrogating light propagating through the fiber core is forced into the fiber cladding and the interface between this cladding and the fluorescent coating 4'. The fluorescence light pulses generated at the evanescent wave layer of the coating arrive at the photodetector 23 at two specific times (relative to the time of injection into the fiber of the interrogating light pulses) which uniquely identify the key. The power supply 9 provides the reference timing pulse which triggers the time sweep of the timer TR. The time interval between the fluorescence pulses from contiguous rows or columns of keys is approximately 20 nanoseconds. In the illustrated example, the total length of optical fiber needed for 49 keys is 28 meters. In general, the total fiber length L needed for any number N of keys is given by $$L = (tc/n) \cdot N^{1/2}$$

where c is the velocity of light in a vacuum;

t is the needed time resolution; and n is the index of refraction of the glass in the fiber. (Although the indices of refraction of the core glass and the cladding glass are slightly different, they are sufficiently close to 1.50 to use this value in most design calculations).

The electro-optical unit described above can be used, without major modifications, to interrogate and read out a multiplicity of keyboards in a series array on a single fiber, or in parallel on a plurality of fibers.

The technique described above for the for the time-division-multiplexed keyboard can be used with any fiber in which light deflected from the core into another light-guiding region can be separated in the time domain from the interrogating light. The fiber 13A subject of FIG. 9 is an example of an optical fiber also suitable for use in fiberoptic keyboards. In this case the light deflected under the action of a depressed key is separated in the transmission mode as discussed in section 3.2.

7.3. The Multiplexing of Sensors on a Single Unbroken Optical Fiber

Distributed force sensors can be used for multiplexing sensors for any physical variable which can be converted into a mechanical force. The distributed fiber sensors of this invention can receive inputs from any such sensor at any desired location, and transform those inputs into luminescence signals when the optical fiber is interrogated by a suitable light source in a device like an optical time domain reflectometer (OTDR). As explain hereinbefore, the intensities and the time characteristics of these luminescence signals define both the location along the fiber where the sensor is located and the value of the measurand. A preferred type of sensor to be coupled to the distributed sensing fibers of this invention is the well-known microbend sensor. Examples of microbend sensors which can be multiplexed on a sensing fiber of this invention are:

(a) microbenders mechanically coupled to a displacement-type sensor, for instance the diaphragm of a pressure-sensing transducer. Thus the sensor can be entirely electrically-passive; and (b) electrically-driven microbenders, in which case only the signal transmission through the fiber will be electrically passive.

A preferred way of coupling sensor information into an optical fiber according to this invention is to convert the sensor output into an oscillatory force applied to the fiber, the oscillatory frequency being a known function of the value of the parameter being measured. A frequency signal is transmitted through an optical fiber with less degradation than an intensity signal.

7.4. A Fiber Optic Cooler

When on e excites the fluorescence of a highly efficient luminescent material with light of wavelengths longer than the median wavelength of the luminescence light emitted by the material, as discussed above, the material can be cooled, and this can be used to construct a purely optical cooler. The concept of cooling by light can be understood with the help of FIG. 1. Consider a solid photoluminescent material having a luminescence quantum efficiency near unity (or at least greater than 0.9), and a molecular electronic energy level diagram represented schematically by FIG. 1. The relative molecular populations of levels 40, 41, 42 and 43 follow the Bose-Einstein population factor $[\exp(E_v kT) -1]^{-1}$, where $E_v$ is the level energy relative to the ground level 40. At ordinary temperatures there is a small but operationally significant number of molecules of the solid occupying the thermally excited level 42 with an energy $E_v$ of about 3000 $cm^{-1}$ above the ground level. Now, suppose the photoluminescent material has an electronically excited emissive level with an energy $E_s$ of 15,500 $cm^{-1}$, and that the mean photon energy of its luminescence light is 14,500 $cm^{-1}$. The wavelength of the excitation light source is 800 nanometers (nm), available from the very efficient AlGaAs diode lasers. The emitted photons have an energy 16% higher than the absorbed photons. This means that if the luminescence quantum efficiency is appreciably higher than 0.86, the solid body will be cooled.

Practical considerations

For an $E_v$ value of 3000 $cm^{-1}$, the optical absorption coefficient of the luminescent material will be 6 to 7 orders of magnitude smaller than its peak absorption coefficient. This means that, for efficient operation, (a) The peak absorption coefficient must be high, of the order of $10^{-17}$ to $10^{-16}$ $cm^2$ per molecule, and (b) The optical path along the luminescent material must be long, preferably of the order of several meters or longer.

The above requirements can be met by using efficient fluorescent dyes as dopants in long optical fibers. Dyes with fluorescence quantum efficiencies greater than 0.90 are already known.

For practical applications, one could attach the device to be cooled to a fiber optic coil containing the fluorescent dopant.

8.0 Non-Imaging Optical Concentration Techniques Relating to this Invention.

Unlike the embodiments of this invention based on the use of fluorescent dyes, the embodiments based on glasses doped with luminescent rare earth ions must use high excitation densities in order to achieve stimulated emission and probe light amplification in distributed sensing systems. The way to achieve these high excitation densities with excitation sources of low or moderate power (not sure than a few hundred milliwatts) is to confine the excitation energy into an active wave-guiding region of the sensing fiber having a very small cross section. The emitting areas of many otherwise convenient light sources are often much larger than such needed small cross-sections. Commercial laser diode arrays have output powers from 790 to 870 nm of the order of 1 Watt C. W., originating from a rectangular source about 200 micrometers wide and about 1 micrometer high. One could clearly not image more than a few percent of this power into a fiber core with a diameter of a few micrometers. If, however, the core contains a luminescent material which efficiently absorbs the output of said diode laser array, one could concentrate at least a large fraction of the energy emitted by the array into said core, without violating the second law of thermodynamics, by means other than the imaging of the light source into the core launch end. One way is to enclose the luminescent core within a clear first cladding of conventional circular cross-section, into which the light source is imaged. A far more efficient arrangement is disclosed herein, using as an example a temperature-sensing optical fiber based on Nd(III)-doped glass. The principle is shown in the preferred embodiment illustrated in FIG. 20. It uses a fiber 13G with a light-guiding region A. having an index of refraction $n_a$ and a near rectangular cross-section, with its height about equal to or not much higher than the diameter of the cylindrical ND(III)-doped core B, of not more than about 10 micrometers ($\mu m$), and a width not much greater than, and preferably equal to, the active width of the diode laser array (~200 $\mu m$). The index of refraction $n_b$ of the doped core is higher than $n_a$. Around region A there is a cladding C with an index of refraction $n_c$ lower than $n_a$. Light from the laser diode array is launched into region A wherein it propagates and, at each pass along the width of the near rectangular cross-section, it passes through the doped core, a small fraction of its intensity is absorbed by the Nd(III) in the core, until essentially its whole intensity is absorbed in the core. The optical energy that can thus be coupled into the core can be many times greater than that which can be launched into the core end. Furthermore, the near rectangular cladding A of FIG. 20 affords more efficient pumping per unit fiber length than an arrangement using a conventional cylindrical cladding of diameter equal to the active width of the diode laser array. In the latter case, if the doped core is at the center, then the so-called 'skew' rays, which would outnumber the so-called 'meridional' rays, would not enter the doped core and would not contribute to the pumping. And if the doped core is placed near the edge of the cylindrical cladding in order to capture the skew rays, then the excitation yield per unit fiber length would by many times lower than in the case of the near rectangular cladding A, as the cross-sectional area relative to the cross-sectional area of the doped core is much larger.

A distributed force-sensing fiber using the same optical concentration principles must be adapted to meet the requirement of a minimal luminescence background per resolvable fiber length in the absence of an external force (or internal strain). Such a fiber, 13H, illustrated in FIG. 21. The waveguiding region A' into which the interrogating light is launched has a cross section about an order of magnitude greater than that of the Nd-doped core B. Between core B and region A' there is a cladding C having an index of refraction lower than those of core B and region A'. Core B has an index of refraction not lower than that of region A'. Around region A' there is a second cladding D having an index of refraction lower than that of the first cladding C. At any point along the fiber where a force is acting, a fraction $\alpha_s$ of the intensity of the interrogating light launched into the light-guiding region A' is ejected into cladding C and core B, where it produces a population inversion of the Nd(III) ions. The Nd(III) concentration in core B can be pre-selected so as to cause total absorption of the force-coupled interrogating light over the resolvable fiber length (for instance 1 meter). The wavelength $\lambda_s$ of the interrogating light can also be pre-selected for optimum absorption. The strongest absorption band of Nd(III) in the near infrared region peaks at or near 805 nm, generated by efficient, commercially available diode lasers, including diode laser arrays. One could also use interrogating light pulses with powers of the order of hundreds of watts or more, and durations of the order of $10^{-7}$ seconds or less, without generating stimulated-Brillouin scattering or stimulated raman scattering that would occur if the same powers were launched directly into the fiber core.

Distributed force sensing with the above fiber can be carried out according to the phase angle division multiplexing technique discussed in section 5.0 above, using a counterpropagating moderate power ($\lesssim 25$ mW) continuous laser beam to probe the population inversion in the fiber produced by the action of the forces to be measured. In order for the method to be applicable, the amplification of the probing counterpropagating light must occur at the same time domain frequency as that of the light modulation at the source. This requires that the smallest forces to be measured cause a population inversion in each of the sensing points along the fiber. If there are, for instance, 50 or more sensing points, it may be necessary to couple into core B an optical power of the order of 100 milliwatts or more of the AC-modulated light from the 'pump' laser (or array). The concentration technique disclosed herein facilitates this task.

This concentration technique is also valuable for coupling into an optical fiber an optical power high enough to cause undesirable non-linear effects or damage if focused directly into the launch end of the fiber core.

The optical concentration method of FIG. 20 can also be used for pumping a fiber laser or amplifier with a light source of larger emissive area than that of the fiber laser or amplifier.

8.1 An Application: the Pumping of Erbium-Doped Fiber Amplifiers.

The pumping system illustrated in FIG. 20 can be used for constructing practical pump sources for optical fiber amplifiers useful for long distance telecommunications. It is known that state-of-the-art silica fibers have their lowest light attenuation for light wavelengths of about 1.54 micrometers (um). This also happens to be the spectral region comprising the main laser band of Er-doped glass. Thus, Er-doped fiber amplifiers are presently the subject of considerable development by a plurality of laboratories.

It is generally agreed that a (980±10) nm pump source is desirable, but no practical such source is presently available. Considerable effort is under way to develop laser diodes operating at about 980 nm, but they are presently very costly and are likely to remain so in the near future. The teachings of this invention allow the use of inexpensive AlGaAs lasers or laser arrays operating at about 800 to 820 nm for generating the pump radiation at about 980 nm inexpensively. A system for generating said pump radiation is shown schematically in FIG. 22. The laser diode array LD pumps a fiber laser system FL, which emits laser radiation of wavelengths near 980 nm. There are at least three different embodiments of the fiber laser system FL, as follows:

Embodiment 1.

Figure 23:
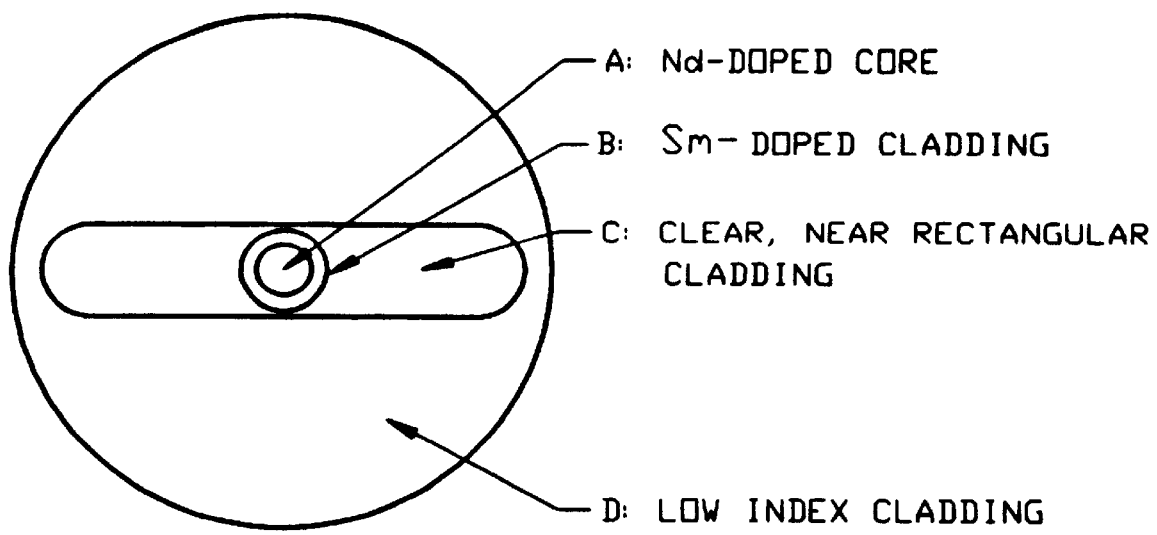

In this embodiment the fiber laser system FL includes an optical fiber $F_1$ whose cross-sectional structure perpendicular to the fiber length is illustrated in FIG. 23. The fiber core A, having a radius not greater than a few micrometers and an index of refraction $n_1$, is comprises of $Nd^{3+}$-doped glass and is surrounded by a thin first cladding B made of glass doped with $Sm^{3+}$. Cladding B has a diameter of a few micrometers and an index of refraction $n_2$ lower than $n_1$. A second cladding C surrounds cladding B. Cladding C has a near rectangular cross section the larger dimension of which is much greater than diameter of the core, and is made of a glass transmissive to the pump radiation, and has an index of refraction $n_3$ lower than $n_1$. Around cladding C there is an outer cladding D having an index of refraction $n_4$ lower than $n_3$. The fiber $F_1$ is connected in series to a fiber $F_2$, whose core is comprised of $Yb^{3+}$-doped glass. Pump radiation from the laser diode array having an intensity high enough to generate a population inversion of the $Nd^{3+}$ ions in core A is launched (injected) into cladding C at the proximal end of the fiber $F_1$. After numerous passes through the $Nd^{3+}$-doped core, most of the intensity of the pump radiation is absorbed by the $Nd^{3+}$ ions, generating a population inversion therein, and laser action at wavelengths near 940 nm. Laser action at the main $Nd^{3+}$ laser wavelengths near 1060 nm or at the wavelengths near 1400 nm is prevented by the $Sm^{3+}$ ions in core B, which selectively absorb these wavelengths and therefore prevent their amplification, while being essentially transparent to light of wavelengths near 940 nm and to the 810 nm pump wavelengths. The laser radiation from $Nd^{3+}$ pumps the $Yb^{3+}$ ions in the core of fiber $F_2$. At sufficiently high pump powers from the $Nd^{3+}$-doped core of fiber $F_1$, most of the $Yb^{3+}$ ions in the $Yb^{3+}$-doped core of fiber $F_2$ will be in the $^2F_{5/2}$ excited level, and laser or superluminescence emission at about 975 nm will occur. This laser or superluminescence emission can be used for efficiently pumping an $Ex^{3+}$-doped fiber amplifier.

The use of wavelength-selective absorbing claddings can be used as a general method for suppressing laser action in a fiber laser within an otherwise strong laser transition, thus facilitating laser action in a less strong laser transition of the same laser material.

Embodiment No. 2.

Figure 22:
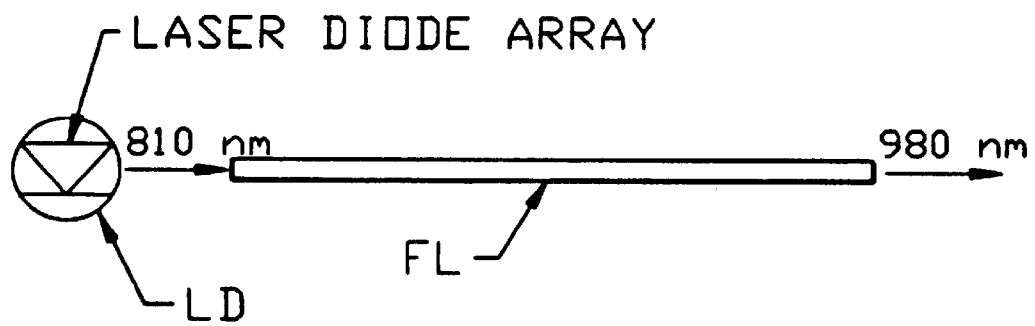
FIGS. 22–23 illustrate arrangements for the pumping of Er(III)-doped fiber lasers.

In this embodiment the fiber laser system FL comprises a fiber similar to that shown in FIG. 20. The fiber core is comprised of a glass co-doped with $Nd^{3+}$ and $Yb^{3+}$, both at concentrations of about 1% or higher. This core, with an index of refraction $n_1$, is disposed within a clear first cladding of near rectangular cross-section, with its larger dimension similar to that of region A of FIG. 20 and an index of refraction lower than that of the core. This cladding is surrounded by an outer cladding like cladding D of FIG. 20, and having an index of refraction lower than that of the first cladding. The only significant difference with the fiber of FIG. 20 is that the core is co-doped with $Nd^{3+}$ and $Yb^{3+}$. The radiant output from the laser diode array of FIG. 22 is launched into said clear first cladding and, as it propagates along the fiber, it is absorbed by the $Nd^{3+}$ ions in the core. The absorbed energy is transferred to the $^2F_{5/2}$ excited energy level of the $Yb^{3+}$ ions, generating a population inversion therein. When the number of $Yb^{3+}$ ions occupying this excited level exceeds the number occupying the ground level $^2F_{7/2}$, laser light is emitted at wavelengths near 975 nm, which can be used without further transformation to pump an $Ex^{3+}$-doped fiber amplifier.
Embodiment No. 3.

This embodiment of the fiber laser system FL uses the same fiber $F_1$ as embodiment No. 1, to generate the same laser radiation at wavelengths near 940 nm. The difference is that the fiber is connected in series to fiber $F_3$, whose core is comprised of material capable of stimulated Raman-scattering and having a Raman shift $\Delta v$ of about $(450\pm20)$ $cm^{-1}$. Under strong pump radiation as in Embodiment 1, the fiber $F_3$ will emit strong radiation at wavelengths near 980 nm, which can be used for pumping an $Er^{3+}$-doped fiber amplifier.

9.0 Applications of this Invention to Fiber Optic Communications.

The provision of a luminescent waveguiding region to an optical fiber, in addition to the standard glass core and glass cladding of communication fibers, and without affecting the light propagation properties of these standard waveguiding regions, allows a plurality of new communications-related uses of the fiber, besides its use as a distributed sensing probe. Two of such uses are outlined below:

Improved Diagnostics of Fiber Networks.

In its simplest embodiment as a distributed sensing probe, the force-sensing fiber of this invention is essentially a standard communications fiber with a standard core, a standard cladding, and a plastic coating around the cladding which, except for a few parts per million of a fluorescent dye dissolved in it, would be essentially the same as some of low index polymers presently used for the protective coating of optical fibers. Yet it is that minute concentration of the dye which enables the fiber to produce diagnostic signals from lossy points along the fiber which are orders of magnitude stronger than those from the decrease of the intensity of the Rayleigh-backscattered signals conventionally measured with OTDR diagnostic instruments, but without affecting the communication signals propagating along the fiber core. The force-sensing fiber of this invention could, therefore, be used as a communications fiber in local area networks, and its force-sensing characteristics would be a built-in diagnostic feature which would greatly extend the capability of optical time domain reflectometry. This communications fiber could be used, additionally, for distributed sensing, and the sensor information would be transmitted through the same fiber without interfering at all with its usual communication functions.

The Non-invasive Coupling of Information to the Fiber from the Side at Any Point.

The force-sensing fibers of this invention allow the non-invasive coupling of information into the fiber from the side at any point. The information can be coupled in digital form by any sequence and/or timing of 'force bits' applied by means of, for example, a piezoelectric transducer, when a train of short interrogating light pulses are propagating along the fiber core. The coupled information, converted either to fluorescence light pulses if the fiber has a fluorescent cladding, or to time-resolved light pulses if the fiber is like the one described in section 3.2 supra and FIG. 9 will then propagate to at least one fiber end time-and/or wavelength separated from the interrogating light. Information can also be coupled by direct optical excitation of the fluorescent cladding by an external light source.

10.0 A Medical Application: Laser Surgical and Photo-Irradiation Tips Which Are Also Temperature-Sensing Probes.

In recent years there has been a large increase in the use of high power lasers in medicine, for applications like surgery, hyperthermia, photodynamic therapy, and other laser irradiation techniques. In one type of application, laser energy conducted by an optical fiber or fiber bundle to a surgical tip heats up the tip to permit operations requiring controlled heating of the biological tissue being worked on. Unfortunately, there is no reliable means for measuring the temperature of the heated tip. Thermal measurements are usually conducted by placing a temperature sensor at some distance from the tip, but this is not an adequate substitute for measuring the temperature at the tip itself.

The teachings of this invention permit one to make surgical tips which are also their own temperature probes and which, in addition, can function as light diffuses for medical photoirradiation purposes.

Figure 24:
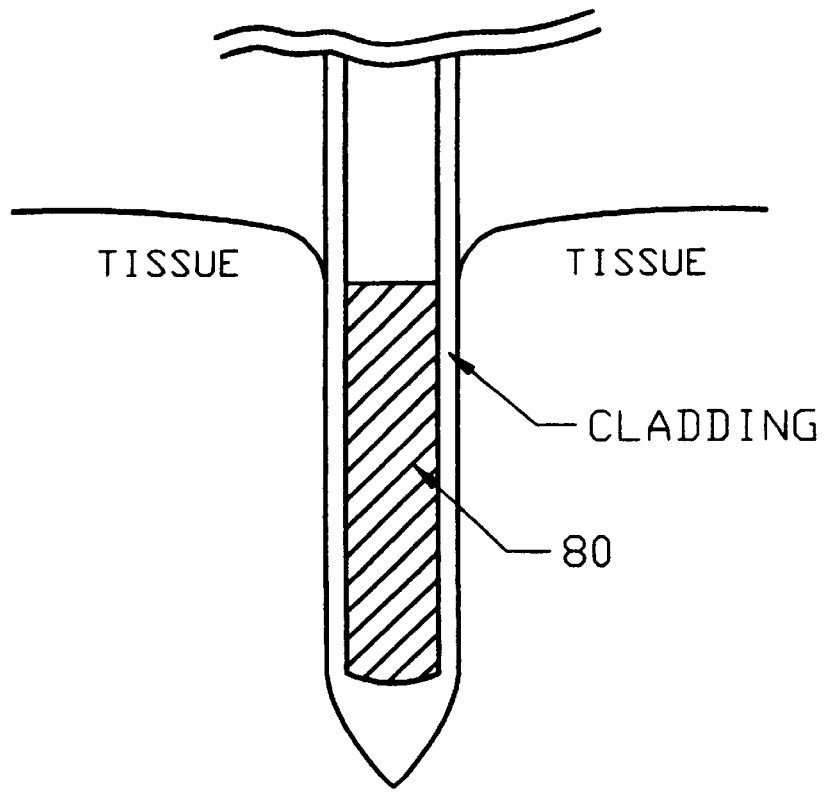
FIG. 24 illustrates a light-diffusing photo-irradiation probe for medical applications, capable of measuring its own temperature.

An example of a surgical tip/light diffuser according to this invention is illustrated in FIG. 24. It consists of length of clad rod 80 of similar diameter to that of the optical fiber to which it is attached, and having dissolved therein a luminescent material with a luminescence spectrum suitable for the intended treatment, if used for photo-irradiation, at a concentration pre-determined to convert the desired fraction of the excitation light into luminescence light.

Used as a surgical tip, the rod, which may be terminated in a point as shown, is heated by absorption of laser radiation from sources like an excimer laser (ultraviolet), an AlGaAs laser array of a carbon dioxide laser. The laser radiation is delivered through an optical fiber 81, at a power and energy needed for heating the rod to the desired temperature range. Suitable based materials for the rod are sapphire and yttrium aluminum garnet, suitably doped with a luminescent material. A suitable dopant for yttrium aluminum garnet (YAG) is $Nd^{3+}$, the doped material being designated herein as Nd:YAG.

The probe can be used as a temperature sensor (usually to measure the temperature at which it has been laser-heated by the method disclosed in section 2.1, above. Nd:YAG, for example, can be interrogated with light of wavelength of 946 nm. Under this illumination, the probe absorbs a temperature-dependent fraction $\alpha_v$ of the interrogating light determined by equation (3), with $E_v$ being approximately equal to 857 $cm^{-1}$. The luminescence intensity of the probe will follow approximately equations (4) and (5).

The same probe can also be used as a light diffuser. The Nd:YAG probe can be excited through the fiber 81 by a high power AlGaAs laser diode array emitting at about 805 nm, within a strong absorption band of Nd:YAG. The absorption energy is converted into luminescence light which is emitted nearly isotropically from the probe, thus affording homogeneous illumination of the biological tissue surrounding the probe. Other luminescent dopants like $Cr^{3+}$, $Er^{3+}$ or $He^{3+}$ can be used for providing illumination at different wavelengths, depending on the dopant.

11. A fiber optic temperature control system for 'hot tip' laser angioplasty.

The destruction of tumors and the removal of arterial plaque are growing application of lasers. There are two main laser techniques for plaque or tumor removal. One involves direct laser irradiation of the arterial wall, which could have danger is the accidental laser irradiation of the arterial wall, which could have serious consequences. The other laser method consists of laser-heating a solid tip, and localized thermal destruction of the tumor or plaque by the tip. This would be the preferred technique if one could easily measure and control the tip temperature. Prior art methods are unsuitable because they require a temperature probe external to the heated tip. This occupy precious space in an already tight environment. According to the teachings of this invention one can make the heated tip its own temperature probe. This can be achieved by incorporating within the heated tip a temperature-sensing material chosen from the group of luminescent materials having a temperature-dependent light absorption coefficient, discussed in section 2.1 above.

Figure 24A:
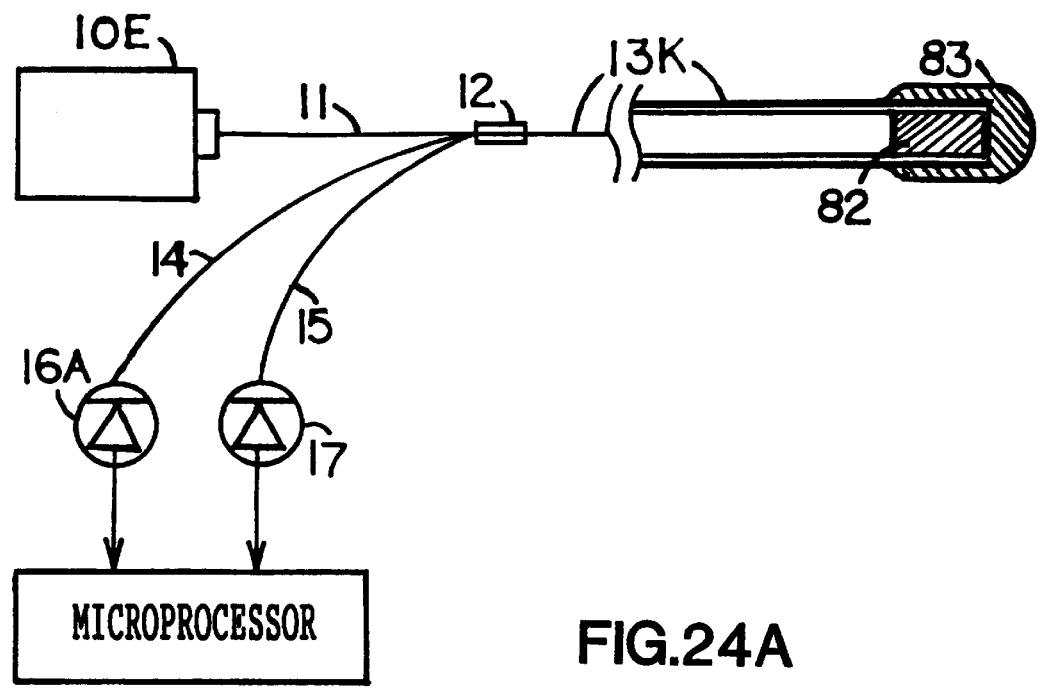
FIG. 24A illustrates a system for laser angioplasty with a temperature-sensing 'hot tip'.

A preferred embodiment of a device for controlling temperature in laser angioplasty is illustrated in FIG. 24A. A Nd:YAG laser 10E injects a C. W. laser beam of 1.06 $\mu$m wavelength and an optical power $P_o$ of the order of 10 watts or greater, through the input fiber 11 and coupler 12, into the optical fiber 13K. The distal end of the fiber is terminated in a Nd:YAG probe 82 inside an opaque solid tip 83. Most of the intensity of the laser beam is absorbed within the opaque tip, and a small fraction $\alpha_v P_o$ is absorbed by the $Nd^{3+}$ ions in the Nd:YAG crystal. As the tip 83 gets hot, the magnitude of $\alpha_v$ increases, and the luminescence intensity generated at the Nd:YAG probe increases accordingly, this intensity being indicative of the probe temperature. The luminescence from the probe can be separated from the laser radiation from the Nd:YAG laser because most of it is emitted at wavelengths different from the 1.064 $\mu$m laser radiation. In practice this is done by directing the probe luminescence, through coupler 12 and fiber segment 14 to photodetector 16A, which is made spectrally selective to the probe luminescence by a multilayer dielectric interference filter coated on the photodetector window. A photodetector 17, made spectrally selective to the wavelength of 1.064 $\mu$m of the Nd:YAG laser, monitors the backscatter laser radiation and is used for referencing the luminescence intensity to the intensity of the laser radiation. The microprocessor processes the signals from both photodetectors into a signal indicative of the probe temperature. When the highest desired temperature is reached, the microprocessor sends a signal to the laser power supply switching off the Nd:YAG laser.

It may be emphasized that the temperature measurement and control does not require the introduction into the patient's body of anything other than the laser radiation delivery fiber guide and the hot tip at the end of it.

12.0 Sequential Multiplexing and Transmission of Signals from Electronic Sensors on a Continuous Length of Optical Fiber.

The systems described above for the measurement of distributed forces using as a sensing probe a continuous length of an optical fiber are all based on the use of at least two light-building regions in the optical fiber, wherein a fraction of the intensity of the pulsed or AC-modulated interrogating light launched into one region is deflected into the second region. Several types of such fibers have been described and illustrated with appropriate figures, where the two light-guiding regions are labelled differently for different fiber types. For the purposes of this application the light-guiding region into which the interrogating light is launched is designated herein as region A, regardless of the type of fiber, and the light-guiding region into which a fraction of the intensity of the interrogating light is deflected is designated as region B. In all of the above-described embodiments the light deflected into region B at any point along the fiber is processed within region B into a light separable from the interrogating light and from light deflected at any other point by another force acting simultaneously on the fiber. In the case of the optical fiber described in section 3.5 the lights deflected into region B at different points are separated in the time domain in the transmission mode, by causing them to arrive at the distal fiber end at different resolvable times. This fiber, like the ones in which luminescence conversion occurs in region B, can be used for multiplexing the signals coupled simultaneously into the fiber by numerous sensors or other devices. In many industrial applications the signals may be coupled into the fiber sequentially, rather than simultaneously, so one can use a simpler force-sensing fiber, and the system must comprise means for instructing the sensors (or other devices) to couple their signal into the fiber in the proper sequence. Such a system is described below, with reference in FIG. 25.

Figure 25:
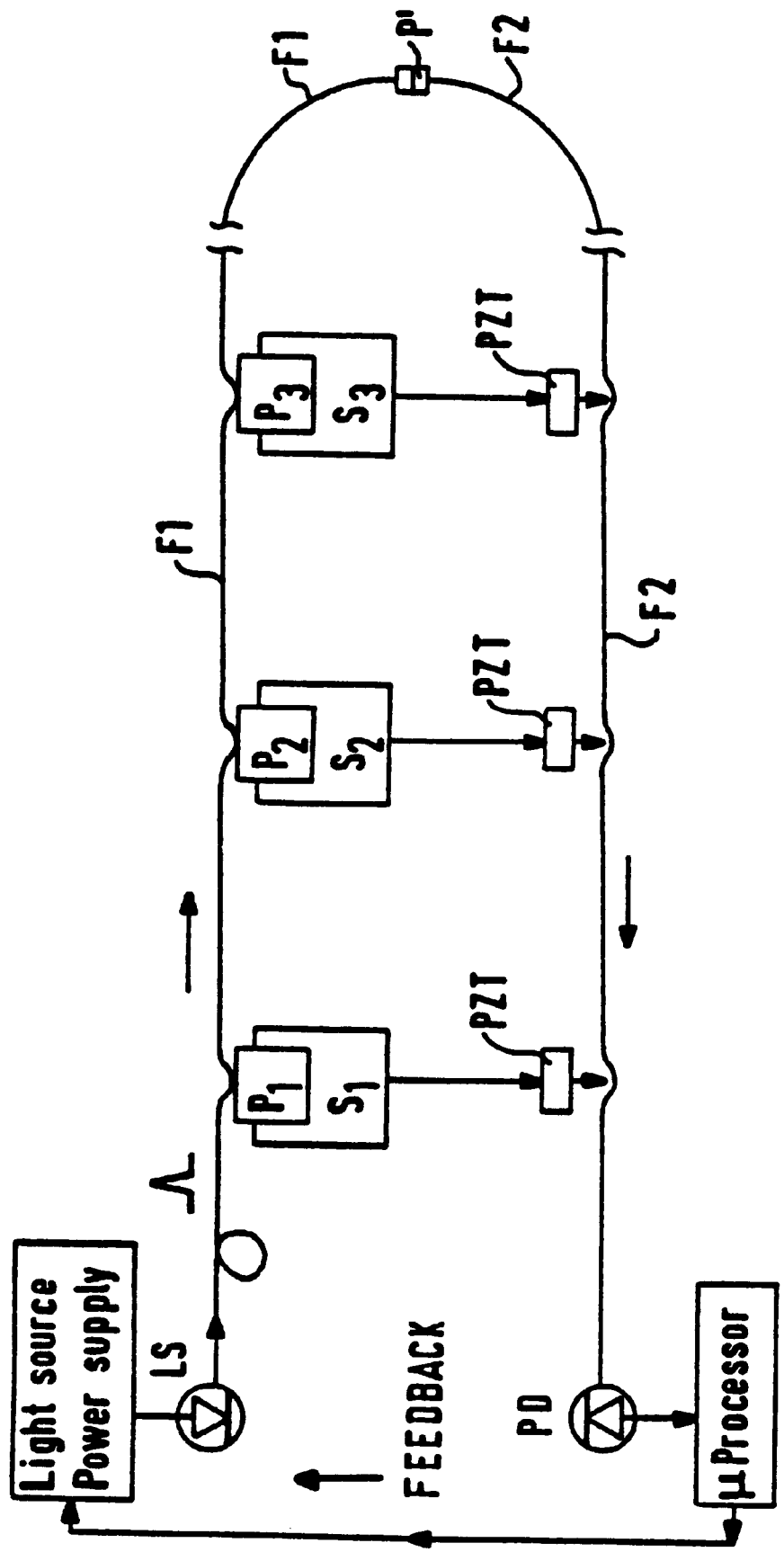
FIG. 25 is a representation of a system for the sequential multiplexing and transmission of signals from electronic sensors on a continuous optical fiber length

Referring to FIG. 25, the fiber system comprises F1 and F2 spliced together at point P'. Both fibers F1 and F2 comprise a glass core 1 with an index of refraction $n_1$ and a glass cladding 2 with an index of refraction $n_2$ lower than $n_1$. Fiber F1 has a transparent coating 3' around cladding 2, having an index of refraction $n_3$ not lower than $n_2$. Fiber F2 has a transparent second cladding 4 around cladding 2, having an index of refraction $n_4$ lower than $n_2$. Sensors $S_1$, $S_2$, $S_3$ and others not shown are connected non-invasively to fiber F1 through their photodetectors $P_1$, $P_2$, $P_3$ and others. The non-invasive connection consists of a microbend on the fiber. The microbend deflects a fraction of the intensity of the interrogating light from light source LS out of the fiber core 1 into the cladding 2 of fiber F1. An index-matching transparent thermoplastic adhesive couples the deflected light to the photodetector. The interrogating light is in the form of short light pulses superposed on a continuous DC or AC beam. Each light pulse instructs the sensor to 'write' its signal output (for instance the magnitude of a pressure) on fiber F2 after a pre-selected interval t and for a time $\Delta t'$. Each interval t is set so that a sensor 'writes' its information on fiber F2 after the preceding sensor has finished coupling its own information into the fiber. The 'writing' consists of, for example, a microbending force with a frequency which is a known function of the value of the measurand. The microbending force is produced by a piezoelectric transducer PZT mechanically connected to a fiber microbender M. The microbending force deflects a fraction of the intensity of the interrogating light out of the fiber core 1 into cladding 2, where it is trapped by total internal reflection from the second cladding 4 and transmitted to the photodetector PD. The optical interface between fiber F2 and photodetector PD can be so designed that only the cladding modes reach the photodetector, so as to eliminate or minimize the background noise from the core modes.

The sensors themselves are preferably, but not necessarily, silicon micromachined sensors requiring only small electrical powers to operate, typically of the order of tens of microwatts. Thus they can be powered by small batters which, due to the low powers required, could give years of unattended service. Alternatively, the sensors could be powered remotely by light source LS.

The electronic system which instructs each sensor to couple its information to fiber F2 at a pre-set time is essentially a light-activated switch with a time delay for opening and closing, relative to the time of arrival of the light pulse at the photodetector. Such timed electronic switches are well known in the electronics field.

The system described with reference to FIG. 25 is an example of a so-called "hybrid" system, comprising electrical sensors and fiberoptic transmission of the sensor signals. A well designed hybrid system combines the advantages of already proven electrical sensor technology with the immunity to electromagnetic interference of optical signal transmission.

One advantageous feature of the system illustrated in FIG. 25 is the capability of inter-sensor or inter-device communications. Light source LS can transmit any information to any device connected to the fiber through its photodetector, including commands to perform any function for which the sensor or device is suited. If, for example, it is required that sensor $S_i$ transmit the value of the physical parameter it is monitoring to sensor $S_3$, then the microprocessor which processes the photosignals from photodetector PO will feed back the information from sensor $S_1$ to the power supply of the light source LS, and this information will be converted into a modulation of the light output of LS as it is transmitted in the core for sensor $S_3$. Thus any sensor or device in the multiplexed system can 'talk' to any other sensor or device.

The advantages of sequential reading of the outputs of all the sensors include the following:

1) All the sensors and/or devices may share a relatively short length of conventional optical fiber (whether single mode or multimode) with no cross-talk problem;

2) The power requirements of the interrogating light source are greatly reduced compared to the case if all the sensors had to transmit their information to the photodetector PD simultaneously; and 3) The electro-optical system, including the information-processing hardware, is greatly simplified, as the signal from one sensor only is received by the photodetection system at any one time.

13. Visual Detection of Leaks of Cryogenic Fluids.

At the end of Section 3.1 I described a distributed fiber optic sensing system suitable for detecting leaks of cryogenic fluids. An alternate way of detecting leaks of cryogenic fluids is to paint the walls of the container with a photoluminescent paint the luminescence color of which, when excited with ultraviolet radiation, is a sensitive function of the wall temperature. A leak of cryogenic fluid will decrease the temperature of the wall nearest the location of the leak and thus change the luminescence color at that point, thus revealing the leak. Suitable paints include acrylic paints containing dissolved therein a mixture of terbium and europium chelates, the terbium chelate characterized by a green luminescence the efficiency (and hence, intensity) of which is low at ambient temperatures and increases substantially with a decrease in the paint temperature. Examples of terbium chelates showing this behavior are terbium tris(1-phenyl, 1–3 butanedione)-1,10 phenanthroline and terbium tris(1-phenyl, 4-trifluoromethyl 1–3 butanedione)-1,10 phenathroline.

In these chelates each central terbium ion ($Tb^{3+}$) is bound to three ligand molecules of the substituted butanedione and one ligand molecule of 1,10 phenanthroline. The europium chelates are preferably made from the same ligands, differing only in the identity of the central ion. These europium chelates have an orange-red luminescence with an efficiency which is already high at ambient temperatures and does not increase substantially with a decrease in temperature, or increases to a much smaller extend than the increase of the efficiency of the terbium luminescence. Thus, as the paint temperature decreases over a spot near a leak, the luminescence color changes according to the extent of the temperature drop, from near orange-red to yellow-green.

14. A Fiber Optic Liquid Level Indicator.

The prior art liquid level indicators consist of a vertically disposed optical fiber having at its lowest point a prism, bare fiber core or other component which, when relatively clean and in contact with air or other gases or vapors, allow the interrogating light to be transmitted to a photodetector, but interrupt said transmission when in contact with the liquid. One disadvantage of these indicators is that the surface of these optical components has to be kept relatively clean, but it eventually becomes fouled up and interrupts the transmission of light even when not in contact with the liquid to be measured. The optical temperature probes of this invention allow the construction of a liquid level indicator free from this flaw. The indicator operates on the principle that a small temperature probe which absorbs light of wavelengths $\lambda_a$ will be heated by the absorption of said light to a substantially higher temperature when surrounded by air or any other gaseous medium than when immersed in a liquid at ambient temperature. If the probe is photoluminescent and the luminescence intensity is a sensitive function of temperature, as is the case with the probe materials discussed in section 2.1, then one can tell from the probe temperature under a given interrogating light intensity whether the probe is or is not immersed in the liquid. The probe works best when the temperature of the liquid is not higher than that of the air or vapor above the liquid. This condition operates in the example of a preferred embodiment described below. The liquid container is a gasoline tank.

In operation, a small optical probe containing dissolved therein luminescence centers chosen from the materials discussed in section 2.1 and attached to one end of an optical fiber is placed in the liquid container at the level at which the container is to be filled. Interrogating light of an intensity $P_o$ and wavelengths at which the luminescence centers absorb a fraction $\alpha P_o$ of the interrogating light which increases with increasing temperature is injected at the other fiber end. The probe also contains a light-absorbing material in a concentration sufficient to absorb most of the intensity of the interrogating light. This intensity is chosen so that it increases the temperature of the probe in air by an amount $\Delta T$ at least several times greater than the minimum detectable temperature change. When gasoline is gradually pumped into the tank, its level continuously rises until it reaches the probe. As soon as the probe becomes immersed in the gasoline, its temperature drops to that of the gasoline. The temperature drop immediately alerts the operator (or the automated system, if such is the case) that the tank has been filled to the desired level. The temperature drop produces a signal for the pump to stop its operation.

15. Fiberoptic Bus-Organized Systems for Data Communications and Sensor Data Acquisition.

Any sensor signals which are in the form of or can be converted into acoustical or other mechanical forces could be coupled noninvasively to the fibers discussed in section 3.5, having two light-guiding regions of different effective optical path length. For example, numerous existing sensors and devices with a mechanical frequency output include flowmeters and pumps, whose signals could be coupled to the subject fiber through a fiber bending frequency proportional to the flow rate or the rate of rotation of the pump impeller. Owing to recent advances in micro-machined silicon sensors, and their suitability for constructing 'intelligent' sensors, it can at least be argued that the main attraction of fiber optics will increasingly lie in the electrically-passive transmission of noninvasively coupled signals from sensors and/or other devices to a remote processing unit, rather in the generation of the signals. It is already economically viable to incorporate just enough processing capability into a microchip sensor to convert the sensor signal into a pulse rate or frequency output. This could drive an inexpensive microvibrator attached noninvasively to the fiber of this work, allowing the essentially error-free transmission to a remote station of the signal from that sensor and, simultaneously or in any arbitrary sequence, the signals from numerous other sensors so coupled to the fiber. Since the interrogating light pulse rate for a 1 Km long fiber can be of the order of $10^7$ Hz, each vibration period will be sampled by thousands or more interrogating light pulses, more than enough to accurately reproduce the instantaneous sensor signal and to measure rapid signal changes in real time, including voice microphone signals.

The fiber described in section 3.5, having two light-guiding regions of different optical path length, allows the real time collection, storing and integration of the electrical signals produced by each and all photons or group of photons per signal pulse arriving at the photodetector from each force-sensing point along the fiber. Since the fiber is so constructed as to automatically demultiplex and time-resolve the optical signals from each sensing point, these signals, and their time evolution, could all be captured, stored and integrated as a two-dimensional distribution of electrical charges in a scan converter or any other image storage tube or solid CCD array, each resolvable spot in the two-dimensional array representing the time-integrated charge within a 'TV' frame.

Figure 26:
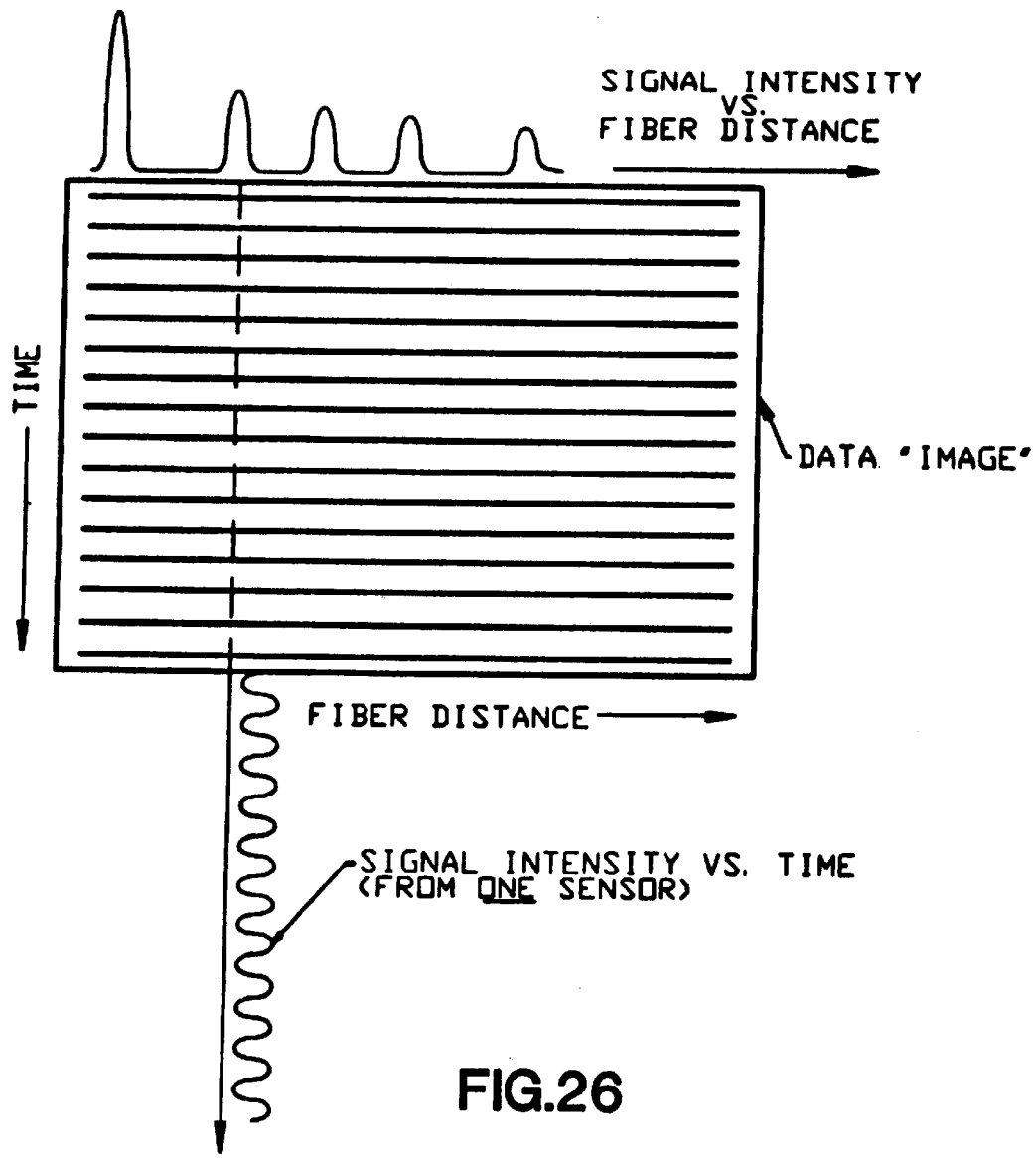
FIG. 26 illustrates a fiber optic bus-organized system for sensor data acquisition, using the fiber of FIG. 9.

An electro-optical system allowing said real time signal collection, storing and integration is illustrated in FIG. 26. Each horizontal line contains information on the light intensity generated at a given instant from each spatially resolvable element of the fiber, and the location of each all sensing points. Each point could include the signals from hundreds, or thousands, or more interrogating light pulses, depending on the pulse repetition frequency (PRF) of the interrogating light. The PRF can be any chosen frequency up to the order of about $10^7$ Hz. Each vertical line represents the intensity changes as a function of time for each corresponding, fixed point along the fiber. For example, the rotor of a turbine flow meter or pump will produce an oscillatory signal as illustrated in FIG. 26, the period of oscillation being indicative of the flow rate. Another vertical scan line could reproduce human speech picked up by a voice microphone. The number of 'TV' frames per second (the refresh rate) could be adjusted at will, so that each resolvable spot in the two-dimensional charge distribution can be the sum of numerous pulse signals.

16. An infrared Image Converter.

The teachings of this invention can be applied to the construction of a sensitive infrared-to-visible image converter. It was shown in section 2.1 that the absorption of light of photon energy lower than the energy of a luminescent level of a material is strongly temperature-dependent. This fact can be used as a basis for constructing sensitive infrared-to-visible image converters, especially at liquid helium temperatures. A probe which absorbs infrared radiation undergoes a temperature increase. Referring to FIG. 1 and equation (5) of section 2.1, it can be noticed that for any value of $(E_v/kT)$ the temperature coefficient of the luminescence intensity $I_f$ increases as the initial absolute temperature decreases. The relative increase $\Delta I_f$ in the luminescence intensity follows the relation $$\Delta I_f/I_o = (E_v/kT^2)\Delta T$$

or $$\Delta I_f/I_o = (E_v/kT^2)(H/C_v)$$

where H is the heat generated by the absorbed infrared radiation and $C_v$ is the specific heat of the probe. It is known that the specific heat of essentially all materials is orders of magnitude smaller at liquid helium temperatures than at ordinary temperatures. Thus, if the probe is made thin to reduce its thermal mass, a relatively low intensity of infrared radiation can be converted into a substantial increase of the intensity of the fluorescence light emitted by the probe.

Figure 27:
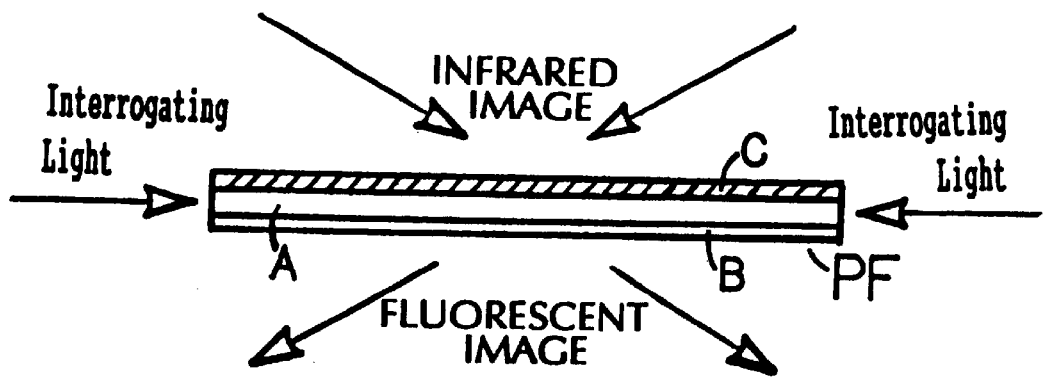
FIG. 27 shows an infrared image conversion film according to the invention.

A preferred embodiment of an infrared image converter according to this invention is illustrated in FIG. 27. The probe is a two-dimensional tri-layered thin plastic film PF doped with a fluorescent dye chosen from the group of plastic-soluble dyes including red- or infrared fluorescing porphyrins, phthalocyanins, violanthrone, isoviolanthrone and their derivatives. The total thickness of the film is smaller than 500 $\mu$m, and preferably smaller than 50 $\mu$m. Layer A has an index of refraction $n_1$ and contains the dye dissolved therein. Layer B is clear and has an index of refraction $n_2$ substantially lower than $n_1$, and layer C is an infrared-absorbing, visible reflecting thin metal film like nickel. The film is exposed to the infrared image to be converted through lens D. Interrogating light of wavelength $\lambda_v$, is injected into layer A from the edges or by a prism coupler (not shown). Referring to FIG. 1, the interrogating light has a photon energy equal to $(E_s-E_v)$. Referring again to FIG. 27, the interrogating light will propagate along film layer A and, at each point, a temperature-dependent fraction $\alpha$ of its intensity will be absorbed and will generate fluorescence light with an intensity proportional to $\alpha$, the magnitude of $\alpha$ and the intensity of the fluorescence increasing with increasing temperature according to equation (3) of section 2.1. Thus, an infrared image forced on the film will generate an image having the wavelengths of the fluorescent dye. The wavelengths are well within the sensitivity range of current television camera sensors. Thus, by focusing the fluorescent image into a TV camera, the image can be displayed on an ordinary television screen.

17. Fiber Optic Distributed Temperature Sensor Based on Anomalous Dispersion.

It is well known that the index of refraction of a material undergoes a relatively large change at wavelengths in the vicinity of an optical absorption band. This phenomenon is known as "anomalous dispersion", and the extent of the change follows approximately the Sellmeier equation $$n^2 = 1 + AN\lambda^2/(\lambda^2 - \lambda_o^2)$$

wherein n is the index of refraction, $\lambda$ is the variable wavelength, $\lambda_o$ is the wavelength at the peak of the absorption band, A is a constant, and N is the number of light-absorbing molecules or atoms.

It is also known that N increases with increasing temperature for a wavelength $\lambda_v$ at the tail of the absorption band. Therefore, the value of n will also increase with increasing temperature at wavelengths longer than $\lambda_0$. The temperature dependence of n at the wavelength $\lambda_v$ could then be used to measure temperature. If the material is part of the core of a long optical fiber, then the fiber can be used as a probe for measuring spatially averaged and/or distributed temperatures.

When used as a distributed temperature sensor, a suitable arrangement uses as the probe an optical fiber with a segmented core as shown in FIG. 16. In one preferred embodiment the probe is a long optical fiber F having a segmented light guide having a central core A with a diameter of about 5.0 micrometers ($\mu$m), an index of refraction $n_1$, and made of glass doped with a rare earth ion, for example trivalent ytterbium $Yb^{3+}$). Around this central region there is a second region B having a diameter of about 8.0 micrometers, an index of refraction $n_2$ only slightly lower than $n_1$ and doped with a material having backscatter characteristics different from those of region A, for example Raman scattering with a different Stokes shift. Around region B there is a thin cladding C with an index of refraction $n_3$ substantially lower than $n_2$. Around cladding C there is an outer cladding D with an index of refraction $n_4$ higher than $n_3$ and only slightly lower than $n_2$. Regarding its index profile, the fiber is essentially a single mode "W" fiber with a segmented core, where region A is the central part of the core and region B is the other segment.

A preferred embodiment of a distributed fiber probe based on anomalous dispersion uses backward-stimulated Raman scattering (BSRS), wherein one of the two light-guiding regions A or B is comprised of material capable of stimulated Raman scattering. This provides a system alternate to the systems for the measurement of distributed temperatures using fluorescent dyes (discussed in section 2.2), distribute light amplification with laser-active rare earth-doped fibers (discussed in sections 6.1–6.3), or a BSRS system with the segmented core of FIG. 16 where the two segments have indices of refraction $n_1$ and $n_2$ with substantially different temperature coefficients. It was already indicated in section 6.3 that if these indices of refraction have different temperature coefficients, then the intensity distribution of the interrogating light between regions A and B will be temperature-dependent, and the fiber may be used as a sensitive distributed temperature probe. But it is not particularly easy to fabricate a fiber with a segmented core in which the segments have different thermal coefficients of their indices of refraction. The advantage of using anomalous dispersion is that said different thermal coefficients are not needed. When the fiber is interrogated at a wavelength $\lambda_v$ at which the light absorption is temperature-dependent, the relative intensity distribution of the interrogating light between segments A and B of the segmented core will also be temperature-dependent. Then, by monitoring the intensity of the Raman-scattered light at the Stokes shift characteristic of the dopant of one of the segments, one can measure said relative intensity distribution, which is an accurate temperature indicator. And if the intensity of the Raman-scattered light is measured with an optical time domain reflectometer (OTDR), then one obtains temperature distributions along the fiber length.

In the above example where segment A is doped with $Yb^{3+}$, a suitable interrogating light wavelength $\lambda_v$ is 1064 nanometers (nm), easily available from a Nd:YAG laser at intensities sufficiently high to generate stimulated Raman scattering. At this wavelength the index of refraction $n_1$ will be temperature-dependent. The change of the index $n_2$ of the outer segment B will be very small compared to the change of $n_1$.

A preferred embodiment of a distributed fiber probe based on anomalous dispersion uses polarization-independent backward-stimulated Raman scattering (BSRS), where one of the two light-guiding regions A or B is comprised of material capable of stimulated Raman scattering.

18.0 Fiberoptic Measurement of Distributed Magnetic Fields and/or Electrical Currents.

There is a deeply felt need to remotely measure electrical currents in electrical power generation and distribution systems. Electrical sensing techniques are not suitable because of interference with the transmission of the signals by the high electrical fields in these systems. A great deal of effort has been underway at numerous laboratories to develop a suitable fiber optic measurement technique. Prior art fiber optic techniques make use of the Faraday effect, namely the rotation of plane polarized light (Faraday rotation) under the action of the magnetic field generated by the electrical current. In practice, an optical fiber having a core made of a Faraday rotator glass is coiled around a current-carrying conductor. The interrogating light is polarized by means of a first polarizing filter and injected into the fiber core at the fiber launch end. The current-generated magnetic field rotates the plane of polarization of the light propagating along the fiber core to a degree determined by the magnitude of the electrical current. In order to determine the degree of polarization, and hence the magnitude of the current, the light exiting from the fiber distal end is split into two beams. One of the beams is passed through a second polarizing filter orientated parallel to said first polarizing filter, and the other beam is passed through a third polarizing filter orientated perpendicular to said second polarizing filter. The relative intensities of the lights passing through said second and said third polarizing filters are an indicator of the degree of rotation of the plane of polarization of the interrogating light injected into said fiber core and, hence, of the magnitude of the electrical current.

The prior art described in the preceding paragraph is relatively complicated in that it requires a plurality of polarizing filters for each sensing point, and it does not lend itself easily to the measurement of distributed electrical currents at a plurality of locations.

The techniques of this invention provide a simple and effective way of measuring distributed electrical currents and/or magnetic fields. As in the prior art, the electrical current (or magnetic field) is measured through the Faraday effect but, in contrast to the prior art, there is no need for polarizing filters, and measurements can be made at a plurality of locations using a single, continuous optical fiber probe.

Figure 28:
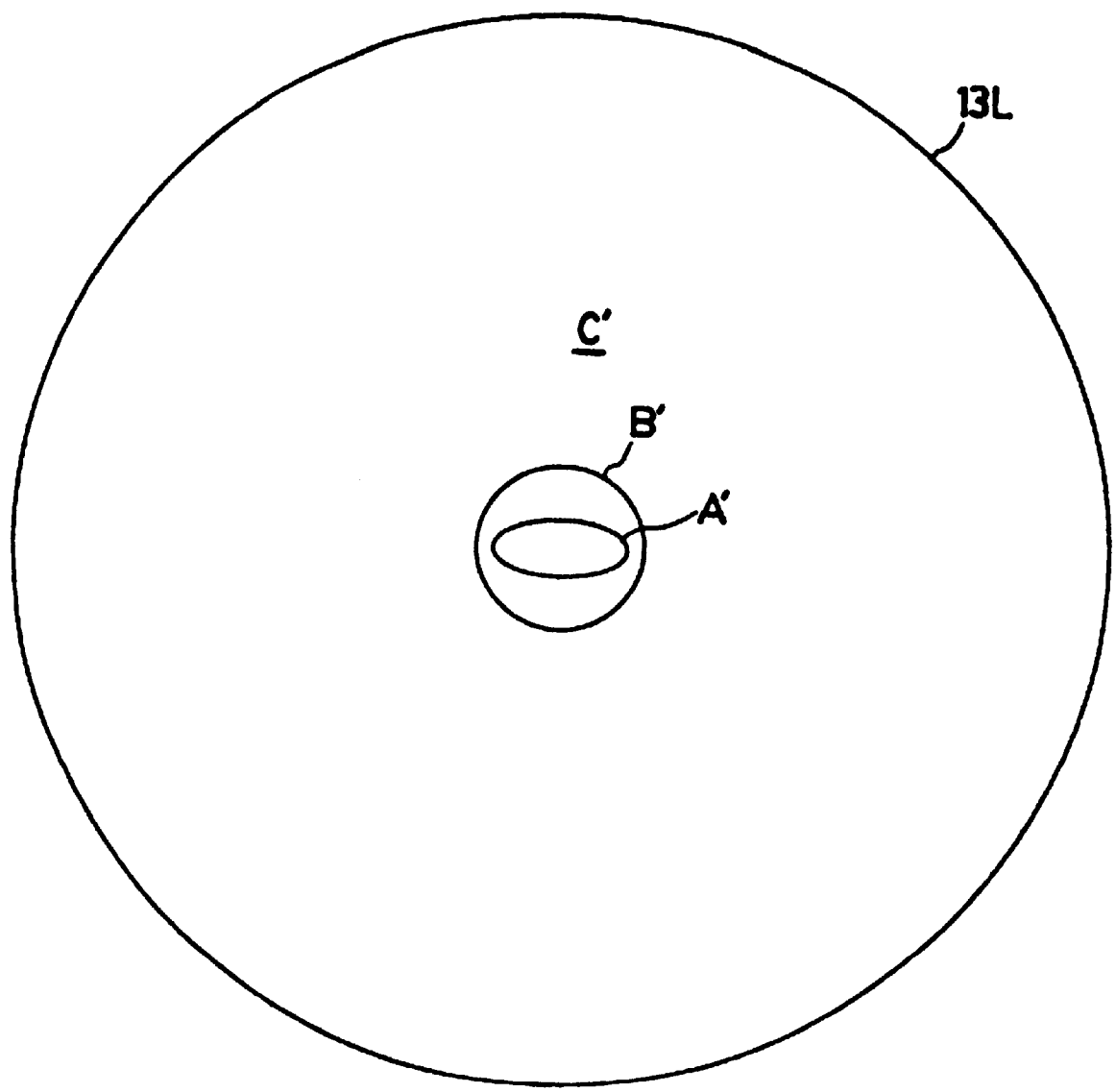
FIG. 28 is representative of an embodiment of an optical fiber suitable for measuring distributed magnetic fields and/or electrical currents according to the BSRS techniques.

FIG. 28 illustrates one embodiment of an optical fiber suitable for measuring distributed magnetic fields and/or electrical currents according to the BSRS techniques described in section 6.4 above. The fiber 13L has a substantially single mode or few mode segmented core comprising an inner segment A' with an elliptical cross section having its larger dimension of about 4 micrometers ($\mu$m) or smaller, made of a Faraday rotator glass and having an index of refraction $n_1$. This segment is surrounded and in contact with an outer segment B' of circular cross section, having a diameter about 2 micrometers larger than the larger dimension of segment A' and an index of refraction $n_2$ lower than $n_1$. The segmented core is surrounded by a cladding C' having an index of refraction $n_3$ substantially smaller than $n_2$. The glass compositions of segments A' and B' are characterized by Raman-scattering coefficients which differ substantially within at least one Stokes band within which one of the two glasses has a relatively strong Raman coefficient. The ellipticity of core segment A' results in the selective transmission by said segment, in the absence of any external influence, of light of a defined polarization. Because of the smallness of the core, a substantial fraction of the intensity of the light propagating along segment A' will also propagate along segment B'. Now, if a length of the fiber is coiled around an electrical conductor, any electrical current carried by the conductor will generate a magnetic field which will cause a rotation of the plane of polarization of the interrogating light being carried by segment A'. Depending on the degree of rotation, a magnetic field-dependent fraction of the intensity of the interrogating light propagating along segment A' will propagate along segment B'. As the interrogating light continues to propagate along the fiber into a fiber length not subjected to a magnetic field or other forces, its initial intensity distribution between segments A' and B' is restored.

An embodiment of a device for measuring distributed electrical currents and/or magnetic fields uses basically the same arrangement as illustrated in FIG. 13 and the technique discussed in section 6.4 above. The fiber 13L has a segmented core wherein segment A' has a relatively strong Raman scattering coefficient $\alpha_R$ at a Stokes shift $\Delta v$. The light source 10B launches into the elliptical core segment A' of the fiber, at the proximal fiber end (the launch end), interrogating ("pump") light pulses of a duration T of the order of nanoseconds or shorter, wavelengths $\lambda_s$ and power sufficient to generate observable optical gain in a counter-propagating wave of wavelengths $\lambda_f$ corresponding to a Stokes Raman shift $\Delta v$ of the interrogating light wavelength according to the relation $$\lambda_f^{-1} = \lambda_s^{-1} - \Delta v$$

At the other fiber end, one injects into segment A' a CW light beam of wavelengths $\lambda_f$ from light source 26. The CW beam interacts with the pump pulses and is directed through the fiber optic coupler 12B to photodetector 16. In the absence of a magnetic field or other forces, the intensity distribution of the interrogating light between segments A' and B' will be determined at least in part by the values of $n_1$ and $n_2$. At any point where the fiber is under a magnetic field, the rotation of the plane of polarization of the interrogating light propagating along segment A' will cause a deflection of a fraction of the intensity of this light to segment B'. This will decrease the intensity of the pulse-amplified counterpropagating beam at that point. A sensing point at a fiber distance z from the fiber launch end will generate pulsed signals of wavelengths $\lambda_f$ arriving at the photodetector in a time $(2z.n_1/c)$ after the time of launching of the pump pulse.

In an alternate embodiment, it is segment B' of the fiber core which has a relatively strong Raman scattering coefficient $\alpha_R$ at a Stokes shift $\Delta v$, so that a magnetic field acting on the fiber increases the intensity of the pulse-amplified signals from the sensing points along the fiber.

In another fiber embodiment, the Faraday-rotating elliptical core replaces the single or few-mode core 1 of the optical fiber 13A illustrated in FIG. 9, having two light-guiding regions of substantially different optical path lengths. Except for the ellipticity of the central core, the fiber is essentially the same as the fiber illustrated in FIG. 9, and the indices of refraction $n_1$, $n_2$, $n_3$ and $n_4$ of regions A", B, C and D have essentially the same relative magnitudes as those of the fiber of FIG. 9. Interrogating light pulses with a duration of the order of nanoseconds or shorter are launched into the elliptical core. At any point along the fiber under the action of a magnetic field, a fraction of the intensity of the interrogating light pulses are deflected to the multimode core C, where it generates a signal pulse arriving at the fiber distal end separated in the time domain from the undeflected interrogating light pulses and from signal pulses generated at different points along the fiber.

Since changes may be made in the foregoing disclosure without departing from the scope of the invention herein involved, it is intended that all matter contained in the above description and depicted in the accompanying drawings be construed in an illustrative and not in a limiting case.

I claim:

1. A device for medical treatment of biological tissue by optical irradiation at wavelengths within a pre-selected spectral region, comprising:

(a) a source of high power laser radiation of wavelength or wavelengths $\lambda_1$;

(b) a fiber optic light guide having a first end optically coupled to said source and a second end terminated by a cylindrical light-diffusing tip including a photoluminescent material so characterized that when exposed to said laser radiation, it absorbs at least a substantial fraction $\alpha$ of the intensity of said radiation and re-emits the absorbed radiation nearly isotropically around said tip as luminescence radiation diffused into said biological tissue and having wavelengths $\lambda_f$ different from $\lambda_1$ and within said pre-selected spectral region for irradiation of said tissue; and (c) means for injecting said laser radiation into said first end of said fiber optic light guide.

2. A device as claimed in claim 1 wherein the value of said fraction $\alpha$ is at least 0.4.

3. A device as claimed in claim 1 wherein said tip is heated by said laser radiation of preselected wavelength or wavelength $\lambda_1$ and wherein said tip is its own temperature probe, said photoluminescent material being additionally so characterized that, when interrogated with interrogating light of a wavelength or wavelengths $\lambda_v$ within a suitable spectral region for said photoluminescent material and an intensity $P_o$ injected into said tip, a fraction $\alpha P_o$ of the intensity of said injected light is converted within said tip into a light separable from the interrogating light and emitted from the tip at wavelengths $\lambda_f$ different from $\lambda_v$, the magnitude of $\alpha$ varying in a known manner with variations of the temperature of the tip over a temperature range of operation of the device, said emitted light of wavelengths $\lambda_f$ having an intensity which increases in a known manner with the value of $\alpha$ over said temperature range, the device additionally comprising (a) a source of said interrogating light of wavelength or wavelengths $\lambda_v$;

(b) means for injecting said interrogating light of wavelength or wavelengths $\lambda_v$ into said first end of said fiber optic light guide;

(c) means for directing a fraction of the intensity of said light of wavelengths $\lambda_f$ emitted from said tip to photodetector means; and (d) photodetector means for measuring said fraction of the intensity of said light of wavelengths $\lambda_f$, said fraction being indicative of the tip temperature.

4. A device as claimed in claim 3 wherein said photoluminescent material is a solid doped with trivalent inorganic ions chosen from the group comprising the ions of chromium, neodymium, erbium, ytterbium and holmium.

5. A method for medical treatment of biological tissue by optical irradiation at wavelengths within a pre-selected spectral region, comprising the steps of:

(a) providing a source of high power laser radiation of preselected wavelength or wavelengths $\lambda_1$;

(b) providing a fiber optic light guide having a first end and a second end, said second end terminated by a cylindrical light-diffusing tip including a photoluminescent material so characterized that when exposed to laser radiation of wavelengths $\lambda_1$, it absorbs at least a substantial fraction $\alpha$ of the intensity of said radiation and re-emits the absorbed radiation nearly isotropically around said tip as luminescence radiation diffused into said biological tissue and having wavelengths $\lambda_f$ different from $\lambda_1$ and within said pre-selected spectral region for irradiation of said tissue;

(c) placing said tip of said light guide in optical communication with said tissue; and (d) injecting said laser radiation into the first end of said light guide, thereby causing the emission of said luminescence radiation and the optical irradiation of said tissue.

6. A method as claimed in claim 5 wherein the value of said fraction $\alpha$ is at least 0.4.

7. A method as claimed in claim 6 wherein said photoluminescent material is a solid doped with trivalent inorganic ions chosen from the group comprising the ions of chromium neodymium, erbium, ytterbium and holmium.

8. A method as claimed in claim 5 wherein said tip is heated by said laser radiation of preselected wavelength or wavelengths $\lambda_f$ and wherein said tip is its own temperature probe, said photoluminescent material being additionally so characterized that, when interrogated with interrogating light of a wavelength or wavelengths $\lambda_v$ within a suitable spectral region for said photoluminescent material and an intensity $P_o$ injected into said tip, a fraction $\alpha P_o$ of the intensity of said injected light is converted within said tip into a light separable from the interrogating light and emitted from the tip at wavelengths $\lambda_f$ different from $\lambda_v$, the magnitude of $\alpha$ varying in a known manner with variations of the temperature of the tip over a temperature range of operation of the device, said emitted light of wavelengths $\lambda_f$ having an intensity which increases in a known manner with the value of $\alpha$ over said temperature range, the method additionally comprising the steps of:

(a) providing a source of said interrogating light of wavelength or wavelengths $\lambda_v$;

(b) injecting said interrogating light of wavelength or wavelengths $\lambda_v$ into said first end of said fiber optic light guide;

(c) directing a fraction of the intensity of said light of wavelengths $\lambda_f$ emitted from said tip to photodetector means; and (d) measuring, with said photodetector means, said fraction of the intensity of said light of wavelengths $\lambda_f$, said fraction being indicative of the tip temperature.

* * * * *

UNITED STATES PATENT AND TRADEMARK OFFICE
CERTIFICATE OF CORRECTION

PATENT NO.   : 5,928,222
DATED        : July 27, 1999
INVENTOR(S)  : Marcos Y. Kleinerman It is certified that error appears in the above-identified patent and that said Letters Patent is hereby corrected as shown below:

Column 1,
Line 15, after "Jan. 3, 1989, now abandoned", the remainder of the paragraph should read:

-- wherein the earliest reference to the claimed matter of this application is found. --

Signed and Sealed this

Eleventh Day of December, 2001

Attest:

NICHOLAS P. GODICI
Attesting Officer      Acting Director of the United States Patent and Trademark Office